United States Patent
Lim et al.

(10) Patent No.: US 9,297,813 B2
(45) Date of Patent: Mar. 29, 2016

(54) TARGETING METABOLIC ENZYMES IN HUMAN CANCER

(75) Inventors: Bing Lim, Singapore (SG); Wencai Zhang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 2 days.

(21) Appl. No.: 13/884,891

(22) PCT Filed: Nov. 11, 2011

(86) PCT No.: PCT/SG2011/000400
§ 371 (c)(1),
(2), (4) Date: May 10, 2013

(87) PCT Pub. No.: WO2012/064286
PCT Pub. Date: May 18, 2012

(65) Prior Publication Data
US 2013/0296188 A1 Nov. 7, 2013

(30) Foreign Application Priority Data

Nov. 11, 2010 (SG) .................................. 201008288

(51) Int. Cl.
| | |
|---|---|
| C12N 15/11 | (2006.01) |
| G01N 33/68 | (2006.01) |
| A61K 31/395 | (2006.01) |
| A61K 31/519 | (2006.01) |
| A61K 31/713 | (2006.01) |
| A61K 38/17 | (2006.01) |
| A61K 38/19 | (2006.01) |
| A61K 45/06 | (2006.01) |
| C12N 15/113 | (2010.01) |
| C12Q 1/68 | (2006.01) |
| G01N 33/574 | (2006.01) |

(52) U.S. Cl.
CPC .......... *G01N 33/6893* (2013.01); *A61K 31/395* (2013.01); *A61K 31/519* (2013.01); *A61K 31/713* (2013.01); *A61K 38/177* (2013.01); *A61K 38/191* (2013.01); *A61K 45/06* (2013.01); *C12N 15/1137* (2013.01); *C12Q 1/6886* (2013.01); *G01N 33/57484* (2013.01); *C12N 2310/141* (2013.01); *C12Q 2600/118* (2013.01); *G01N 2333/90616* (2013.01); *G01N 2500/10* (2013.01)

(58) Field of Classification Search
CPC ............. C12N 15/113; C12N 2310/14; C12N 15/1137
See application file for complete search history.

(56) References Cited

U.S. PATENT DOCUMENTS

| | | | |
|---|---|---|---|
| 4,341,761 A | 7/1982 | Ganfield et al. | |
| 4,342,566 A | 8/1982 | Theofilopoulos et al. | |
| 4,353,656 A | 10/1982 | Sohl et al. | |
| 4,399,121 A | 8/1983 | Albarella et al. | |
| 4,427,783 A | 1/1984 | Newman et al. | |
| 4,444,887 A | 4/1984 | Hoffmann | |
| 4,451,570 A | 5/1984 | Royston et al. | |
| 4,458,066 A | 7/1984 | Caruthers et al. | |
| 4,466,917 A | 8/1984 | Nussenzweig et al. | |
| 4,472,500 A | 9/1984 | Milstein et al. | |
| 4,491,632 A | 1/1985 | Wands et al. | |
| 4,493,890 A | 1/1985 | Morris | |
| 4,778,054 A | 10/1988 | Newell et al. | |
| 4,811,731 A | 3/1989 | Newell et al. | |

(Continued)

FOREIGN PATENT DOCUMENTS

| | | |
|---|---|---|
| EP | 0 069 715 | 1/1983 |
| GB | 2064336 | 6/1981 |

(Continued)

OTHER PUBLICATIONS

Navarre et al. The Plant Cell; Apr. 1995;vol. 7; No. 4; 463-471.*

(Continued)

*Primary Examiner* — Brian Whiteman
(74) *Attorney, Agent, or Firm* — Wolf, Greenfield & Sacks, P.C.

(57) ABSTRACT

Targeting metabolic enzymes in human cancer Abstract Lung cancer is a devastating disease and a major therapeutic burden with poor prognosis. The functional heterogeneity of lung cancer (different tumor formation ability in bulk of tumor) is highly related with clinical chemoresistance and relapse. Here we find that, glycine dehydrogenase (GLDC), one of the metabolic enzyme involved in glycine metabolism, is overexpressed in various subtypes of human lung cancer and possibly several other types of cancers. GLDC was found to be highly expressed in tumor-initiating subpopulation of human lung cancer cells compared with non-tumorigenic subpopulation. By array studies we showed that normal lung cells express low levels of GLDC compared to xenograft and primary tumor. Functional studies showed that RNAi inhibition of GLDC inhibits significantly the clonal growth of tumor-initiating cells in vitro and tumor formation in immunodeficient mice. Overexpression of GLDC in non-tumorigenic subpopulation convert the cells to become tumorigenic. Furthermore, over-expression of GLDC in NIH/3T3 cells and human primary lung fibroblasts can transform these cells, displaying anchorage-independent growth in soft agar and tumor-forming in mice. Not only is GLDC is expressed human lung cancer, it is also up-regulated in other types of cancer, such as colon cancer. RNAi knockdown of GLDC in colon cancer cell line, CACO-2 cells, can also inhibit the tumor formation in mice. Thus GLDC maybe a new metabolic target for treatment of lung cancer, and other cancers.

3 Claims, 24 Drawing Sheets

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,035,237 | A | 7/1991 | Newell et al. |
| 5,590,645 | A | 1/1997 | Davies et al. |
| 5,837,832 | A | 11/1998 | Chee et al. |
| 5,860,419 | A | 1/1999 | Davies et al. |
| 5,873,360 | A | 2/1999 | Davies et al. |
| 6,632,666 | B2 | 10/2003 | Baust et al. |
| 7,618,814 | B2* | 11/2009 | Bentwich ............... 435/320.1 |
| 2004/0235755 | A1* | 11/2004 | Eigenbrodt .......... A61K 31/197 514/23 |
| 2005/0095592 | A1* | 5/2005 | Jazaeri et al. .................... 435/6 |
| 2009/0163591 | A1* | 6/2009 | Eigenbrodt .......... A61K 31/197 514/551 |
| 2010/0086537 | A1* | 4/2010 | Sooknanan ........ A61K 31/7088 424/130.1 |
| 2012/0183552 | A1* | 7/2012 | Joseloff ........... G01N 33/57438 424/139.1 |
| 2015/0011611 | A1* | 1/2015 | Kim ..................... A61K 45/06 514/44 A |

FOREIGN PATENT DOCUMENTS

| | | |
|---|---|---|
| GB | 2129691 | 5/1984 |
| GB | 2169265 | 7/1986 |
| GB | 2178965 | 2/1987 |
| GB | 2242134 | 9/1991 |
| WO | WO 90/13678 | 11/1990 |
| WO | WO 97/49989 | 12/1997 |
| WO | WO 98/49557 | 11/1998 |
| WO | WO 2010/126452 | 11/2010 |
| WO | WO 2012/126452 | 9/2012 |

OTHER PUBLICATIONS

Tada et al. Plant and cell physiology 46.11 (2005): 1787-1798.*
Wise et al. PNAS(2008)vol. 105 No. 48 : 18782-18787.*
Kaadige et al. PNAS(2009) vol. 106 No. 35 14878-14883.*
Book's foreword by Jim Duke, Johnathan Hartwell, Plants used against cancer Quarterman Publications, Inc. Lawrence MA, 1982 3 pages.*
[No Author Listed], Sigma-aldrich material safety data sheet. Anti-GLDC. Product No. HPA002318. Versions 5.1 and 5.2. Jun. 3, 2013 and Aug. 26, 2014. 7 pages.
Beaucage et al., Deoxynucleoside phosphoramideites—a new class of key intermediates for deoxypolynucleotide synthesis. Tetrahedron Letters. 22:1859-1862. 1981.
Biswas et al., MetDAT: a modular and workflow-based free online pipeline for mass spectrometry data processing, analysis and interpretation. Bioinformatics. Oct. 15, 2010;26(20):2639-40. Epub Aug. 11, 2010.
Brunk et al., Amino Acid Metabolism of Lemna minor L. : III. Responses to Aminooxyacetate. Plant Physiol. Jun. 1988;87(2):447-53.
Chua et al., A novel normalization method for effective removal of systematic variation in microarray data. Nucleic Acids Res. Mar. 9, 2006;34(5):e38.
Cole et al., The EBV-Hybridoma technique and its application to human lung cancer. Monoclonal Antibodies and Cancer Therapy. 1985;:77-96.
Conner et al., Detection of sickle cell beta S-globin allele by hybridization with synthetic oligonucleotides. Proc Natl Acad Sci U S A. Jan. 1983;80(1):278-82.
Cote et al., Generation of human monoclonal antibodies reactive with cellular antigens. Proc Natl Acad Sci U S A. Apr. 1983;80(7):2026-30.
Evans et al., Gene expression as a drug discovery tool. Nat Genet. Mar. 2004;36(3):214-5.
Hornsby et al., Regulation of glutamine and pyruvate oxidation in cultured adrenocortical cells by cortisol, antioxidants, and oxygen: effects on cell proliferation. J Cell Physiol. Oct. 1981;109(1):111-20.
Hu et al., ELDA: Extreme limiting dilution analysis for comparing depleted and enriched populations in stem cell and other assays. J Immunological Meth. 2009;347:70-8.
Huang et al., Systematic and integrative analysis of large gene lists using DAVID bioinformatics resouces. Nature Protocols. 2009;4(1):44-57.
Kohler et al., Continuous cultures of fused cells secreting antibody of predefined specificity. Nature. Aug. 7, 1975;256(5517):495-7.
Kozbor et al,. The production of monoclonal antibodies from human lymphocytes. Immunol Today. Mar. 1983;4(3):72-9.
Kristiansen et al. Overexpression of c-erbB2 protein correlates with disease-stage and chromosomal gain at the c-erbB2 locus in non-small cell lung cancer. European J Cancer. 2001;37:1089-95.
Landegren et al., DNA diagnostics—molecular techniques and automation. Science. Oct. 14, 1988;242(4876):229-37.
Mordenti et al., Estimation of permanence time, exit time, dilution factor, and steady-state volume of distribution. Pharm Res. Jan. 1992;9(1):17-25.
Morrison et al., Isolation of transformation-deficient *Streptococcus pneumoniae* mutants defective in control of competence, using insertion-duplication mutagenesis with the erythromycin resistance determinant of pAM beta 1. J Bacteriol. Sep. 1984;159(3):870-6.
Rhodes et al., Amino Acid Metabolism of Lemna minor L. : IV. N-Labeling Kinetics of the Amide and Amino Groups of Glutamine and Asparagine. Plant Physiol. Apr. 1989;89(4):1161-71.
Saiki et al., A novel method for the detection of polymorphic restriction sites by cleavage of oligonucleotide probes: application to sickle-cell anemia. Bio/Technology. Nov. 1985;3:1008-1012.
Warburg, On the origin of cancer cells. Science. Feb. 24, 1956;123(3191):309-14.
Yang et al., Temporally regulated expression of Lin-28 in diverse tissues of the developing mouse. Gene Expression Patterns. 2003;3:719-26.

* cited by examiner

A

B

C

TARGETING METABOLIC ENZYMES IN HUMAN CANCER

CROSS-REFERENCE TO RELATED APPLICATION

This application is a national stage filing under 35 U.S.C. §371 of international application PCT/SG2011/000400, filed Nov. 11, 2011, which claims priority to Singapore Application No. 201008288-1, filed Nov. 11, 2010, the contents of all of which are incorporated herein by reference in their entirety.

FIELD OF THE INVENTION

The present invention relates to a diagnostic or prognostic biomarker or biomarkers for screening or detection of cancer particularly lung cancer and compounds to treat the same.

BACKGROUND ART

Cancer is one of the main diseases of the $21^{st}$ century causing 13% of all deaths. New aspects of the genetics of cancer pathogenesis, such as DNA methylation are increasingly recognized as important. While there are several chemicals that can affect rapidly dividing cancer cells most of these are toxic with adverse side effects. Chemo-resistance to many of these drugs leads to relapse of patients often exhibiting more aggressive cancer progression, with little or no alternative treatments available. New diagnostics', prognostics' and treatments' are needed.

Despite numerous advances in our knowledge of cancer, our ability to develop clinically effective therapies based on this understanding has met with limited success. Current therapies can control tumor growth initially, but most patients ultimately relapse. One prominent example is lung cancer, the leading cause of cancer-related mortality with over 1 million deaths each year. NSCLC accounts for approximately 85% of all lung cancers. Although NSCLC patients with EGFR mutations respond to EGFR inhibitors initially, most patients experience a relapse within 1 year. These findings underscore the urgent need for both combination therapies and also new approaches to treat cancerous tumors. Lung cancer is a devastating disease and a major therapeutic burden with poor prognosis. The functional heterogeneity of lung cancer is highly related with clinical chemo-resistance and relapse.

Data from leukemias, germ cell tumors and a number of solid tumors support the notion that cancers are maintained by a subpopulation of self-renewing and evolving tumor initiating cells (TICs). This is also popularly known as the cancer stem cell (CSC) model. Although the validity of the CSC model is an issue of controversy in melanoma, many other solid tumors appear to follow the CSC model. Recently it was proposed that at earlier stages of tumorigenesis, rare TIC clones differentiate into non-malignant progeny to form the bulk of the tumor, while at advanced stages TIC clones constitute the bulk of the tumor. Studies have also begun to reconcile the connection between the evolving genotype of TIC clones and the surface phenotype of TICs, using mouse models of lung cancer such as those described in WO 2010/126452. Thus accumulated findings suggest that targeting TICs may be a promising approach for eradicating tumors early. However progress in the targeting of TICs to improve cancer therapy has been hindered by a lack of understanding of the molecular pathways that are critical to TICs.

Recent studies have led to an emerging appreciation of the importance of metabolic reprogramming in cancer and a resurgence of interest in the Warburg effect—the phenomenon whereby cancer cells, like embryonic cells, preferentially use glycolysis even under aerobic conditions (Warburg, 1956. Origin of cancer cells. Science 123, 309-314).

Glycine dehydrogenase (decarboxylating) (GLDC) is an enzyme belonging to the family of oxidoreductases, specifically those acting on the CH—NH2 group of donors with a disulfide as acceptor. This enzyme participates in glycine, serine and threonine metabolism. It employs pyridoxal phosphate as a cofactor. GLDC is one of four proteins that form the glycine cleavage system in all eukaryotes which catalyzes the degradation of glycine. High levels of glycine in humans or glycine build up is known to glycine encephalopathy.

SUMMARY OF THE INVENTION

The present invention seeks to ameliorate at least some of the difficulties discussed above. This may be useful in treating or slowing cancer cells to ameliorate some of the difficulties with the current treatment of cancer. The invention further seeks to provide in vivo and in vitro methods, for inducing apoptosis or prognosing suitable treatments.

Accordingly the first aspect of the invention is a method for inhibiting cell proliferation comprising the steps of: administering to a cell an inhibitor of GLDC expression.

Preferably the method further provides the step of adding a chemotherapeutic agent to the cell.

A further aspect of the invention is a compound comprising an inhibitor of GLDC expression.

Preferably the compound further comprises a DNA damaging agent. Preferably the DNA damaging agent is a chemotherapeutic agent.

the present invention provides a method of analyzing a cell expression profile for determining whether the cell has been isolated from cancerous tissue comprising the steps of (a) measuring an amount of glycine dehydrogenase (GLDC) nucleic acid or polypeptide in the cell isolated from tissue suspected of being cancerous; Comparing the amount of GLDC nucleic acid or polypeptide present in the cell to the amount of GLDC nucleic acid or polypeptide in a sample isolated from normal, a non-cancerous cell, wherein an amplified amount of GLDC nucleic acid or polypeptide in the cell relative to the amount of GLDC nucleic acid or polypeptide in the non-cancerous cell indicates cancer is present in the cell; and wherein the absence of an amplified amount of GLDC nucleic acid or polypeptide in the cell relative to the amount of GLDC nucleic acid or polypeptide in the non-cancerous cell indicates there is no cancer present in the cell.

A further aspect of the invention comprises a method of predicting the effectiveness of a GLDC inhibitor comprising the step of determining a first expression profile of GLDC nucleic acid or polypeptide in a cell isolated from a subject who is not diagnosed with cancer; determining a second expression profile of GLDC nucleic acid or polypeptide in a cell isolated from a subject who is diagnosed with cancer and comparing the first and second expression profile whereby when the second expression profile is 1.5 to 16 fold more than the first expression profile or preferably 2 to 10 fold more than the first expression profile the subject who is diagnosed with cancer will benefit from treatment with the GLDC inhibitor.

A further aspect of the invention comprises a method for screening for an antagonist of GLDC polynucleotide expression comprising the steps of: (a) contacting a cell that is over expressing GLDC polypeptide with a sample compound; (b) measuring the GLDC expression profile in both the presence and absence of the sample compound; and, Wherein a decrease in GLDC polypeptide expression in the presence of the sample compound in relation to the GLDC polypeptide expression in the absence of the sample compound indicates the sample compound is the antagonist.

(A) Quantitative RT-PCR analysis of GLDC in 3T3 cells overexpressing GLDC.

(B) Soft agar colony formation of 3T3 cells overexpressing GLDC or Lin28B. 5,000 live cells were seeded into soft agar and stained with INT on day 28.

(C) Quantitative analysis of colonies in soft agar. Results are plotted as average colony number per dish±s.e.m., n=2. Independent-samples T test is applied for statistics analysis. **P<0.01.

(D) Tumor formation in mice transplanted with 3T3 cells overexpressing GLDC.

(E) Statistic analysis of tumor formation efficiency in mice transplanted by 3T3 cells overexpressing GLDC.

(F) H&E staining of xenograft tumor in mice transplanted by 3T3 cells overexpressing GLDC.

(G) Immunohistochemistry staining of xenograft tumor formed from 3T3 cells overexpressing GLDC, GD, GLDC; XG, xenograft.

Figure 2:
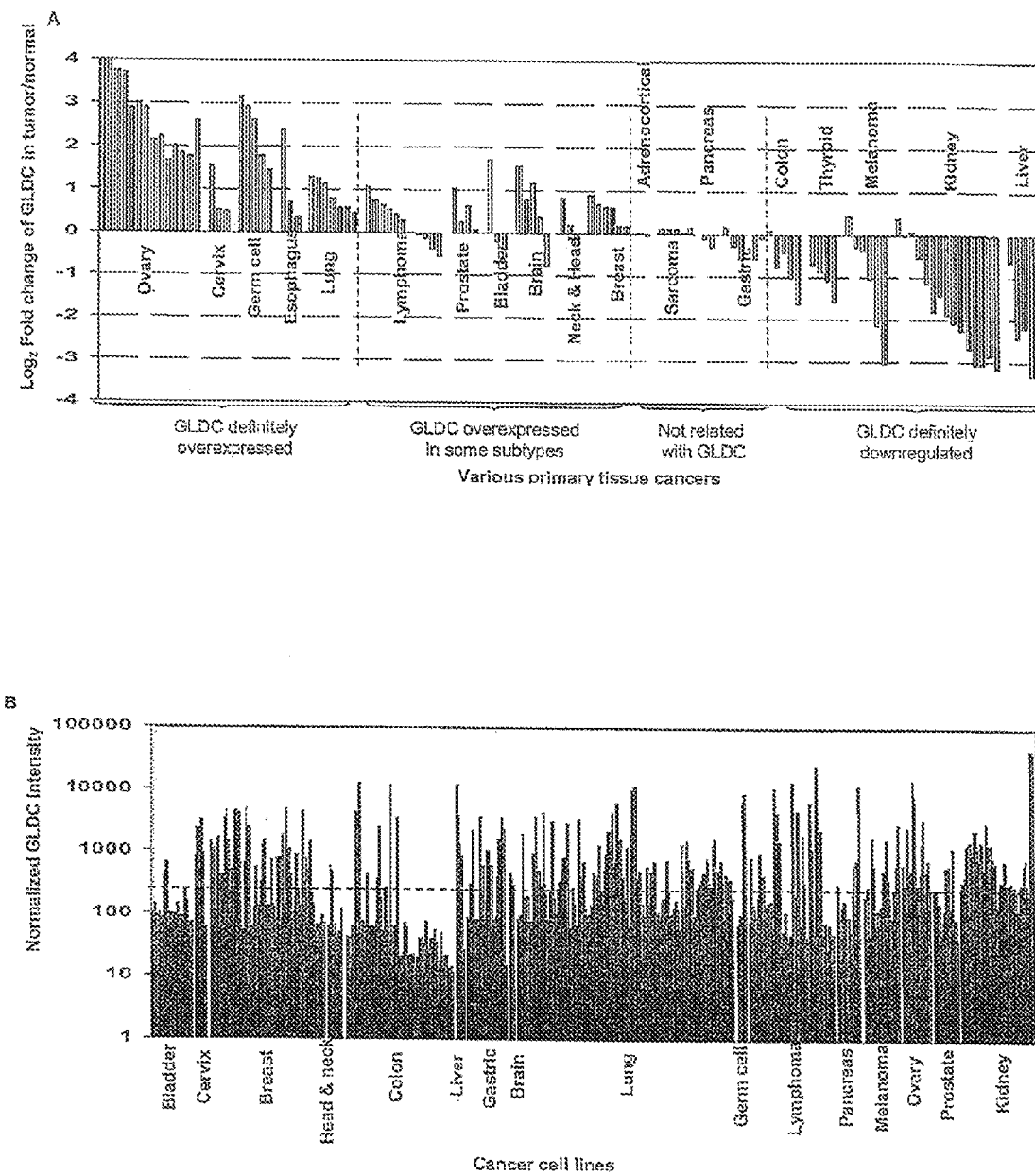

FIG. 2 GLDC expression in human primary cancer samples and cancer cell lines.

(A) Human cancer samples expressing GLDC, as determined by microarray analysis across 2591 of cancer samples and 889 of normal samples. Signal intensity was normalized to signal in tissue-paired normal samples. (B) Human cancer cell lines expressing GLDC, as determined by microarray analysis over 606 various types of cancer cell lines, among which 158 (26.1%) of cancer cell lines show high GLDC expression (intensity >300, above the red line).

Figure 3:
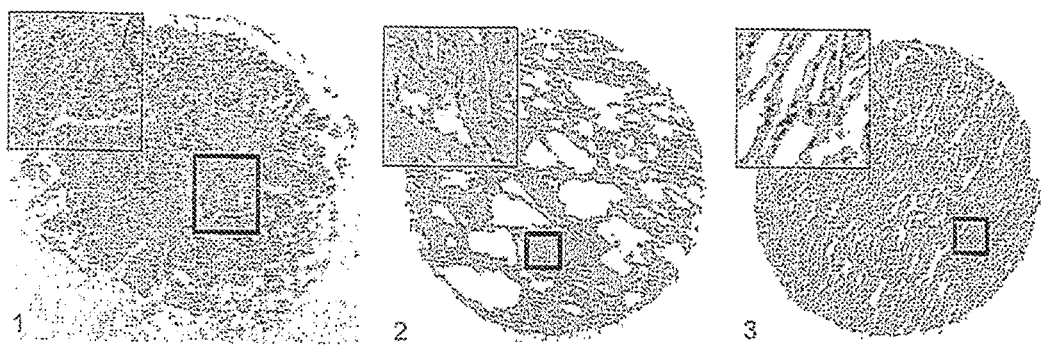

FIG. 3 GLDC expression in lung adenocarcinoma and paired normal lung tissues by immunohistochemistry staining.

Strong expression of GLDC in adenocarcinoma (1) versus low/negative expression in normal lung tissues of bronchioles (2) and alveoli (3) are shown, respectively.

Figure 4:
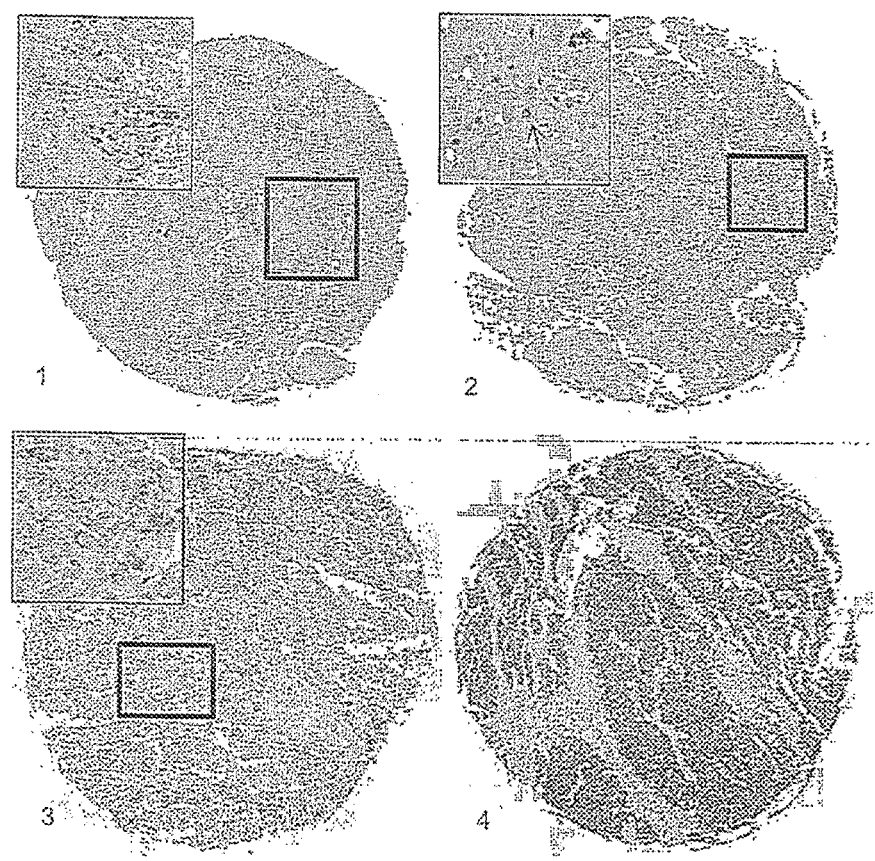

FIG. 4 GLDC expression in other types of lung cancer by immunohistochemistry staining.

Strong expression of GLDC in (1) lung squamous cell carcinoma, (2) lung large cell carcinoma, (3) small cell lung carcinoma and (4) atypical carcinoma are shown.

Figure 5:
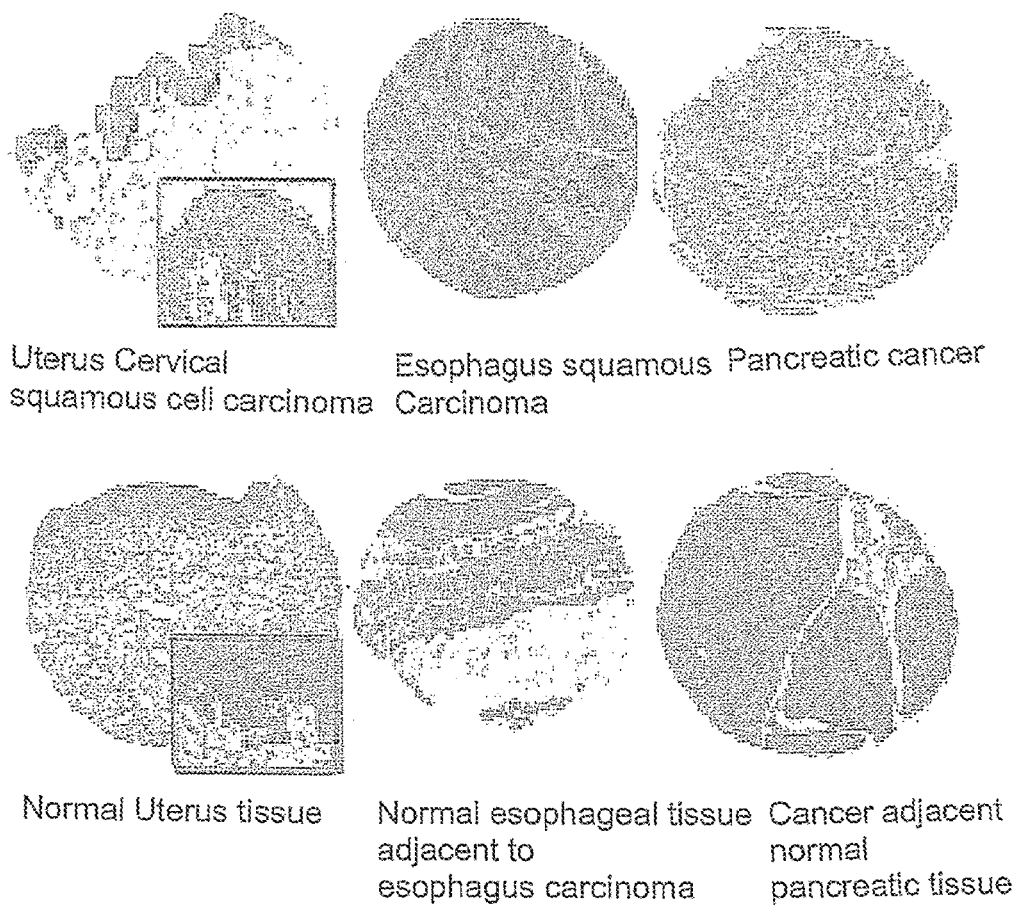
Figure 5:
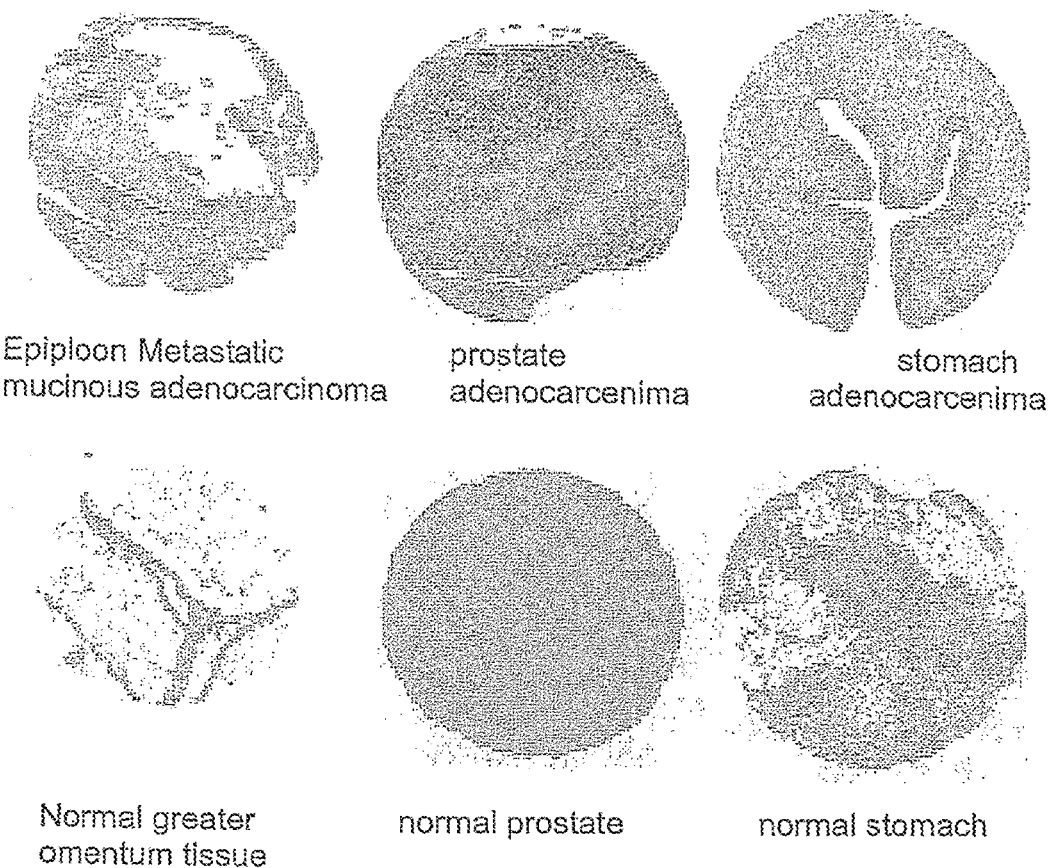

FIG. 5 Screen GLDC expression in various cancers in tissue microarray.

Expression of GLDC in various human cancers versus normal tissues.

Immunohistochemistry staining was applied.

Figure 6:
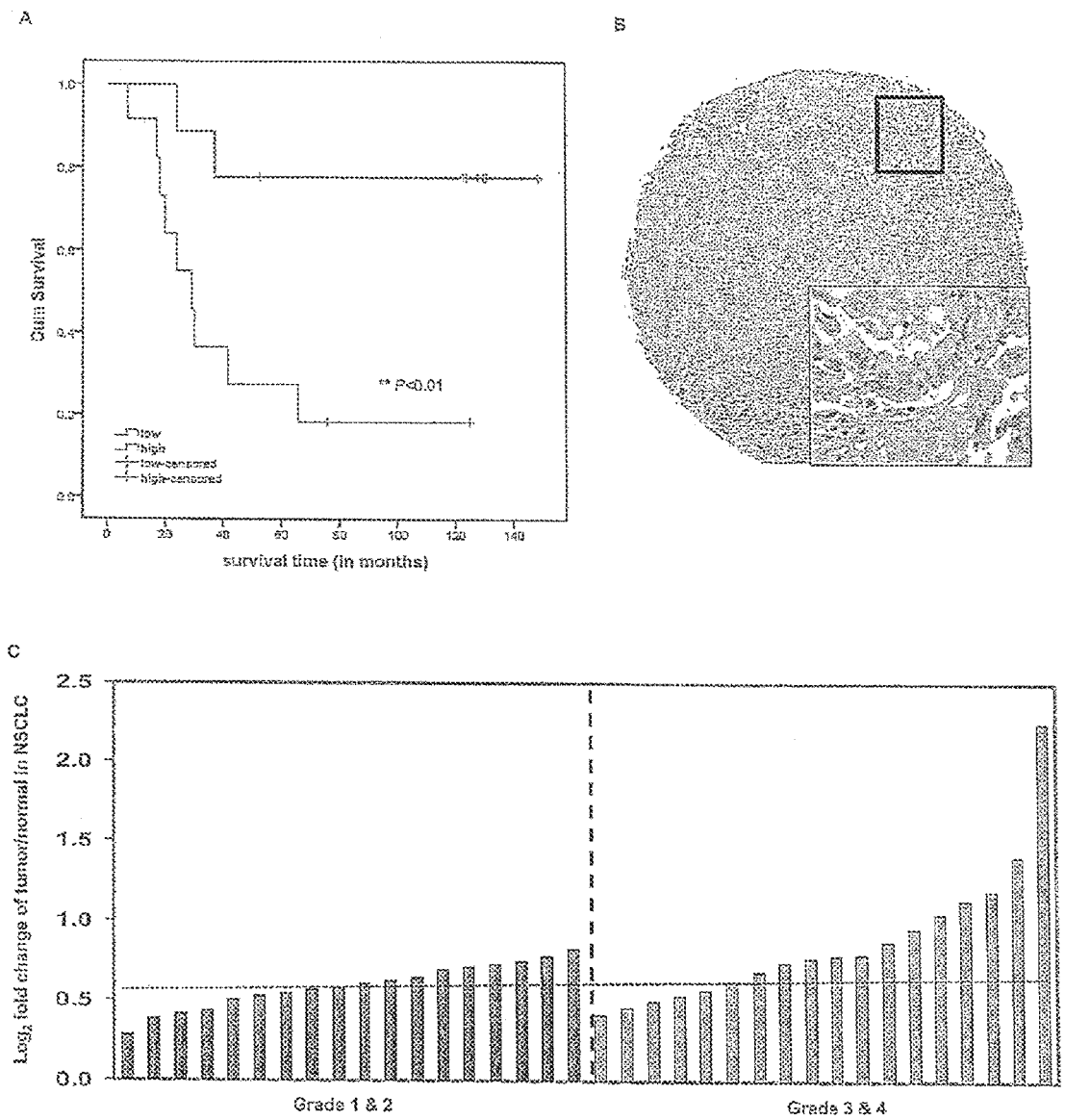

FIG. 6 GLDC is a poor prognosis indicator in human NSCLC.

(A) GLDC expression level is related with poor survival of lung cancer patients. The average survival time is 122±16 months and 46±12 months in low and high expression of GLDC, respectively (n=21). (B) GLDC is an indicator of metastatic lung cancer. GLDC is strongly positive in lymph node from human metastatic lung adenocarcinoma. (C) GLDC expression level in NSCLC from patients varies at different grades (GSE7880, published microarray dataset). The average fold change of tumor/normal in grade 1 & 2 is 1.51 and the average fold change of grade 3 & 4 versus grade 1 & 2 is 1.22, respectively. P<0.05, grade 3 &4 versus grade 1 & 2.

Figure 7:
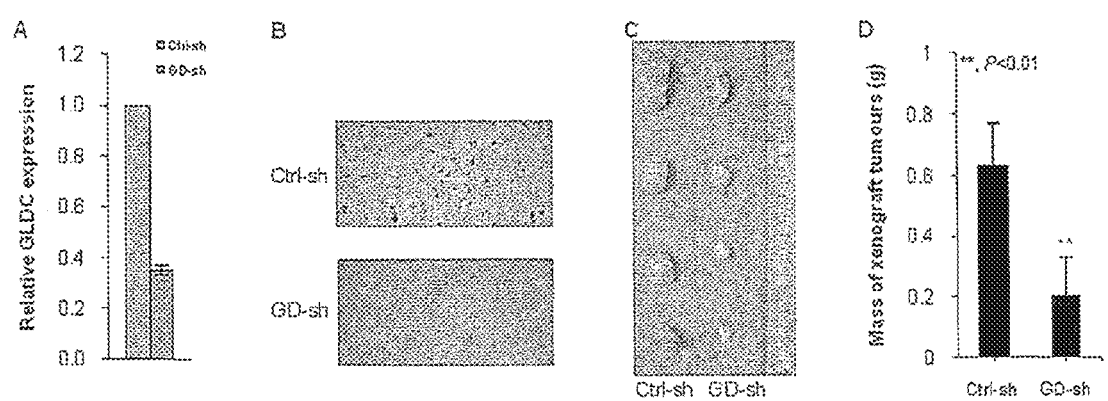

FIG. 7 Knockdown GLDC inhibit the malignant growth of tumorigenic ALCAM$^+$ sphere cells.

(A) Relative expression of GLDC assayed by qRT-PCR in tumor sphere cells (S32) transfected with GLDC shRNA and selected on puromycin.

(B) Colony formation of tumor sphere cells (S32) in soft agar for 30 days by seeding of 1,000 cells per well transfected with GLDC shRNA and selected on puromycin.

(C) Tumor formation of tumor sphere cells (S32) in mice injecting of 100,000 cells per injection transfected with GLDC shRNA and selected on puromycin.

(D) Quantitative mass analysis of xenograft tumor by FIG. 3C. **, P<0.01.

Figure 8:
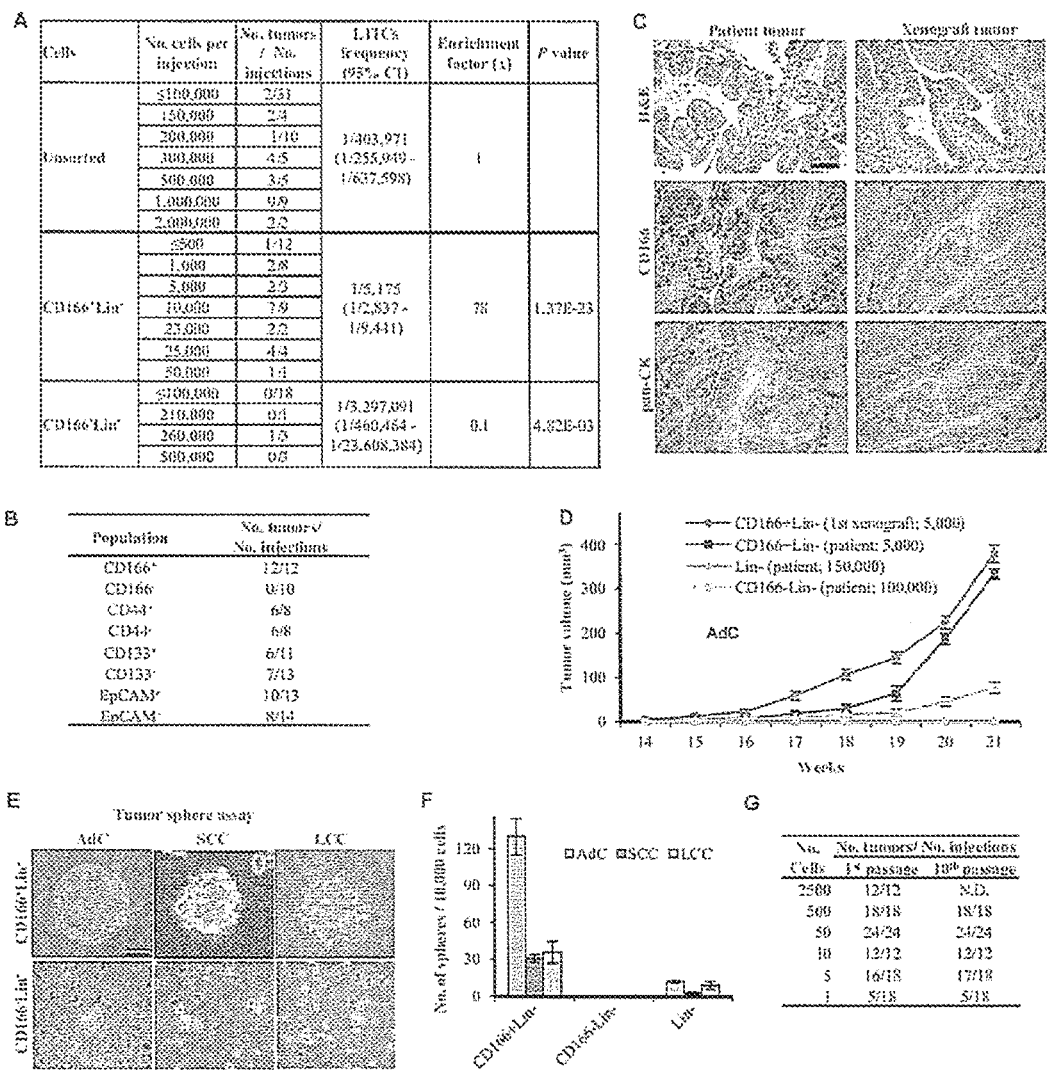

FIG. 8. CD166$^+$ fraction contains tumor initiating cells from NSCLC patients (A) Frequency of tumor-initiating cells (TICs) in unsorted, CD166$^+$ and CD166$^-$ subpopulations of cells from 36 NSCLC patients. CI, confidence interval. Lin$^-$ cells, CD45$^-$ CD31$^-$ cells.

(B) Tumor initiation frequency by various FACS-purified fractions of Lin$^-$ lung cancer cells isolated from primary xenograft tumors shown in (A). $5 \times 10^4$ CD166$^\pm$, CD44$^\pm$, CD133$^\pm$, and EpCAM$^\pm$ cells were tested for tumor initiation in NOD/SCID Il2ry$^{-/-}$ mice (n=12).

(C) Histological analysis of patient tumors and primary xenografts derived from patient tumor CD166$^+$Lin$^-$ lung cancer cells. Tumors were stained for H&E, CD166 and pan-CK (cytokeratin). Scale bar, 50 μm.

(D) Representative tumor-growth curves of xenografts derived from different cell fractions in a lung adenocarcinoma (AdC) patient tumor and the primary xenograft.

(E) Phase-contrast images of tumor spheres seeded with CD166$^+$Lin$^-$ (top) and CD166$^-$ Lin$^-$ (bottom) cells in lung adenocarcinoma (AdC), squamous cell carcinoma (SCC) and large cell carcinoma (LCC). Scale bar, 50 μm.

(F) Quantification of tumor spheres formed by cells from NSCLC patient (AdC, SCC or LCC) CD166$^+$Lin$^-$, CD166$^-$Lin$^-$ and Lin$^-$ populations.

(G) Frequency of tumorigenesis by single patient-derived tumor sphere cells (n=3). N.D., not determined.

In all panels, error bars represent SEM.

Figure 9:
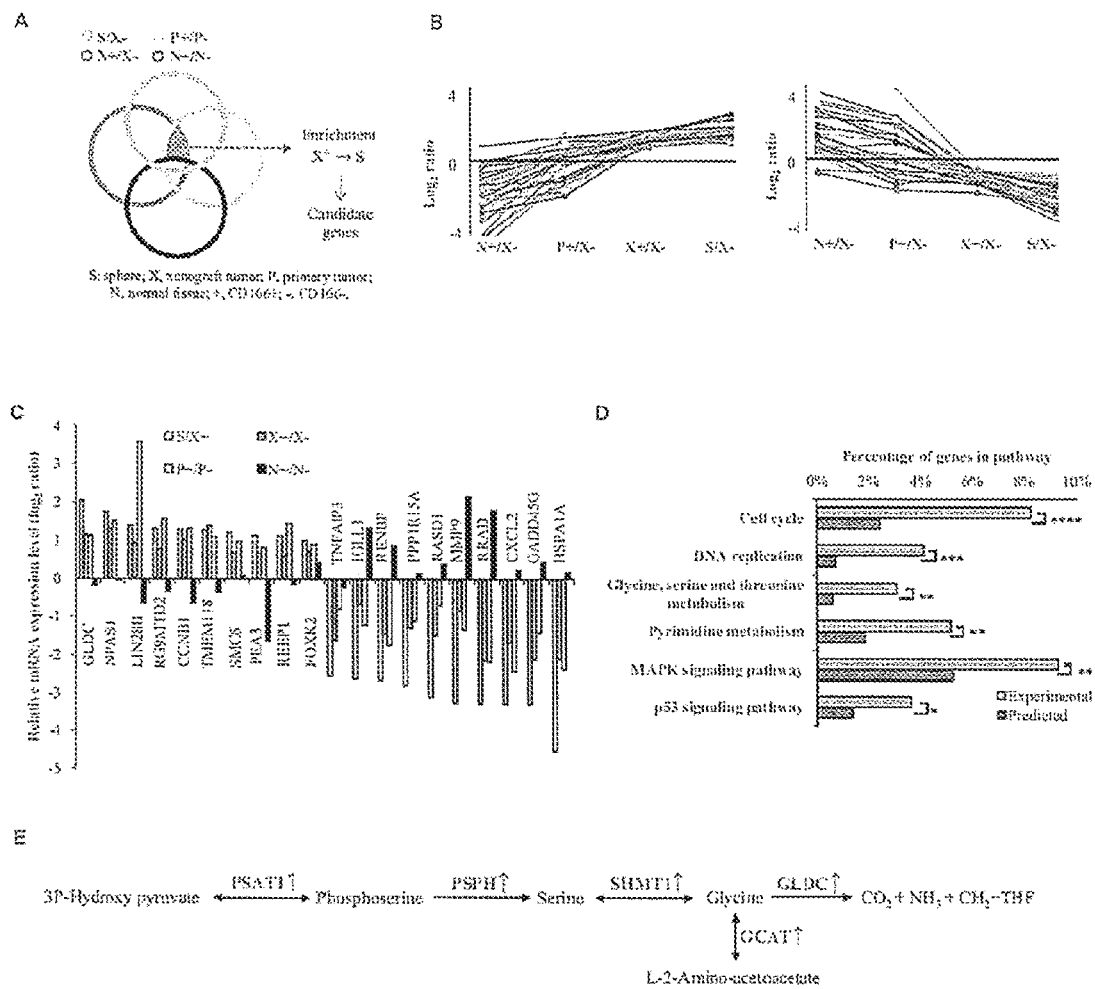

FIG. 9. Lung TICs express high levels of GLDC and LIN28B (A) Venn diagram showing strategy for enriching tumorigenic-gene expression profile by genome-wide transcriptome analysis. A list of the differentially-expressed genes (cutoff threshold of 1.5-fold, P<0.05) common between P+ vs. P−, X+ vs. X− and S vs. X− was derived, with the differentially-expressed genes of N+ vs. N− excluded. The gene list was further filtered to select only genes further upregulated or downregulated in S vs. X+. N, normal lung tissue (n=3); P, patient tumor (n=1); S, tumor sphere (n=4); X, xenograft tumor (n=3); +, CD166$^+$; −, CD166$^-$. Total n=11.

(B) Graphs of relative expression of candidate lung TIC-associated genes in increasing (left, n=194) or decreasing (right, n=295) trends across different CD166$^+$ fraction cells from normal lung tissue (N), primary tumor (P), xenograft tumor (X) and tumor spheres (S) versus non-tumorigenic CD166$^-$ (X−) cells.

(C) Top ranked genes differentially expressed in lung TICs. (D) Enrichment of KEGG pathways by genes differentially expressed in lung TICs. * P<0.05,  P<0.01, * P<0.001, **** P<0.0001.

(E) Schematic diagram of glycine, serine and threonine metabolism genes significantly (P<0.05) upregulated in lung TICs. ↑, upregulation.

Figure 10:
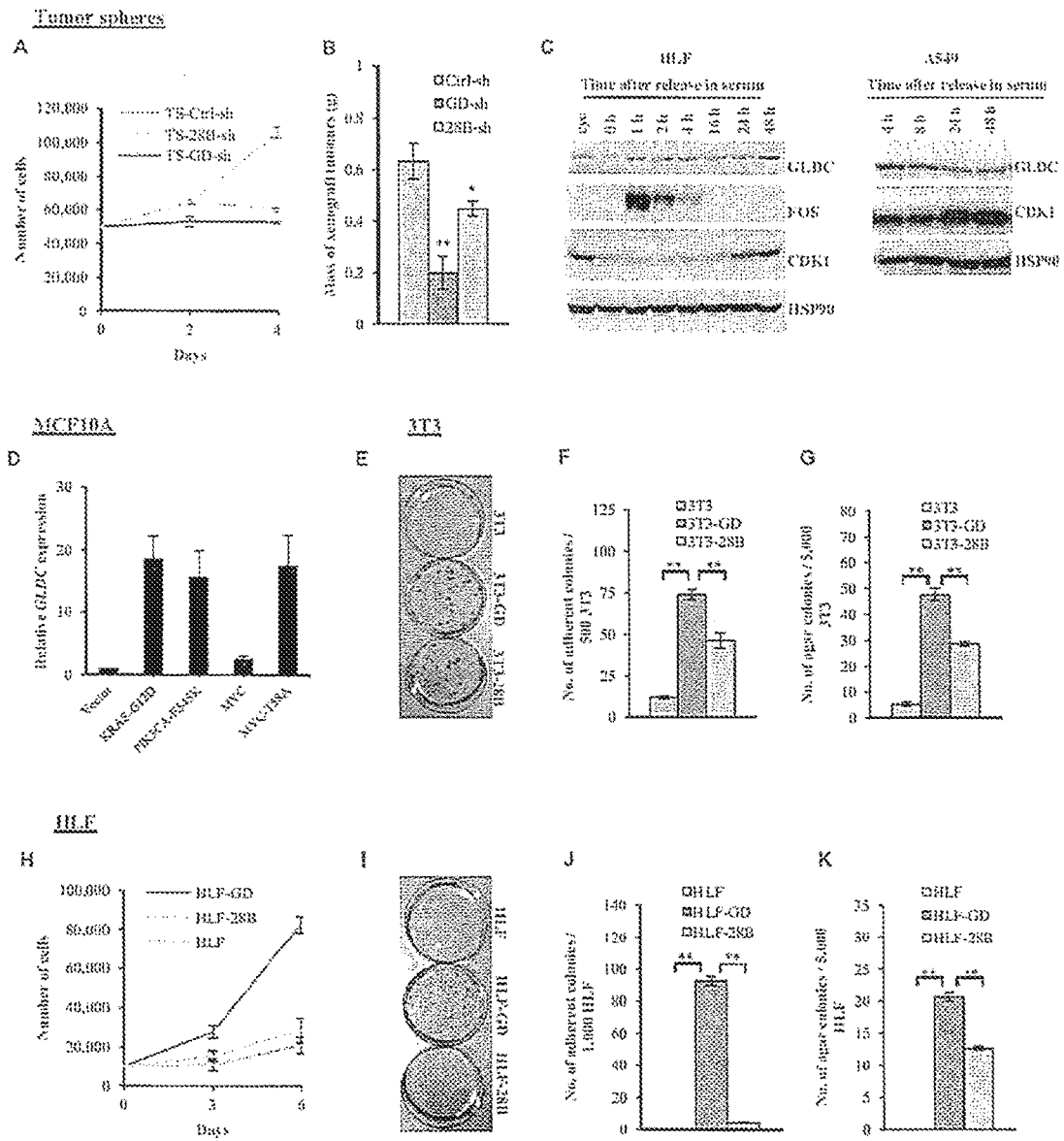

FIG. 10. GLDC and LIN28B are necessary and sufficient for malignant growth (A) Proliferation curve of tumor sphere (TS) cells with shRNA knockdown of either GLDC (GD-sh) or LIN28B (28B-sh).

(B) Quantitative mass analysis of xenograft tumors formed 30 days after transplanting 100,000 tumor sphere cells with either GLDC knockdown (GD-sh) or LIN28B knockdown (28B-sh).

(C) Western blot analysis of endogenous GLDC during the cell-cycle in synchronized normal human lung fibroblasts (HLF) and transformed A549 cells. HLF or A549 cells were serum-starved for 72 hours followed by release into serum-containing medium with samples collected at indicated time points. Expression of GLDC, FOS (early serum response) and CDK1 (E2F target) were tested. Normal growing, unsynchronized cells (Cyc) were used as a control. HSP90 was used as a loading control. CDK1, cyclin dependent kinase 1; HSP90, heat shock protein 90.

(D) Expression of endogenous GLDC in MCF10A cells transformed by oncogenic $KRAS^{G12D}$, $PIK3CA^{E54K}$, MYC or $MYC^{T58A}$, by qRT-PCR.

(E) Colony formation assay in adherent conditions by seeding 500 3T3 cells overexpressing either GLDC (3T3-GD) or LIN28B (3T3-28B).

(F) Quantitative analysis of colony formation efficiency under adherent conditions as shown in (E).

(G) Quantitative analysis of soft agar colony formation by 5000 3T3 cells overexpressing either GLDC (3T3-GD) or LIN28B (3T3-28B). Colonies were stained with INT on day 28.

(H) Proliferation curve of HLF cells overexpressing GLDC (HLF-GD), LIN28B (HLF-28B) or the empty vector (HLF).

(I) Colony formation assay in adherent conditions seeding 1000 HLF cells overexpressing GLDC (HLF-GD), LIN28B (HLF-28B) or the empty vector (HLF).

(J) Quantitative analysis of colony formation efficiency under adherent conditions as shown in (I).

(K) Quantitative analysis of soft agar colony formation by 5000 HLF cells overexpressing either GLDC (HLF-GD), LIN28B (HLF-28B) or the empty vector (HLF).

(L) Tumor formation by CD166⁻ lung tumor cells 3 months after overexpression of GLDC. CD166⁻ tumor cells from xenografts were sorted by FACS and infected with retrovirus expressing either the empty vector (CD166⁻) or GLDC (CD166⁻ GD), followed by transplantation into mice 24 h after infection (n=12 for each group).

In all panels, error bars represent SEM. *P<0.05, ** P<0.01.

Figures 10, 11:
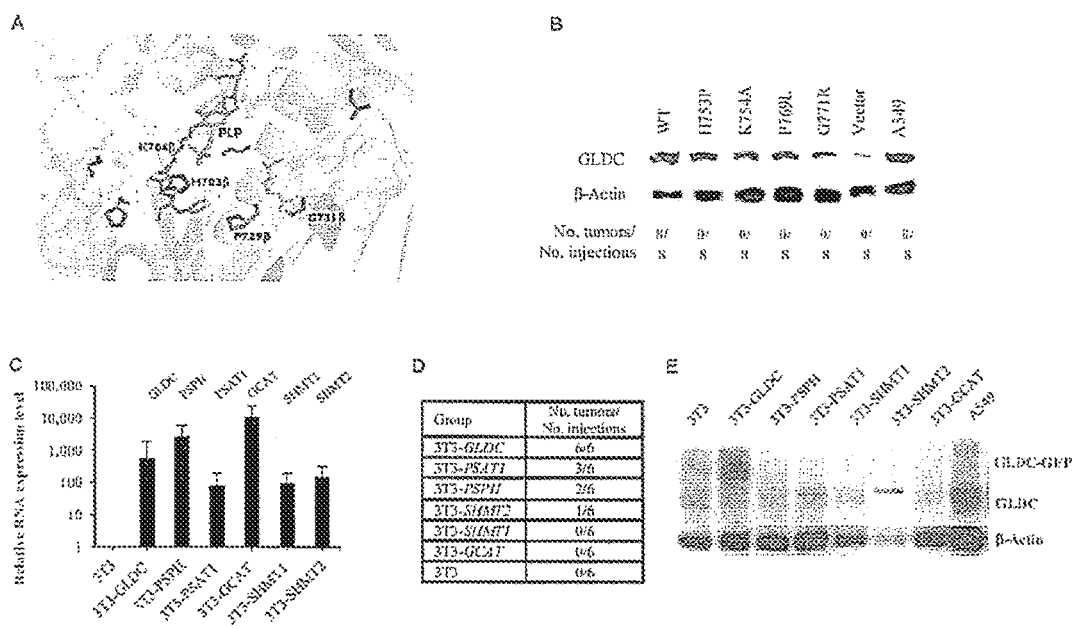

FIG. 11. GLDC promotes tumorigenesis through its metabolic activity (A) Crystal structure of *T. thermophilus* GLDC near the catalytic active site. The labeled bacterial residues H703β, K704β (purple), P729β and G731β□□ are homologous to H753, K754, P769 and G711 of human GLDC. Residues implicated in human non-ketotic hyperglycinemia are shown (red). PLP, pyridoxal-5'-phosphate cofactor (green).

(B) GLDC protein expression and tumor formation efficiency of 3T3 cells overexpressing wild-type or mutant GLDC. Four point mutations were tested: H753P, K754A, P769L and G771R. Incidence of tumor formation was determined 2 months after injection with 1.5×10⁶ cells per mouse (n=8). A549 cells served as a positive control. WT, wild-type.

(C) Gene expression in 3T3 cells overexpressing GLDC, PSPH, PSAT1, GCAT, SHMT1 and SHMT2, relative to 3T3 cells with the empty vector, as determined by qRT-PCR.

(D) Tumor formation efficiency of 3T3 cells overexpressing GLDC, PSPH, PSAT1, GCAT, SHMT1, SHMT2 or the empty vector. Incidence of tumor formation was determined 2 months after injection with 1.5×10⁶ cells per mouse (n=6).

(E) GLDC protein expression of 3T3 cells overexpressing GLDC, PSPH, PSAT1, GCAT, SHMT1 and SHMT2. A549 cells served as a positive control. β-actin was used as a loading control.

Figure 12:
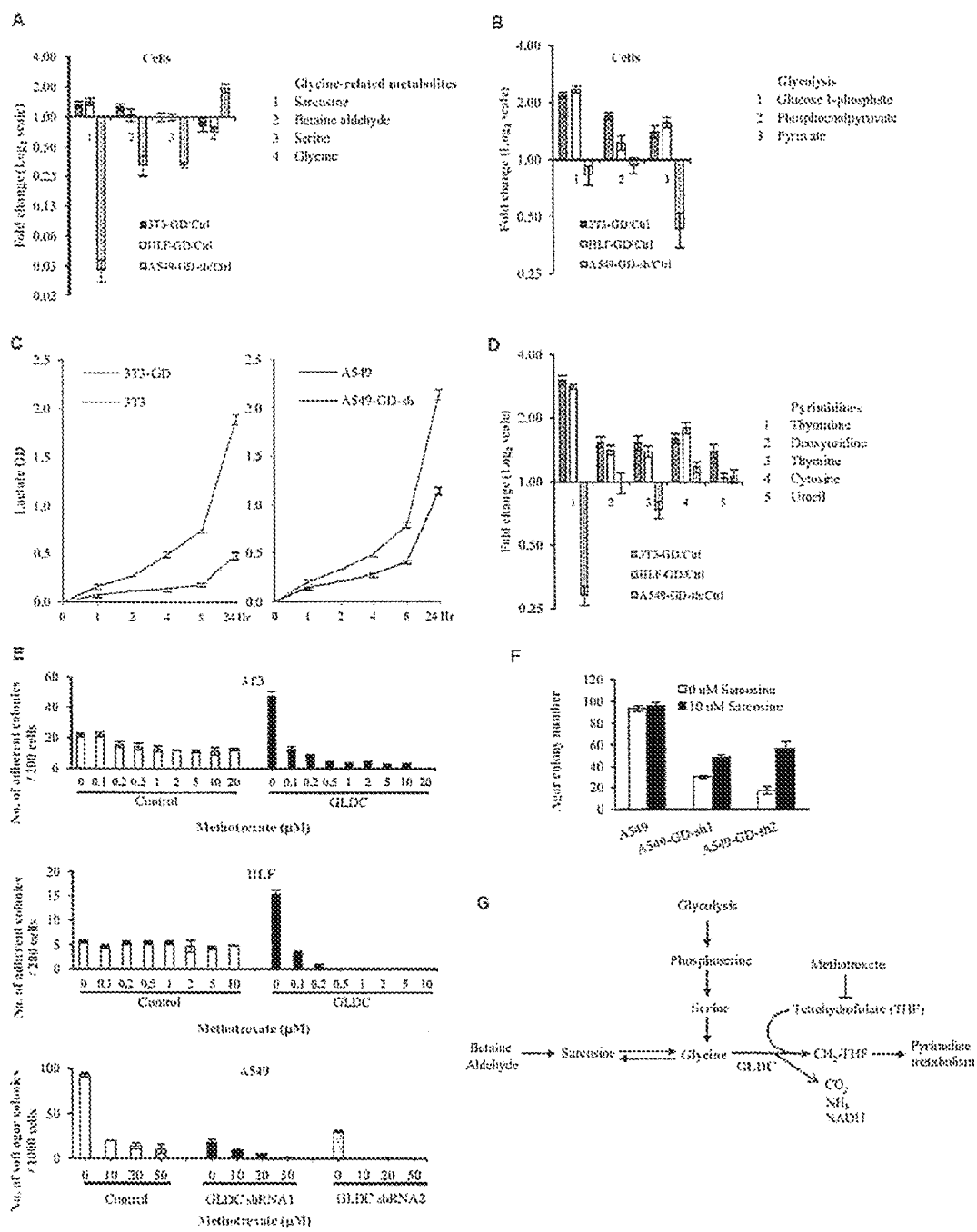

FIG. 12. Metabolomics of cells upon GLDC overexpression and knockdown (A-D) Relative fold change in levels of (A) glycine-related metabolites, (B) glycolysis intermediates, and (D) pyrimidines in 3T3 cells with GLDC overexpression (3T3-GD/Ctrl), HLF cells with GLDC overexpression (HLF-GD/Ctrl) and A549 cells with GLDC knockdown (A549-GD-sh/Ctrl), as determined by LC-MS metabolomics. (C) Lactate production by 3T3 cells with GLDC overexpression or A549 cells with GLDC knockdown.

(E) Effects of the anti-folate drug methotrexate on colony formation after GLDC overexpression or knockdown. 3T3 and HLF cells overexpressing GLDC were plated at clonal density and exposed to varying concentrations of methotrexate for 8 days. A549 cells with GLDC knockdown were plated in soft agar at clonal density and exposed to varying concentrations of methotrexate for 14 days.

(F) Effects of sarcosine on soft agar colony formation after GLDC knockdown in A549 cells. 1000 cells were seeded in soft agar at clonal density and exposed to 10 µM sarcosine for 14 days.

(G) Model of metabolic flux changes induced by GLDC.

In all panels, error bars represent SEM.

Figure 13:
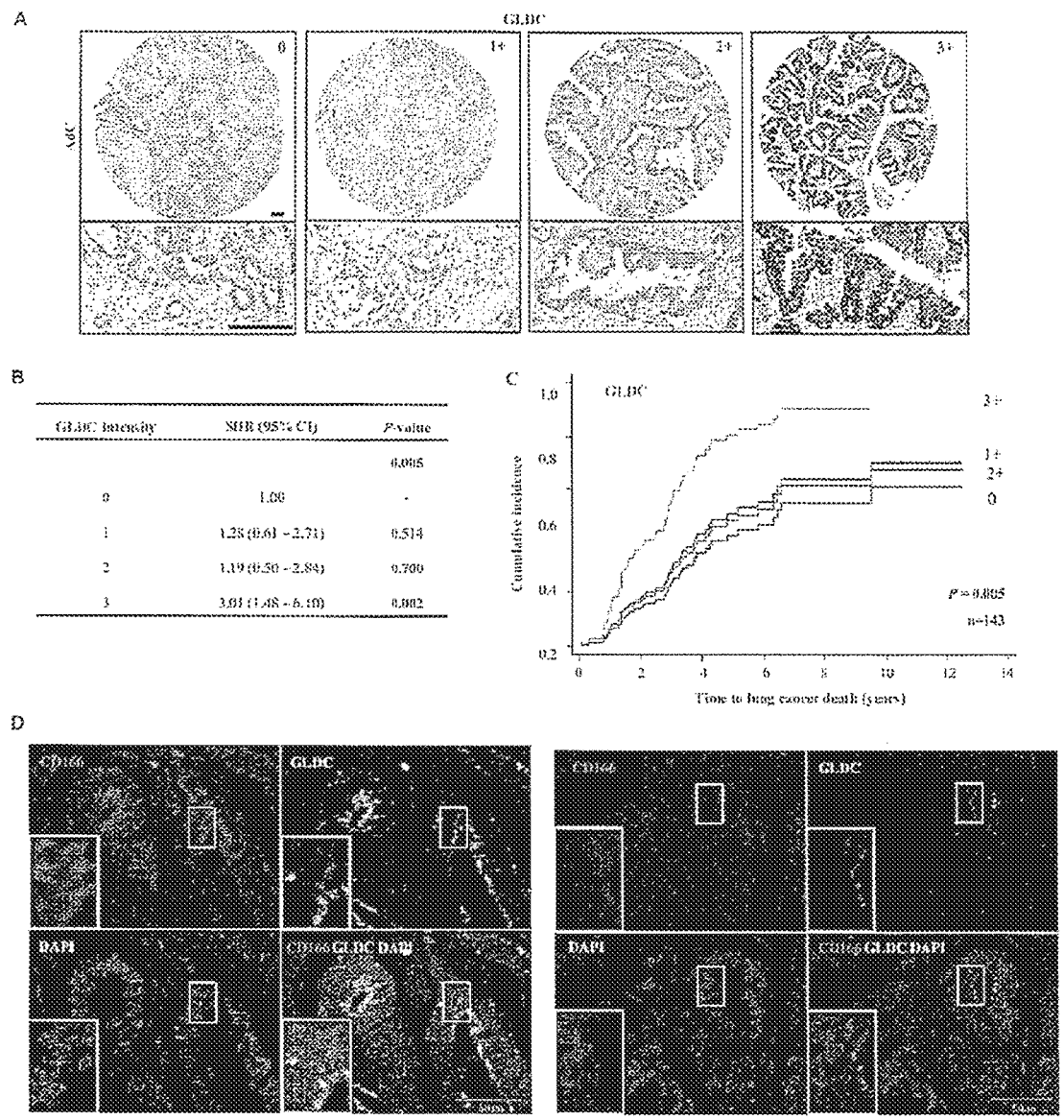

FIG. 13. GLDC is a prognostic indicator for mortality in NSCLC patients (A) GLDC immunohistochemistry staining in a NSCLC tumor microarray (n=143). Representative images shown for human primary lung adenocarcinomas (AdC) immunostained with GLDC. Staining intensity grade is indicated in the upper right corner. The boxed region in the upper images is shown at higher magnification in the lower image. Scale bar, 100 µm.

(B) Subdistribution hazard ratios for each GLDC staining intensity grade, adjusted for American Joint Committee on Cancer (AJCC) staging. CI, confidence interval.

(C) Cumulative incidence of lung cancer mortality adjusted for AJCC staging, for patients with each GLDC staining intensity grade.

(D) Co-immunofluorescence staining of CD166 (red) and GLDC (green) on primary lung cancer patient tumors, counterstained with DAPI (blue). Representative cases with co-expression of high levels of CD166 and high levels of GLDC (left panel), and low levels of CD166 and low level of GLDC (right panel) are shown. Higher magnification inset is shown in bottom left corner. Scale bar, 50 µm.

Figure 14:
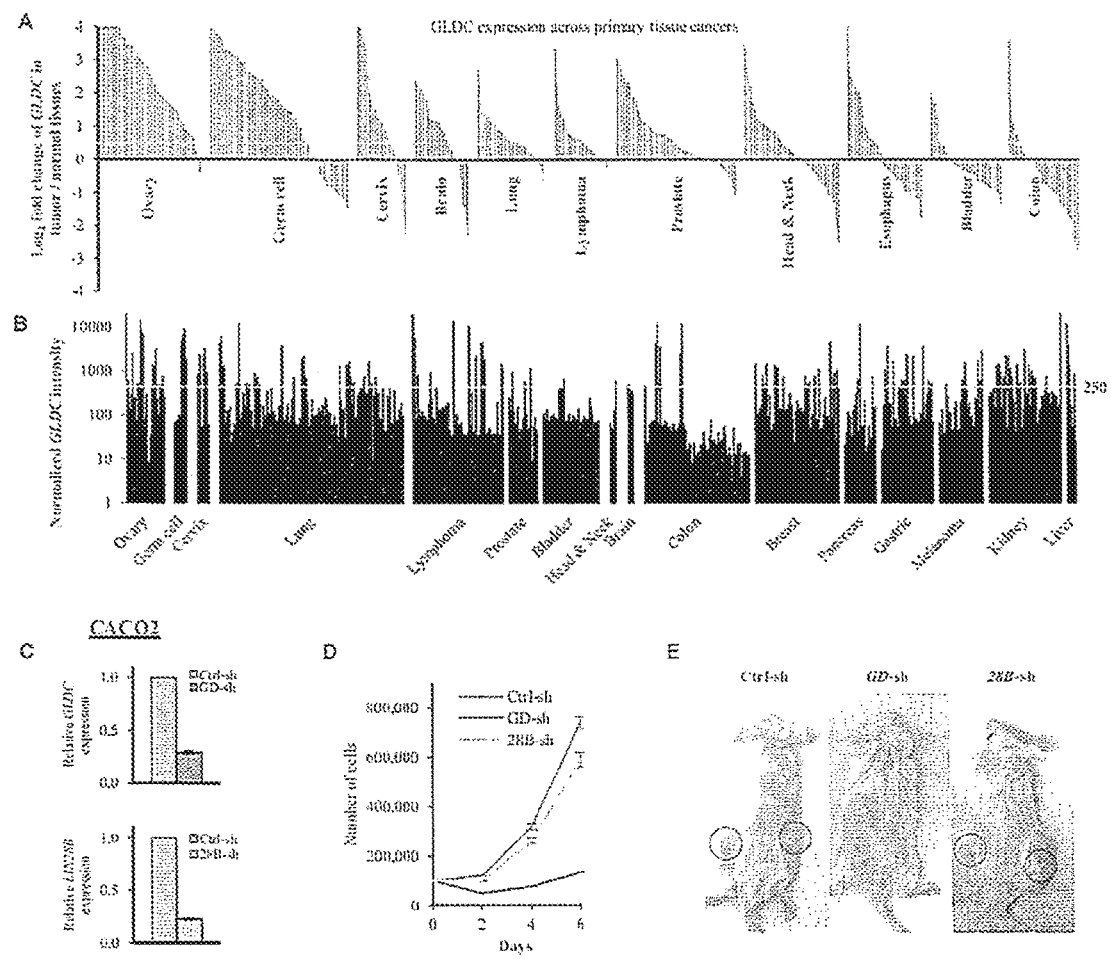

FIG. 14. GLDC is aberrantly expressed in other cancers.

(A) Log₂-transformed fold changes in GLDC expression of patient tumors vs. normal adjacent tissues across different cancers. Data is normalized and aggregated from 51 GEO data sets containing 84 sets of tumor expression data (tumor vs. normal) with 2020 tumor samples and 671 normal samples. Fold change cutoff was set at 1.5 by yellow line.

(B) Normalized GLDC expression across various cancer cell lines (n=606). Yellow line indicates the mean value (250) of GLDC expression intensities between patient lung tumors and normal lung tissues.

(C) qRT-PCR for GLDC and LIN28B in CACO2 colon cancer cells expressing shRNA against GLDC (GD-sh) or LIN28B (28B-sh).

(D) Proliferation curve of CACO2 cells expressing shRNA against GLDC (GD-sh) or LIN28B gene (28B-sh) described in (C). Cell numbers were measured on day 2, 4 and 6.

(E) Tumor formation in mice upon injecting $2.5 \times 10^4$ CACO2 colon cancer cells with GLDC knockdown (CACO2-GD-sh) or LIN28B knockdown (CACO2-28B-sh). Mice were assessed by week 13 (n=6).

In all panels, error bars represent SEM.

Figure 15:
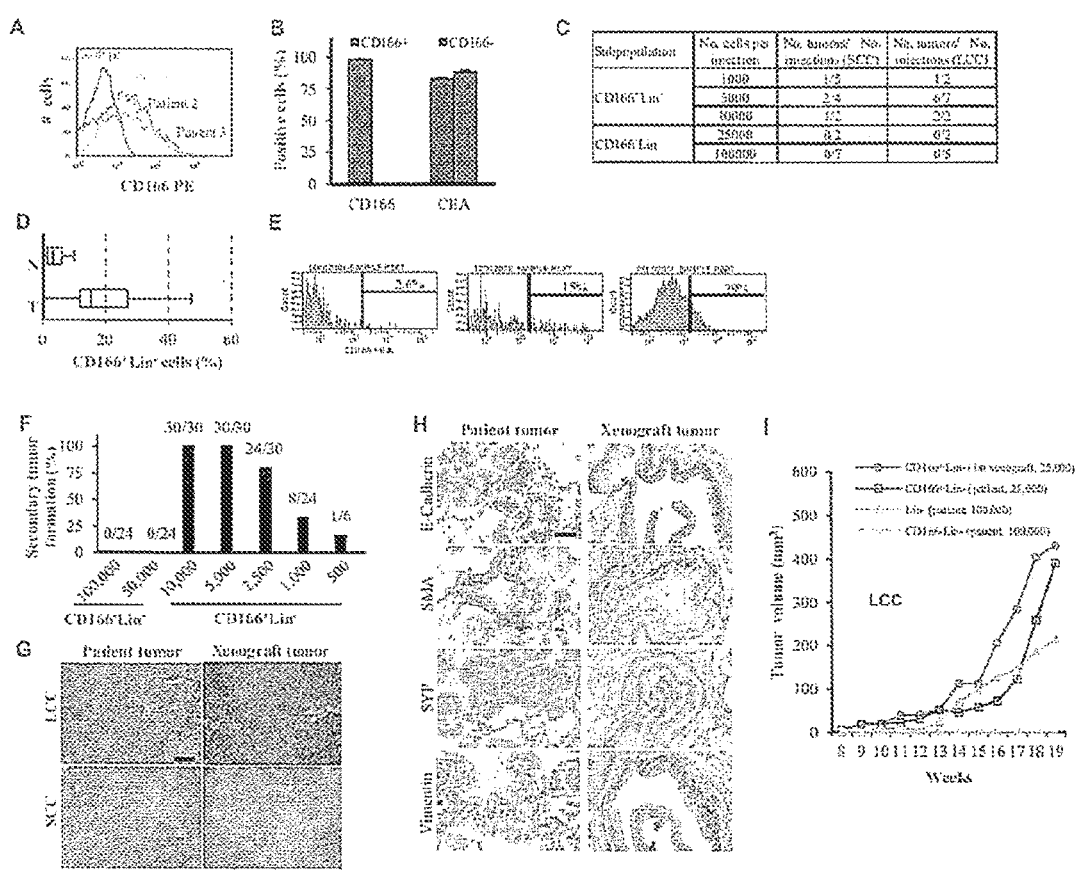
Figure 15:
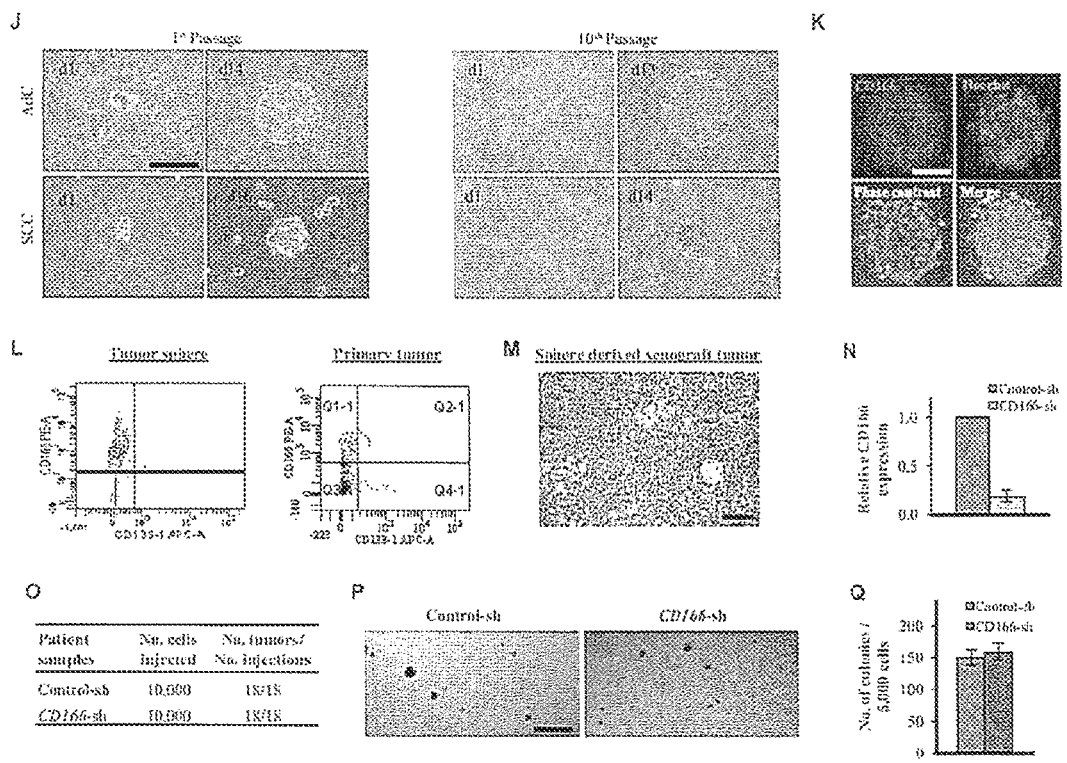

FIG. 15. Characterization of lung tumor initiating cells from NSCLC patients, (A) CD166 profile of tumor cells from 3 representative NSCLC patients by FACS. See also Table 3.

(B) FACS analysis of carcinoembryonic antigen in CD166+ and CD166− lung tumor cells (n=4).

(C) Tumor formation by CD166+ vs. CD166− cells in squamous cell carcinoma (SCC; n=4) and large cell carcinoma (LCC; n=2).

(D) Frequency of CD166+ cells in lung tumors (T, n=24) vs. adjacent normal lung tissues (N, n=13). Box plots show $75^{th}$ and $25^{th}$ percentiles (ends of boxes), and the median frequency (band within box) of CD166+ cells.

(E) Frequency of CD166+ cells (2.6% to 29%) from FACS analysis of 3 primary tumors.

(F) Secondary tumor initiation from primary xenograft tumor cells (n=4 patients).

(G) H&E staining of primary tumors and CD166+-derived xenografts. Scale bar, 100 μm.

(H) Expression of E-cadherin, smooth muscle actin, synaptophysin and vimentin by immunohistochemistry in tumors and CD166+-derived tumors. Scale bar, 50 μm.

(I) Tumor growth curves of xenografts derived from different cell fractions of a LCC tumor and the primary xenograft (n=3).

(J) NSCLC derived lung tumor spheres. Single tumor cells formed spheres in 14-16 days that can be serially passaged. Scale bar, 50 μm.

(K) Staining of tumor spheres for CD166 (red) and Hoechst (blue). Scale bar, 50 μm.

(L) FACS plot for CD166 and CD133 expression in primary tumor and tumor spheres.

(M) H&E staining of xenograft tumor from adenocarcinoma-derived tumor sphere cells. Scale bar, 50 μm.

(N) CD166 expression by qRT-PCR in tumor spheres with and without CD166 shRNA knockdown (n=3).

(O) Tumor formation by tumor spheres with and without CD166 knockdown evaluated after 60 days (n=3).

(P) Day 28 soft agar colony formation by 5000 tumor spheres with and without CD166 knockdown. Scale bar, 300 μm.

(Q) Counting of soft agar colonies shown in (P) (n=3).

In all panels, error bars represent SEM.

Figure 16:
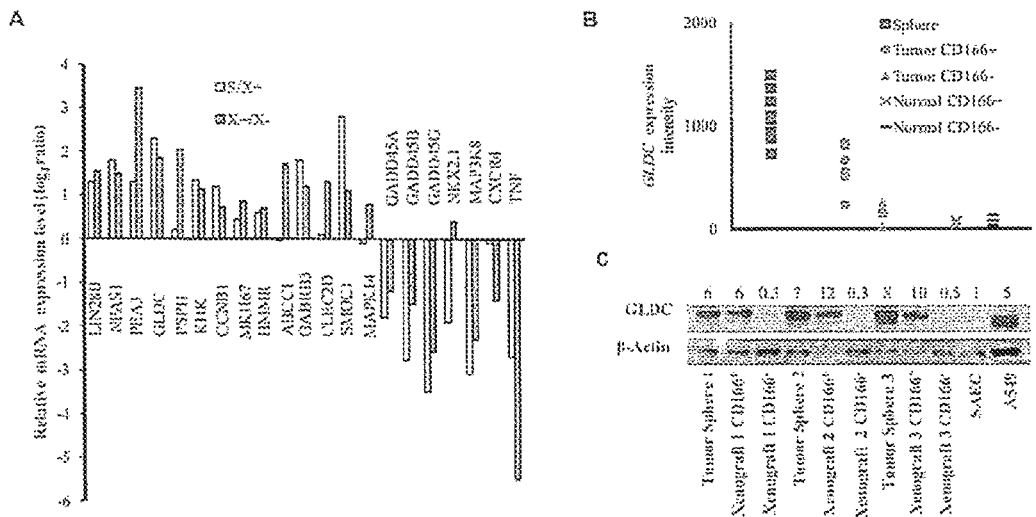
Figure 16:
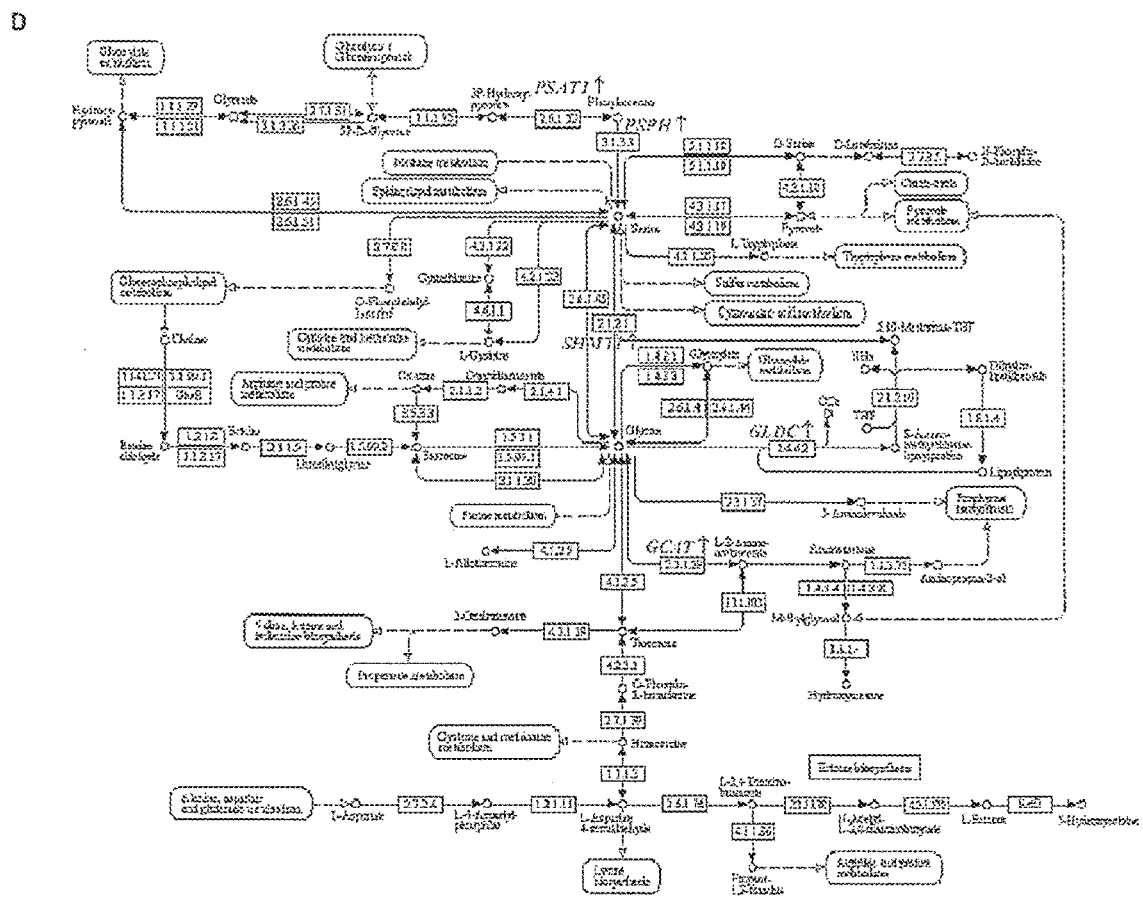

FIG. 16. Gene expression signature of lung TICs, (A) Validation of top candidate genes associated with lung TICs by qRT-PCR, normalized to GAPDH.

(B) GLDC mRNA expression in tumor spheres, tumor CD166+, tumor CD166−, normal CD166+ and normal CD166− cells by microarray analysis (total n=11).

(C) GLDC protein expression in tumor sphere, tumor CD166+, and tumor CD166− cells from 3 different patients, by Western blot. Normal SAEC cells served as negative controls, A549 cells served as positive controls, and β-actin served as a loading control. GLDC signal for each sample was quantified by ImageJ and normalized to the β-actin signal, relative to SAEC cells. SAEC, small airway epithelial cells.

(D) KEGG pathway of glycine, serine and threonine metabolism. Metabolic genes upregulated in lung TICs are indicated.

Figure 17:
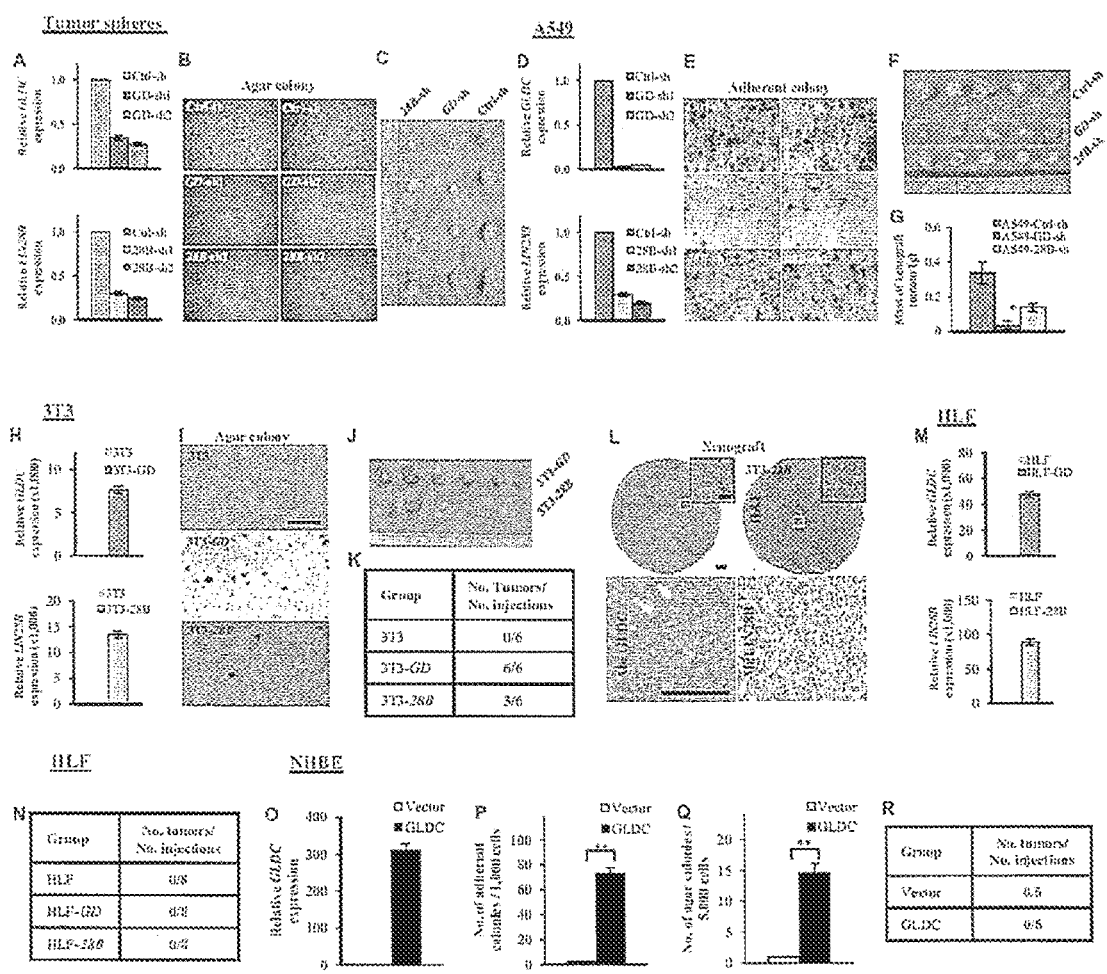

FIG. 17. GLDC overexpression and knockdown in vitro, (A-C) Gene expression of GLDC and LIN28B (A), soft agar colony formation by seeding 1000 cells (B) and tumor formation in mice upon injecting $1 \times 10^5$ cells (C) from human lung tumor spheres with and without shRNA against GLDC (GD-sh1/2) or LIN28B (28B-sh1/2).

(D-G) Gene expression of GLDC and LIN28B (D), adherent colony formation by seeding 100 cells (E), tumor formation in mice upon injecting $1 \times 10^6$ cells (F) and quantitative mass analysis of xenograft tumors (G) from A549 cells with and without shRNA against GLDC (GD-sh1/2) or LIN28B (28B-sh1/2).

(H-L) Gene expression of GLDC and LIN28B (H), soft agar colony formation by seeding 5000 cells (I), tumor formation in mice upon injecting $1.5 \times 10^6$ cells (n=6) (J), tumor formation efficiency in mice (n=6) (K) and histological analysis of xenograft tumors stained for H&E, GLDC and LIN28B from NIH/3T3 overexpressing GLDC (3T3-GD), LIN28B (3T3-28B) or the empty vector (3T3) (L). Scale bar, 300 μm (I), 20 μm for inset and 100 μm in full images (L).

(M and N) Gene expression of GLDC and LIN28B (M) and tumor formation efficiency in mice transplanted with $2 \times 10^6$ cells, assessed up to 6 months post-injection (n=8) (N) in normal human lung fibroblasts (HLF) overexpressing GLDC (HLF-GD), LIN28B (HLF-28B) or the empty vector (HLF).

(O-R) GLDC gene expression (O), quantitative analysis of adherent colony formation by seeding 1000 cells (P) and soft agar colony formation by seeding 5000 cells (n=3) (Q), tumor formation efficiency in mice transplanted with $1 \times 10^6$, assessed 2 months post-injection (n=6) (R) by normal human bronchial epithelial cells (NHBE) overexpressing GLDC or the empty vector.

In all panels, error bars represent SEM. *P<0.05, **P<0.01.

Figure 18:
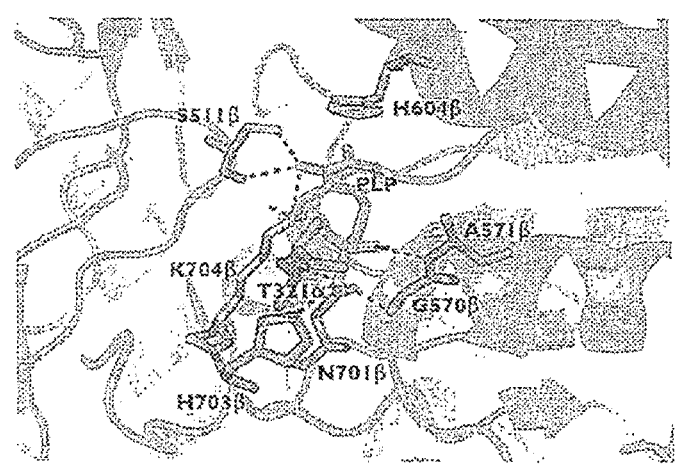

FIG. 18 Sequence alignment and active site residues of GLDC (A) Amino acid sequence alignment of *T. thermophilus* (SEQ ID NO: 69) and human GLDC. (SEQ ID NO: 2), start of the β chain of *T. thermophilus* GLDC. Black, conserved residues. Grey, residues with similar chemical properties. Red, active site residues of human GLDC mutated by site-directed mutagenesis to generate H753P, K754A, P769L and G771R mutants.

(B) Active site residues of *T. thermophilus* GLDC (blue) and the pyridoxal-5'-phosphate cofactor (PLP, green).

Figure 19:
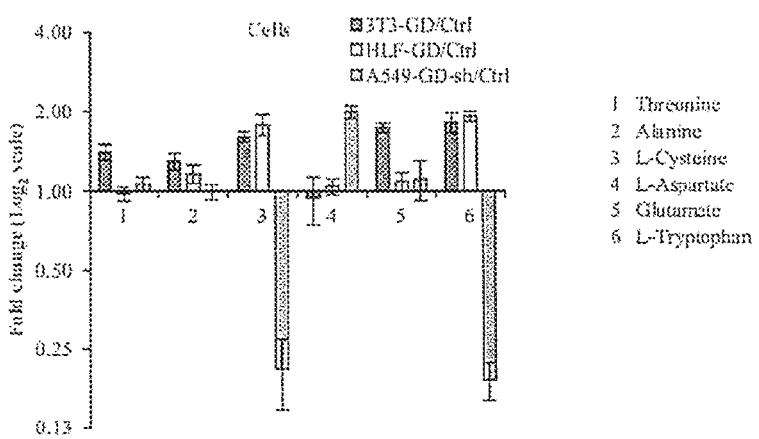
Figure 19:
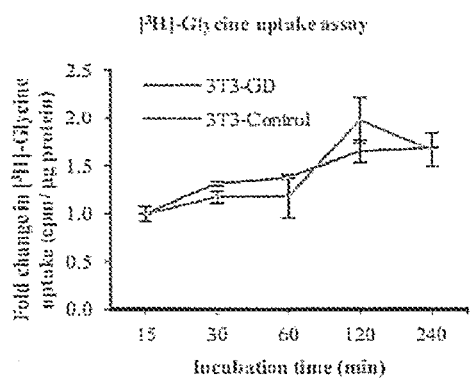
Figure 19:
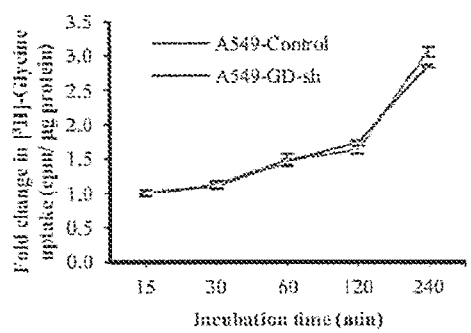

FIG. 19 Metabolic changes after GLDC overexpression and knockdown (A) Relative fold change in levels of amino acids in 3T3 cells with GLDC overexpression (3T3-GD/Ctrl), HLF cells with GLDC overexpression (HLF-GD/Ctrl) and A549 cells with GLDC knockdown (A549-GD-sh/Ctrl), as determined by LC-MS metabolomics.

(B and C) Time course of [$^3$H]-glycine uptake in 3T3 cells overexpressing GLDC (B) or A549 cells with GLDC knockdown (C), incubated at 37° C. with [$^3$H]-glycine ($2.22 \times 10^4$ cpm in 2 ml of media). No significant changes in [$^3$H]-glycine uptake were observed with either GLDC overexpression (B) or knockdown (C).

In all panels, error bars represent SEM.

Figure 20:
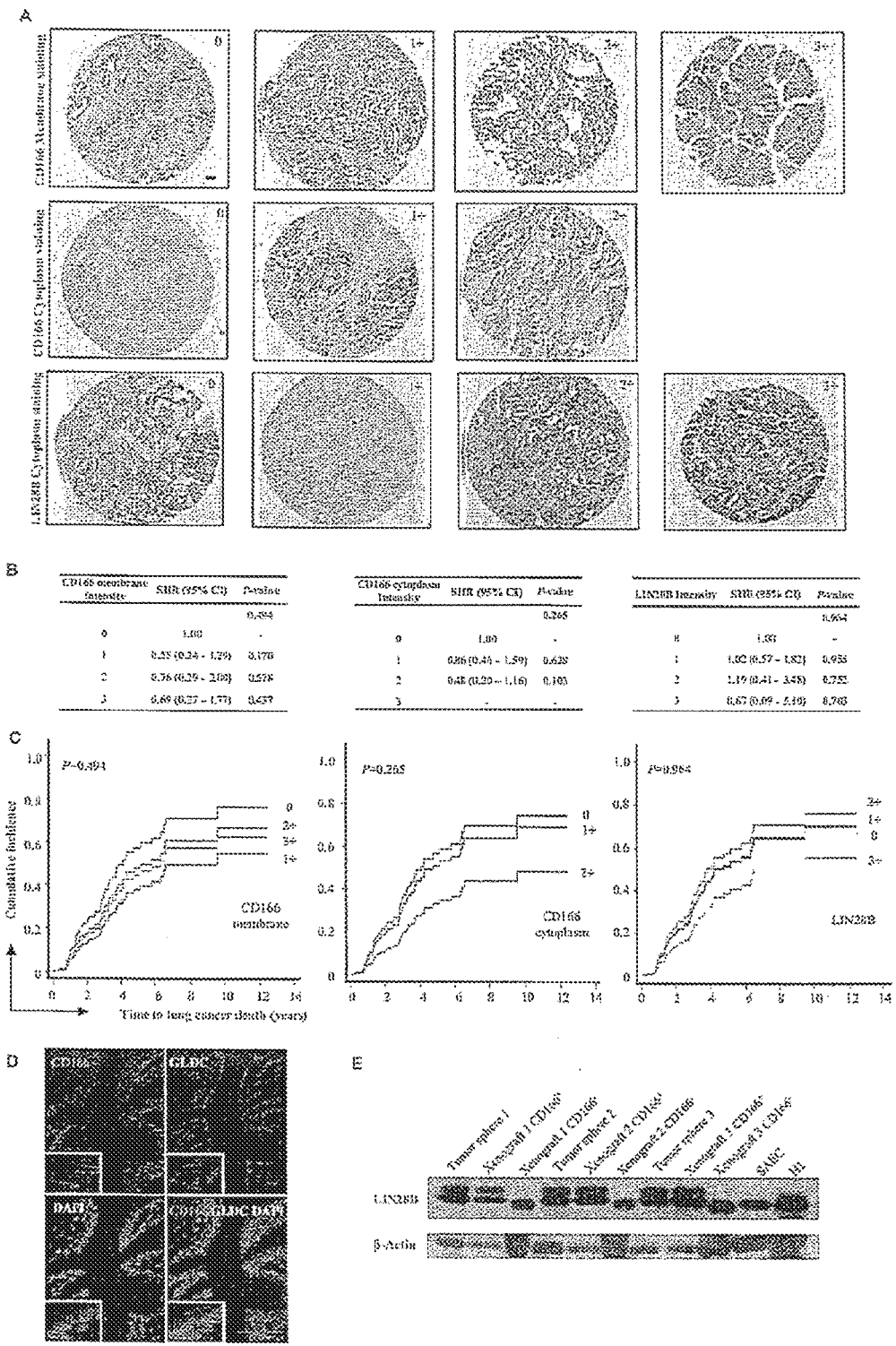

FIG. 20. CD166 and LIN28B expression do not predict mortality in NSCLC patients (A) CD166 and LIN28B immunohistochemistry staining in NSCLC (n=143). Both AdC and SCC showed graded staining intensity (0, 1+, 2+ and 3+) in a membranous and/or cytoplasmic staining pattern. Staining intensity is indicated in upper right corner. Scale bar, 100 μm.

(B) Subdistribution hazard ratio (SHR) for different CD166 membrane, CD166 cytoplasm and LIN28B staining intensity grades, adjusted for AJCC staging. CI, confidence interval.

(C) Cumulative incidence of lung cancer mortality adjusted for AJCC staging, according to CD166 membrane, CD166 cytoplasm or LIN28B expression intensity.

(D) Co-immunofluorescence staining of CD166 (red) and GLDC (green) on normal primary small bronchial airways, counterstained with DAPI (blue). A representative case with co-expression of CD166 and GLDC is shown. Higher magnification inset is shown in bottom left corner. Scale bar, 50 μm.

(E) LIN28B protein expression in tumor sphere, xenograft CD166$^+$, and xenograft CD166$^-$ cells from 3 different patient samples, by Western blot. SAEC and H1 cells served as negative and positive controls respectively. SAEC, small airway epithelial cells. H1, human embryonic stem cells.

Figure 21:
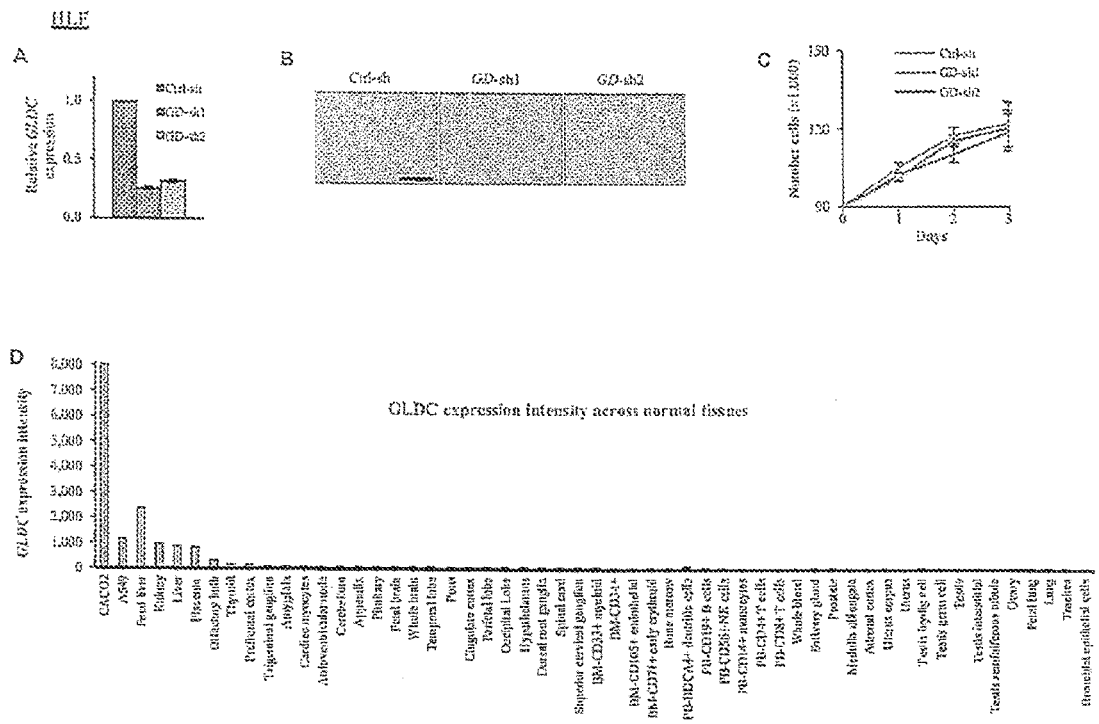

FIG. 21. GLDC expression in normal tissues (A) Expression of GLDC in HLF cells expressing two shRNA against GLDC (GD-sh1/2), as determined by qRT-PCR.

(B) Proliferation curve of HLFs with GLDC knockdown.

(C) Phase contrast images of HLFs with GLDC knockdown. Scale bar, 100 μm.

(D) GLDC expression across normal adult human tissues and cells by microarray analysis. Transformed CACO2 and A549 cells served as positive controls.

In all panels, error bars represent SEM.

Figure 22:
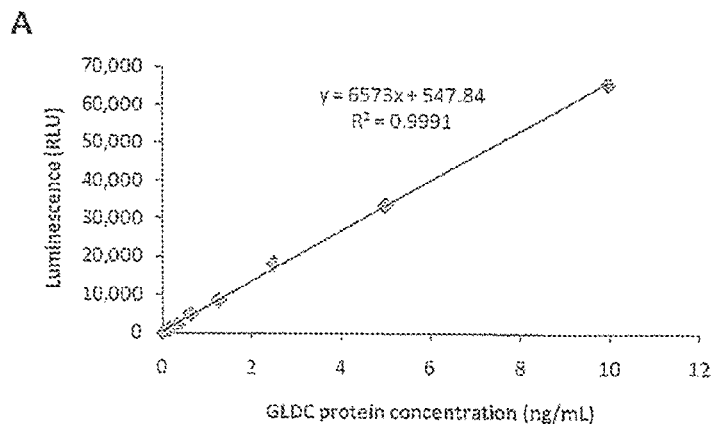
Figure 22:
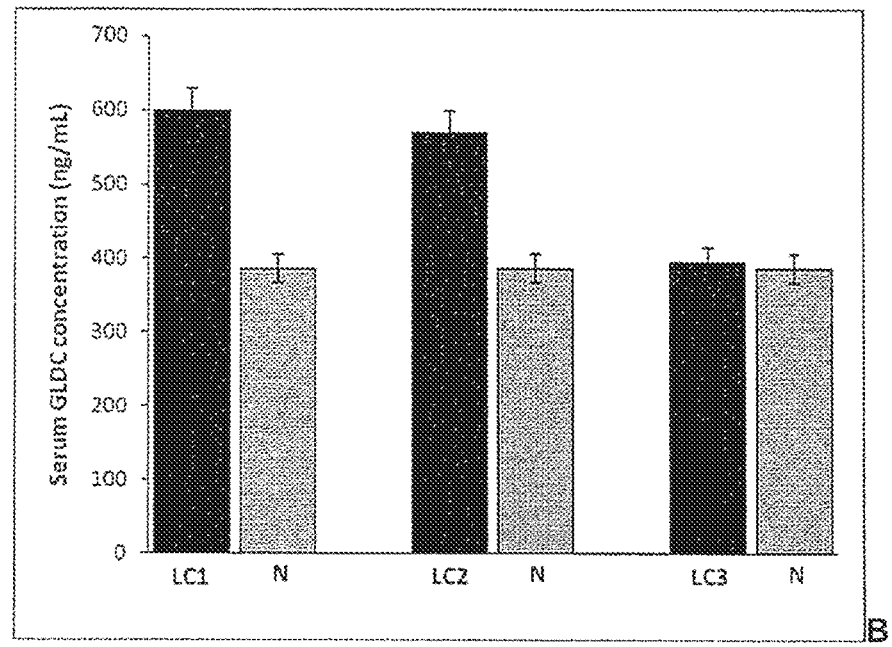
Figure 22:
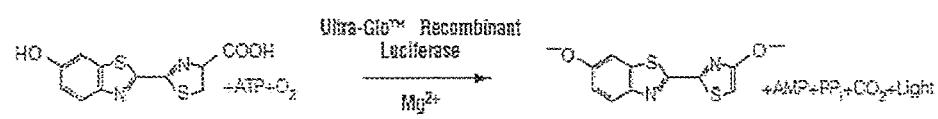
Figure 22:
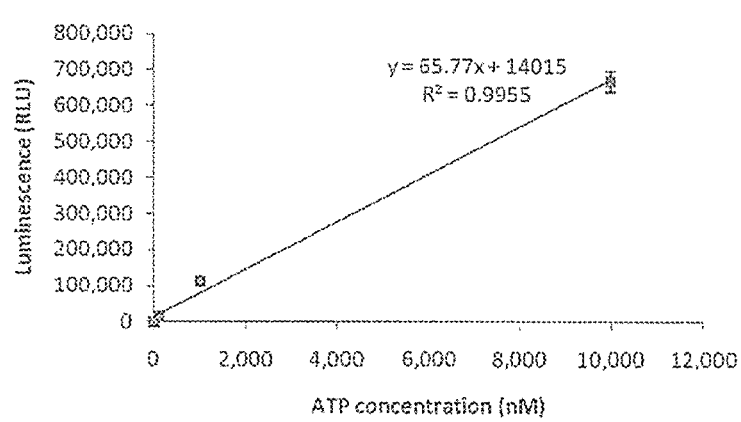
Figure 22:
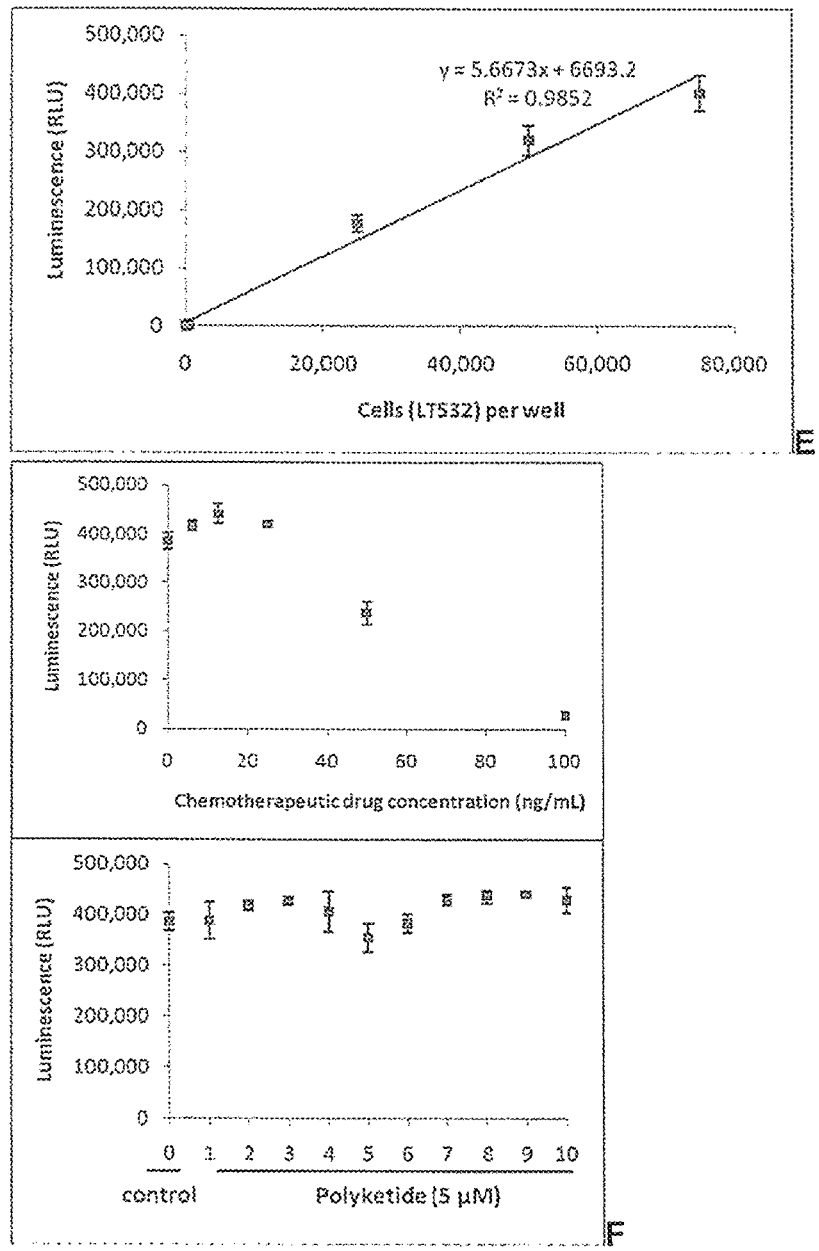

FIG. 22. GLDC protein concentration immunoassay (A) There is a linear relationship between GLDC protein concentration and Luminescence signals, Sensitivity: 0.156~10 ng/mL GLDC protein level, Fast: 5 hours (B) GLDC quantification in serum from NSCLC patients (C) Tumor suppression cellular assay CellTiter-Glo® Luminescent Cell Viability Assay based on the Luciferase reaction principle (D) Linear relationship_standard curve (ATP vs. RLU) (E) Linear relationship (tumor sphere cells vs. RLU) (F) Assay of chemotherapeutic drugs (Carboplatin top pannel) and chemical inhibitors (Polyketide lower pannel).

DETAILED DESCRIPTION

The present technology relates to metabolic enzymes as targets in cancers, whereby GLDC is the metabolic enzyme and the subject cancer is any cancer cell exhibiting elevated levels of GLDC expression above expression of GLDC in cells isolated from normal non-cancerous tissue. GLDC is a target for cancer treatment and GLDC expression levels correlate with tumorigenicity. The present technology can be used to distinguish cancer cells from normal cells and inhibition of GLDC can be used as a cancer therapy.

Here we find that, glycine dehydrogenase (GLDC), one of the metabolic enzyme involved in glycine metabolism, is overexpressed in various subtypes of human lung cancer, colon cancer and possibly several other types of cancers. GLDC was found to be highly expressed in tumor-initiating subpopulation of human lung cancer cells compared with non-tumorigenic subpopulation. By array studies we showed that normal lung cells express low levels of GLDC compared to xenograft and primary tumor. Functional studies showed that RNAi inhibition of GLDC inhibits significantly the clonal growth of tumor-initiating cells in vitro and tumor formation in immunodeficient mice. Overexpression of GLDC in non-tumorigenic subpopulation convert the cells to become tumorigenic. Furthermore, overexpression of GLDC in NIH/3T3 cells and human primary lung fibroblasts can transform these cells, displaying anchorage-independent growth in soft agar and tumor-forming in mice. Not only is GLDC is expressed human lung cancer, it is also up-regulated in other types of cancer, such as colon cancer. RNAi knockdown of GLDC in colon cancer cell line, CACO-2 cells, can also inhibit the tumor formation in mice. Thus GLDC maybe a new metabolic target for treatment of lung cancer, and other cancers.

Metabolic enzyme, glycine dehydrogenase (GLDC) is distinguished in tumorigenic human lung cancer cells versus non-tumorigenic human lung cancer cells and normal lung cells by large scale gene expression profile analysis and tissue microarray analysis.

GLDC is also up-regulated in a lot of cancer, including lung cancer and colon cancer. This is the first time GLDC is recognised to be overexpressed in tumor initiating cells. High levels of GLDC expression in a cell demonstrate a significant correlation with tumorigenicity and increased cell proliferation.

Down-regulation of GLDC expression in tumorigenic human lung cancer cells inhibited tumor growth in colony forming assay and in mice. This is the first time that inhibition of GLDC enzyme is shown to treat cancer such as lung cancer. Inhibition of GLDC by Knockdown of GLDC levels in a cancer cell reduced tumour formation and cell proliferation. This is an alternative method of cancer treatment targeting a metabolic enzyme.

Up-regulate GLDC expression in NIH/3T3 cells and lung fibroblasts can transform cells displaying colony formation in vitro and tumor formation in mice. This is the first time that GLDC has been shown to be functional in tumor initiation and expansion. Overexpression of GLDC expression levels elevated tumorigenesis and pell proliferation both in vitro and in vivo.

Here we show that the metabolic enzyme glycine decarboxylase (GLDC) is critical for tumor initiating cell (TIC) state in non-small cell lung cancer (NSCLC). TICs from primary NSCLC tumors express high levels of the oncogenic stem cell factor LIN28B and GLDC, which were both required for TIC growth and tumorigenesis. Overexpression of GLDC and other glycine/serine enzymes, but not catalytically inactive GLDC, promotes cellular transformation and tumorigenesis. We found that GLDC induces dramatic changes in glycolysis and glycine/serine metabolism, leading to changes in pyrimidine metabolism to regulate cancer cell proliferation. In the clinic, aberrant activation of GLDC correlates with poorer survival in lung cancer patients, and aberrant GLDC expression is observed in multiple cancer types. This link between glycine metabolism and tumorigenesis may provide novel targets for anti-cancer therapy.

NSCLC tumor initiating cells express high levels of GLDC.

GLDC is a metabolic oncogene that promotes cellular transformation.

GLDC activity regulates pyrimidine metabolism in cancer cells.

Mortality in NSCLC patients is predicted by GLDC expression.

The present invention is not limited to a particular mechanism. Indeed, an understanding of the mechanism is not necessary to practice the present invention. Nonetheless, it is contemplated that an inhibitor against GLDC finds use in the treatment of cancer, which almost universally cancer cells overexpresses GLDC. Furthermore, aggressive localized tumors expressing high levels of GLDC are also therapeutically targeted by GLDC inhibitors. Without being limited to any theory we think tumor cells are addicted to high level of the enzyme GLDC and inhibition of GLDC in cancer cells may not be tolerated effectively blocking, stopping or slowing cell proliferation whereas normal cells may still survive.

The present technology relates to a method of treating cancer by inhibiting GLDC expression in cells. The GLDC gene sequence described herein, including that set out in SEQ ID No. 1, includes functional derivatives, homologues and variants that express a functional GLDC protein as set out in SEQ ID No 2. We have found that inhibition of GLDC expression, results in the reduction of tumours and cell proliferation. There is provided method of inducing apoptosis of a cell comprising the steps of: treating the cell with an inhibitor of GLDC expression. Preferably the method further provides the step of adding a chemotherapeutic agent to the cell.

Polynucleotides

An isolated GLDC nucleic acid molecule is disclosed which molecule typically encodes a GLDC polypeptide, allelic variant, or analog, including fragments, thereof. Specifically provided are DNA molecules selected from the group consisting of: (a) DNA molecules set out in SEQ ID NO: 1 or fragments thereof; (b) DNA molecules that hybridize to the DNA molecules defined in (a) or hybridisable fragments thereof; and (c) DNA molecules that code an expression for the amino acid sequence encoded by SEQ ID NOS: 1 or fragments thereof.

Preferred DNA molecules according to the invention include DNA molecules comprising the sequence set out in SEQ ID NO: 1. or fragments thereof.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"GLDC gene sequence," "GLDC gene," "GLDC nucleic acids" or "GLDC polynucleotide" each refer to polynucleotides that are likely to be expressed in cancer tissue such as lung tissue.

The GLDC gene sequence is intended to include coding sequences, intervening sequences and regulatory elements controlling transcription and/or translation. The GLDC gene sequence is intended to include all allelic variations of the DNA sequence.

These terms, when applied to a nucleic acid, refer to a nucleic acid that encodes a GLDC polypeptide, fragment, homologue or variant, including, e.g., protein fusions or deletions. The nucleic acids of the present invention will possess a sequence that is either derived from, or substantially similar to a natural GLDC encoding gene or one having substantial homology with a natural GLDC encoding gene or a portion thereof. The coding sequence for human GLDC polypeptide is shown in SEQ ID NO: 1 with the amino acid sequence shown in SEQ ID NO: 2 respectively. A further poly nucleotide LIN28B nucleic acid may be expressed in cancer cells. The coding sequence for human LIN28B polypeptide is shown in SEQ ID NO: 4 with the amino acid sequence shown in SEQ ID NO: 5 respectively. The same can be used to detect cancer is a cell.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Bestfit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequence set out in SEQ ID. Nos 1.

Other preferred polynucleotides comprise a contiguous sequence having greater than 40, 50, 60, or 70% homology, more preferably greater than 80, 90, 95 or 97% homology to the sequence of SEQ ID NO: 1 that encodes amino acids 1 to 1020 of SEQ ID No: 2.

Nucleotide sequences are preferably at least 15 nucleotides in length, more preferably at least 20, 30, 40, 50, 100 or 200 nucleotides in length.

Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the GLDC nucleotide sequences set out in the sequence listings herein. Conversely, where a polynucleotide of the invention consists of, for example, greater than 50 or 100 nucleotides, the % identity compared with the GLDC nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees C., typically in excess of 37 degrees C., and preferably in excess of 45 degrees C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15 M NaCl, 0.015 M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

GLDC Polypeptides

Full length GLDC polypeptides of the present invention have about 1000 to 1200 amino acids, encode a Glycine dehydrogenase [decarboxylating] in a eukaryotic organism, particularly an animal; a mammal or a human, and include allelic variants or homologues. GLDC polypeptides also typically comprise fragments and derivatives of full length GLDC polypeptides, particularly fragments or derivatives having substantially the same biological activity. The GLDC polypeptides include those comprising the amino acid sequence of SEQ ID NOS: 2 or allelic variants or homologues, including fragments, thereof. A particularly preferred polypeptide consists of amino acids 1 to 1020 of the amino acid sequence shown as SEQ ID NO: 2 or allelic variants, homologues or fragments, thereof.

The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID. Nos 2. In particular, homology should typically be considered with respect to those regions of the sequence known to be essential for the function of the protein rather than non-essential Other preferred polypeptides comprise a contiguous sequence having greater than 40, 50, 60, or 70% homology, of SEQ ID No: 2. Although homology can also be considered in terms of similarity (i.e. amino acid residues having similar chemical properties/functions), in the context of the present invention it is also possible to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate % homology between two or more sequences.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

GLDC polypeptide homologues include those having the amino acid sequences, wherein one or more of the amino acids is substituted with another amino acid which substitutions do not substantially alter the biological activity of the molecule. A GLDC polypeptide homologue according to the invention preferably has 80 percent or greater amino acid sequence identity to the human GLDC polypeptide amino acid sequence set out in SEQ ID NO: 2. Examples of GLDC polypeptide homologues within the scope of the invention include the amino acid sequence of SEQ ID NOS: 2 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

Preferably "GLDC protein" or "GLDC polypeptide" refers to a protein or polypeptide encoded by the GLDC gene sequence, variants or fragments thereof. Also included are proteins encoded by DNA that hybridize under high or low stringency conditions, to GLDC encoding nucleic acids and closely related polypeptides or proteins retrieved by antisera to the GLDC protein(s).

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

Preferred polypeptides of the invention have substantially similar function to wild type full length GLDC. Preferred polynucleotides of the invention encode polypeptides having substantially similar function to wild type full length GLDC. "Substantially similar function" refers to the function of a nucleic acid or polypeptide homologue, variant, derivative or fragment of GLDC with reference to the wild-type GLDC nucleic acid or wild-type GLDC polypeptide.

However, non-functional forms of GLDC polypeptides may also be included within the scope of the invention since they may be useful, for example, as antagonists of GLDC function.

"Probes". Polynucleotide polymorphisms associated with GLDC alleles are detected by hybridisation with a polynucleotide probe which forms a stable hybrid with that of the target sequence, under stringent to moderately stringent hybridisation and wash conditions. If it is expected that the probes will be perfectly complementary to the target sequence, stringent conditions will be used. Hybridisation stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a GLDC in cancer cells.

Probes for GLDC nucleic acid may be derived from the sequences of the GLDC region or its cDNAs. The probes may be of any suitable length, which span all or a portion of the GLDC nucleic acid. If the target sequence contains a sequence identical to that of the probe, the probes may be short, e.g., in the range of about 8-30 base pairs, since the hybrid will be relatively stable under even stringent conditions. If some degree of mismatch is expected with the probe, i.e., if it is suspected that the probe will hybridize to a variant region, a longer probe may be employed which hybridises to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g. Sambrook et al., 1989: "Molecular Cloning: a laboratory manual. Sambrook, J., Fritsch, E. F. and Maniatis, T. (1989). Coldspring Harbour Laboratory Press, Cold spring Harbour, N.Y. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding GLDC are preferred as probes. The probes may also be used to determine whether mRNA encoding GLDC is present in a cell or tissue.

The present invention provides one or more GLDC polynucleotides or fragments thereof comprising mutations with respect to the wild type sequence, such as the sequence shown in SEQ ID No. 1. In a further embodiment, the present invention provides a plurality of GLDC polynucleotides or fragments thereof. The plurality of sequences is conveniently provided immobilised to a solid substrate as is described below.

Nucleic Acid Arrays—"DNA Chip" Technology

Polynucleotides of the invention, including probes that may be used to detect GLDC sequences in nucleic acid samples such as mRNA taken from patients, may be immobilized to a solid phase support. The probes for GLDC will typically form part of a library of DNA molecules that may be used to detect simultaneously a number of different genes in a given genome.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produce the immobilised DNA libraries of the present invention. U.S. Pat. No. 5,837,832 also provides references for earlier techniques that may also be used. Thus nucleic acid probes may be synthesised in situ on the surface of the substrate.

Alternatively, single-stranded molecules may be synthesised off the solid substrate and each pre-formed sequence applied to a discrete position on the solid substrate. For example, nucleic acids may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal. A particular example of a suitable solid substrate is the commercially available BiaCore™ chip (Pharmacia Biosensors).

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 μm, giving a density of 10000 to 40000 $cm^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the nucleic acid sequences to the substrate may be by covalent or non-covalent means. The nucleic acid sequences may be attached to the substrate via a layer of molecules to which the library sequences bind. For example, the nucleic acid sequences may be labelled with biotin and the substrate coated with avidin and/or streptavidin. A convenient feature of using biotinylated nucleic acid sequences is that the efficiency of coupling to the solid substrate can be determined easily. Since the nucleic acid sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art see for example WO98/49557.

Binding of complementary nucleic acid sequence to the immobilised nucleic acid library may be determined by a variety of means such as changes in the optical characteristics of the bound nucleic acid (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (SPR)—see WO97/49989, incorporated herein by reference.

Thus the present invention provides a solid substrate having immobilized thereon at least one polynucleotide of the present invention, for example GLDC polynucleotides. In a preferred embodiment the solid substrate further comprises polynucleotides derived from genes other than the GLDC gene such as a probe to polynucleotides known to be over expressed in cancer cells.

Any GLDC nucleic acid specimen, in purified or non-purified form, can be utilised as the starting nucleic acid or acids.

PCR is one such process that may be used to amplify GLDC gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilised.

The specific nucleic acid sequence to be amplified, i.e., the polymorphic gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

Nucleic acid utilized herein may be extracted from a body sample, such as blood, tissue material, lung tissue, colon tissue, breast tissue and the like by a variety of techniques such as that described by Maniatis, et. al. in Molecular Cloning: A Laboratory Manual, Cold Spring Harbor, N.Y., p 280-281, 1982). If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers, in adequate amounts and the resulting solution is heated to about 90 degrees-100 degrees C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40 degree C. Most conveniently the reaction occurs at room temperature.

Specific oligonucleotide primers derived from GLDC gene sequence may be useful in determining whether a subject is at risk of suffering from the ailments described herein. Primers direct amplification of a target polynucleotide e.g. GLDC prior to sequencing. Primers used in any diagnostic assays derived from the present invention should be of sufficient length and appropriate sequence to provide initiation of polymerisation. Environmental conditions conducive to synthesis include the presence of nucleoside triphosphates and an agent for polymerisation, such as DNA polymerase, and a suitable temperature and pH.

Primers are preferably single stranded for maximum efficiency in amplification, but may be double stranded. If double stranded, primers may be first treated to separate the strands before being used to prepare extension products. Primers should be sufficiently long to prime the synthesis of GLDC extension products in the presence of the inducing agent for polymerization. The exact length of a primer will depend on many factors, including temperature, buffer, and nucleotide composition. Oligonucleotide primers will typically contain 12-20 or more nucleotides, although they may contain fewer nucleotides.

Primers that may be used in diagnostic assays derived from the present invention should be designed to be substantially complementary to each strand of the GLDC genomic gene sequence. This means that the primers must be sufficiently complementary to hybridise with their respective strands under conditions that allow the agent for polymerisation to perform. In other words, the primers should have sufficient complementarity with the 5' and 3' sequences flanking the detection site to hybridise therewith and permit amplification of the GLDC genomic gene sequence.

Oligonucleotide primers of the invention employed in the PCR amplification process that is an enzymatic chain reaction that produces exponential quantities of GLDC nucleic acid sequence relative to the number of reaction steps involved. Typically, one primer will be complementary to the negative (−) strand of the GLDC nucleic acid sequence and the other is complementary to the positive (+) strand. Annealing the primers to denatured nucleic acid followed by extension with an enzyme, such as the large fragment of DNA polymerase I (Klenow) and nucleotides, results in newly synthesised + and − strands containing the target a GLDC nucleic acid sequence. Because these newly synthesized sequences are also templates, repeated cycles of denaturing, primer annealing, and extension results in exponential production of the region (i.e., the GLDC nucleic acid sequence) defined by the primers. The product of the chain reaction is a discreet nucleic acid duplex with termini corresponding to the ends of the specific primers employed.

Oligonucleotide primers may be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, 1981. One method for synthesising oligonucleotides on a modified solid support is described in U.S. Pat. No. 4,458, 066.

The agent for polymerisation may be any compound or system which will function to accomplish the synthesis of primer extension products, including enzymes. Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products that are complementary to each GLDC sequence nucleic acid strand. Generally, the synthesis will be initiated at the 3' end of each primer and proceed in the 5' direction along the template strand, until synthesis terminates, producing molecules of different lengths.

The newly synthesised GLDC strand and its complementary nucleic acid strand will form a double-stranded molecule under hybridizing conditions described above and this hybrid is used in subsequent steps of the process. In the next step, the newly synthesized double-stranded molecule (GLDC) is subjected to denaturing conditions using any of the procedures described above to provide single-stranded molecules.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et. al., Bio/Technology, 3:1008-1012, 1985), allele-specific oligonucleotide (ASO) probe analysis (Conner, et. al., Proc. Natl. Acad. Sci. U.S.A., 80:278, 1983), oligonucleotide ligation assays (OLAs) (Landgren, et. al., Science, 241:1007, 1988), and the like. Molecular techniques for DNA analysis have been reviewed (Landgren, et. al., Science, 242:229-237, 1988).

Preferably, the method of amplifying GLDC nucleic acid is by PCR, as described herein or real time PCR and as is commonly used by those of ordinary skill in the art. Alternative methods of amplification have been described and can also be employed as long as the GLDC nucleic acid sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for hincII with short overhang on the 5' end that binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37 degrees C. Unlike PCR and LCR, SDA does not require instrumented temperature cycling. Another amplification system useful in the method of the invention is the QB Replicase System. Although PCR is the preferred method of amplification if the invention, these other methods can also be used to amplify the GLDC nucleic acid sequence as described in the method of the invention.

A "tissue sample", as used herein, refers to a biological sample obtained from a tissue in the body, for example a biopsy. In a preferred embodiment the tissue sample is of a tumor. Frequently the tissue sample will be a "clinical sample," which is a sample derived from a patient such as a fine needle biopsy sample. A "tissue sample" may also include a section of tissue such as a section taken from a frozen or fixed tumor. Tissue samples can be obtained from tumors of the lung, colon, breast, or cancer tumours located at other sites for example but not limited to bladder, brain, uterus, cervix, colon, rectum, esophagus, mouth, head, skin, kidney, lung, ovary, neck, pancreas, prostate, testis, liver and stomach. The tissue sample may be present on a tissue array or may comprise a whole tissue section. An "evenly matched" tissue sample is a tissue sample of the same type (i.e. comprising the same types of cells from the same type of tumour from the same type of subject). "Evenly matched" tissue samples can be used to provide reference profiles in the methods provided herein. The evenly matched tissue can be used as a sample isolated from normal, non-cancerous cells.

A "tumour" refers to an abnormal growth of tissue that may be comprised of cells that for example, proliferate rapidly. Tumours may be present, for example, in the breast, bladder, brain, uterus, cervix, colon, rectum, esophagus, head, skin, kidney, lung (including Non Small Cell Lung Cancer), ovary, neck, pancreas, prostate, testis, liver and stomach.

A further aspect of the invention is a compound comprising a GLDC inhibitor capable of inhibiting expression of GLDC. Preferably the compound further comprises a DNA damaging agent. Preferably the DNA damaging agent is a chemotherapeutic agent.

GLDC Inhibitors

A GLDC inhibitor is any protein, peptide, nucleic acid, such as siRNA, antibodies capable of selectively binding the GLDC polypeptide, small molecule compound or the like that can stop, hinder or block the expression of GLDC protein.

Micro RNA

In some embodiments, the present invention provides MicroRNAs that inhibit the expression of GLDC. MicroRNAs are regulatory, non-protein-coding, endogenous RNAs that have recently gained considerable attention in the scientific community. They are 18-24 nucleotides in length and are thought to regulate gene expression through translational repression by binding to a target. They are also proposed to regulate gene expression by mRNA cleavage, and mRNA decay initiated by miRNA-guided rapid deadenylation. miRNAs are abundant, highly conserved molecules and predicted to regulate a large number of transcripts. To date the international miRNA Registry database has more than 600 human identified microRNAs and their total number in humans has been predicted to be as high as 1,000. Many of these microRNAs exhibit tissue-specific expression and many are defined to play a crucial role in variety of cellular processes such as cell cycle control, apoptosis, and haematopoiesis.

GLDC expression is inhibited by Glycine dehydrogenase specific microRNA for example; MISSION® shRNA Lentiviral Transduction Particles (Sigma, NM_000170/TRCN0000036600 of SEQ ID NO: 70: CGGCCTGCCAA-CATCCGTTTGAAACTC-GAGTTTCAAACGGATGTTGGCAGGTTTTG.

Accordingly, in some embodiments, the present invention provides methods of inhibiting GLDC expression and/or activity using microRNAs. In some embodiments, miRNAs inhibit the expression of GLDC protein. In other embodiments, miRNAs GLDC activity.

The present invention is not limited to disclosed RNAi. Additional miRNAs can be screened for their activity against GLDC using any suitable method, including, but not limited to, those disclosed below. Suitable nucleic acids for use in the methods described herein include, but are not limited to, pri-miRNA, pre-miRNA, mature miRNA or fragments of variants thereof that retain the biological activity of the miRNA and DNA encoding a pri-miRNA, pre-miRNA, mature miRNA, fragments or variants thereof, or DNA encoding regulatory elements of the miRNA.

In some embodiments the nucleic acid encoding the disclosed inhibitory nucleic acids, for example a miRNA molecule, is on a vector. These vectors include a sequence encoding a mature microRNA and in vivo expression elements. In a preferred embodiment, these vectors include a sequence encoding a pre-miRNA and in vivo expression elements such that the pre-miRNA is expressed and processed in vivo into a mature miRNA. In other embodiments, these vectors include a sequence encoding the pri-miRNA gene and in vivo expression elements. In this embodiment, the primary transcript is first processed to produce the stem-loop precursor miRNA molecule. The stem-loop precursor is then processed to produce the mature microRNA. Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; murine mammary tumor virus; Rous sarcoma virus; adenovirus; adeno-associated virus; SV4O-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

GLDC Antibodies

The present invention also provides labelled and unlabeled monoclonal and polyclonal antibodies specific for GLDC polypeptides of the invention and immortal cell lines that produce a monoclonal antibody of the invention. Antibody preparation according to the invention involves: (a) conjugating a GLDC polypeptide to a carrier protein; (b) immunizing a host animal with the GLDC polypeptide fragment-carrier protein conjugate of step (a) admixed with an adjuvant; and (c) obtaining antibody from the immunized host animal.

According to the invention, GLDC polypeptide produced recombinantly or by chemical synthesis, and fragments or other derivatives or analogs thereof, including fusion proteins, may be used as an immunogen to generate antibodies that recognize the GLDC polypeptide. Such antibodies include but are not limited to polyclonal, monoclonal, chimeric, single chain, Fab fragments, and a Fab expression library.

Thus, the present invention also provides polyclonal and/or monoclonal antibodies and fragments thereof, and immunologic binding equivalents thereof, which are capable of specifically binding to the GLDC polypeptides and fragments thereof. Such antibodies thus include for example, but are not limited to polyclonal, monoclonal, chimeric, single chain, Fab fragments, and a Fab expression library. Production of antibodies specific for GLDC polypeptides or fragments thereof is described below.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, F(ab')$_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to GLDC polypeptide, or fragment, derivative or analog thereof. For the production of antibody, various host animals can be immunized by injection with the GLDC polypeptide, or a derivative (e.g., fragment or fusion protein) thereof, including but not limited to rabbits, mice, rats, sheep, goats, etc. In one embodiment, the GLDC polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the GLDC polypeptide, or fragment, analog, or derivative thereof, any technique that provides for the production of antibody molecules by continuous cell lines in culture may be used. These include but are not limited to the hybridoma technique originally developed by Kohler et al., *Nature*, 256: 495-497 (1975), as well as the trioma technique, the human B-cell hybridoma technique [Kozbor et al., *Immunology Today*, 4:72 (1983)], and the EBV-hybridoma technique to produce human monoclonal antibodies [Cole et al., in *Monoclonal Antibodies and Cancer Therapy*, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451, 570; 4,466,917; 4,472,500; 4,491,632; and 4,493,890.

In an additional embodiment of the invention, monoclonal antibodies can be produced in germ-free animals utilizing recent technology (PCT/US90/02545). According to the invention, human antibodies may be used and can be obtained by using human hybridomas [Cote et al., *Proc. Natl. Acad. Sci. USA*, 80:2026-2030 (1983)] or by transforming human B cells with EBV virus in vitro (Cole et al., 1985, supra). In fact, according to the invention, techniques developed for the production of "chimeric antibodies" [Morrison et al., *J. Bacteriol.*, 159-870 (1984); Neuberger et al., *Nature*, 312:604-608 (1984); Takeda et al., *Nature*, 314:452-454 (1985)] by splicing the genes from a mouse antibody molecule specific for a GLDC polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies (U.S. Pat. No. 4,946, 778) can be adapted to produce GLDC polypeptide-specific single chain antibodies. An additional embodiment of the invention utilizes the techniques described for the construction of Fab expression libraries [Huse et al., *Science*, 246: 1275-1281 (1989)] to allow rapid and easy identification of monoclonal Fab fragments with the desired specificity for a GLDC polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognize a specific epitope of a GLDC polypeptide, one may assay generated hybridomas for a product that binds to a GLDC polypeptide fragment containing such epitope.

The foregoing antibodies can be used in methods known in the art relating to the localization and activity of the GLDC polypeptide, e.g., for Western blotting, imaging GLDC polypeptide in situ, measuring levels of GLDC expression thereof in appropriate physiological samples, etc. In a preferred embodiment the antibodies of the invention are used to inhibit GLDC expression as a cancer therapy.

In a specific embodiment, antibodies are developed by immunizing rabbits with synthetic peptides predicted by the protein sequence or with recombinant proteins made using bacterial expression vectors. The choice of synthetic peptides is made after careful analysis of the predicted protein structure, as described above. In particular, peptide sequences between putative cleavage sites are chosen. Synthetic peptides are conjugated to a carrier such as KLH hemocyanin or BSA using carbodiimide and used in Freunds adjuvant to immunize rabbits. In order to prepare recombinant protein, the pGEX vector can be used to express the polypeptide. Alternatively, one can use only hydrophilic domains to generate the fusion protein. The expressed protein will be prepared in quantity and used to immunize rabbits in Freunds adjuvant.

In yet another embodiment, recombinant GLDC polypeptide is used to immunize rabbits, and the polyclonal antibodies are immunopurified prior to further use. The purified antibodies are particularly useful for semi-quantitative assays, particularly for detecting the presence of GLDC polypeptide.

Preferably, the anti-modulator antibody used in the diagnostic and therapeutic methods of this invention is an affinity-purified polyclonal antibody. More preferably, the antibody is a monoclonal antibody (mAb). In addition, it is preferable for the anti-modulator antibody molecules used herein be in the form of Fab, Fab', F(ab')$_2$ or F(v) portions of whole antibody molecules.

In a preferred embodiment of the invention, antibodies will immunoprecipitate GLDC proteins from solution as well as react with GLDC protein on Western or immunoblots of polyacrylamide gels. In another preferred embodiment, antibodies will detect GLDC proteins in paraffin or frozen tissue sections, using immunocytochemical techniques.

Preferred embodiments relating to methods for detecting GLDC include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

Small Molecule Therapies

In other embodiments, the present invention provides small molecule inhibitors of GLDC expression or activity. Victorin a toxin secreted by the fungus *Conchliobolus victoriae* is suspected to inhibit glycine decarboxylase in plants. Here we show that Victorin is able to inhibit GLDC expression and block or reduced tumour formation and cell proliferation. Accordingly, in some embodiments, the present invention provides methods of treating cancer (e.g., metastatic cancer) using victorin or related compounds.

Victorin is a peptide with an apparent molecular weight of about 796-814 and a composition $C_{31}H_{45}O_{13}N_6Cl_3$. Preferably Victorin has the structure of formula I:

Wherein $R_1$=OH and $R_2$=H

Victorin may be isolated directly from *Conchliobolus victoriae* grown in culture as known by those skilled in the art alternatively it may be synthesised from desglyovictorin= (NH$_2$—Cl$_2$leu-Ohlys-(oHleu-aClaa-victala)$_{cyclo}$ wherein Preferably victala has the structure of formula II:

In a preferred method of manufacture victorin can be regenerated from the non toxic desglyovictorin and glyoxylic acid using an N-hydroxysuccinimide acylation method. To illustrate by example only where the amounts may vary proportionally depending of the amount of victorin required: 140 mg of N-hydroxy-succinimide and then 400 mg of dicylohexylcarbodiimide are added to a solution of 88 mg of glyoxylic acid in 4 ml of dioxane, the solution left at room temperature for 1 hour and filtered. 0.1 ml of filtrate is added to a solution of 300 µg of desglyovictorin in 1 ml of potassium phosphate buffer pH 6 and left at room temperature for 1 hour. The reaction mixture is centrifuged and the supernatant chromatographed on a HPLC column (e.g. HPLC $C_{18}$ column equilibrated with 10 mM $KH_2PO_4$) and eluted with a 2 hour linear gradient of 0-20% acetonitrile in 10 mM $KH_2PO_4$ at a flow rate of 3 ml/min. The purified victorin may be desalted for example with a $C_{18}$ sep-pak.

Aminooxyacetate is a powerful inhibitor of both cytoplasmic and mitochondrial aspartate aminotransferase or of glutamate transaminases. It binds to GLDC and inhibits GLDC activity. (Aminooxy) acetate (AOA) has a CAS Number: 645-88-5 and a composition $C_2H_4NO_3$ having the structure of formula III:

III

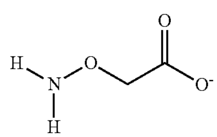

As described herein the term "Cancer" refers to malignant neoplasm, or a group of cells that display uncontrolled division and growth beyond the normal limits, i.e.: abnormal proliferation of cells, invasion, intrusion on and destruction of adjacent tissues, and sometimes metastasis where the cancer cells have spread to other locations in the body via lymph system or blood. Most cancers form a tumor but some, like leukemia, do not. For the purpose of the invention cancer refers to cells where GLDC expression has been upregulated. For example in cancer cells present in bone, lung, breast, gastric, colorectal, liver, prostate, cervical, brain, oral, esophagus, head and neck, lymphoma, leukemia, ovary, bladder, pancreatic, skin, sarcoma or any other cancers known to those skilled in the art.

DNA Damaging Agents

DNA damaging agents are any agents that can cause damage to nucleic acids. Preferably DNA damaging agents are anticancer agents such as chemotherapy agents like, for example; Adriamycin (ADR), Etoposide (ETO, Nocodazole, cisplatin, platinum, carboplatin, gemcitabine, paclitaxel, docetaxel, vinorelbine, topotecan, or irinotecan; tyrosine kinase inhibitors (e.g., Axitinib, Bosutinib, Cediranib, Dasatinib, Erlotinib, Gefitinib, Imatinib, Lapatinib, Lastaurtinib, Nilotinib, semaxanib, sunitinib, vandetanib, vatalanib or any other suitable tyrosine kinase inhibitor); apoptosis inducing enzymes, for example TNF polypeptides, TRAIL (TRAIL R1, TRAIL R2) or FasL, Exisulind or other apoptosis inducing enzymes; micro-RNA that initiates apoptosis; or other chemotherapy agents such as those commonly known to a person skilled in the art. Alternatively they may be anticancer treatments such as radiotherapy, chest radiotherapy, surgical resection, the chemotherapy agents mentioned above or any combination of these.

In one embodiment the chemotherapeutic agent comprises methotrexate. In another embodiment the chemotherapeutic agent comprises carboplatin.

Compositions of the Invention compositions produced according to the invention can be administered for the treatment of cancer in the form of pharmaceutical compositions.

Thus, the present invention also relates to compositions including pharmaceutical compositions comprising a therapeutically effective amount of a compound that inhibits GLDC protein expression. As used herein a compound will be therapeutically effective if it is able to affect cancer growth either in vitro or in vivo.

Pharmaceutical forms of the invention suitable for injectable use include sterile aqueous solutions (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active peptides in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

When the active ingredients, in particular small molecules contemplated within the scope of the invention, are suitably protected they may be orally administered, for example, with an inert diluent or with an edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active molecules in such therapeutically useful compositions is such that a suitable dosage will be obtained. Preferred compositions or preparations according to the present invention are prepared so that a dosage unit form contains between about 0.1 μg and 20 g of active compound.

The tablets, troches, pills, capsules and the like may also contain binding agents, such as, for example, gum, acacia, corn starch or gelatin. They may also contain an excipient, such as, for example, dicalcium phosphate. They may also contain a disintegrating agent such as, for example, corn starch, potato starch, alginic acid and the like. They may also contain a lubricant such as, for example, magnesium stearate. They may also contain a sweetening agent such a sucrose, lactose or saccharin. They may also contain a flavouring agent such as, for example, peppermint, oil of wintergreen, or cherry flavouring.

When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparaben as preservatives, a dye and flavouring such as, for example, cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µs to about 2000 mg. Expressed in proportions, the active compound is generally present in from about 0.5 pg to about 2000 mg/ml of carrier. In the case of compositions containing supplementary active ingredients, the dosages are determined by reference to the usual dose and manner of administration of the said ingredients.

The compounds and compositions may be adapted to be administered to the lungs directly through the airways by inhalation. Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluents such as lactose or starch. Inhalable dry powder compositions may be presented in capsules and cartridges of gelatin or a like material, or blisters of laminated aluminum foil for use in an inhaler or insufflators. Each capsule or cartridge may generally contain between 20 pg-10 mg of the active compound. Alternatively, the compound of the invention may be presented without excipients.

The inhalable compositions may be packaged for unit dose or multi-dose delivery. For example, the compositions can be packaged for multi-dose delivery in a manner analogous to that described in GB 2242134, U.S. Pat. No. 6,632,666, U.S. Pat. No. 5,860,419, U.S. Pat. No. 5,873,360 and U.S. Pat. No. 5,590,645 (all illustrating the "Diskus" device), or GB2178965, GB2129691, GB2169265, U.S. Pat. No. 4,778,054, U.S. Pat. No. 4,811,731 and U.S. Pat. No. 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurised packs, such as a metered dose inhaler (MDI), with the use of a suitable liquefied propellant. The medication in pressurized MDI is most commonly stored in solution in a pressurized canister that contains a propellant, although it may also be a suspension.

Aerosol compositions suitable for inhalation can be presented either as suspensions or as solutions and typically contain the active compound and a suitable propellant such as a fluorocarbon or hydrogen-containing chlorofluorocarbon or mixtures thereof, particularly hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof.

The aerosol composition may optionally contain additional excipients typically associated with such compositions, for example surfactants such as oleic acid or lecithin and co-solvents such as ethanol. Pressurized formulations will generally be contained within a canister (for example an aluminum canister) closed with a metering valve and fitted into an actuator provided with a mouthpiece.

Peptides can also be delivered by protein delivery methods known in the art such as transfection, macromolecule delivery vehicles and other methods known to those skilled in the art.

The compositions may be for use in treating cancer. Use includes use of a composition of the invention for the preparation of a medicament or a pharmaceutically acceptable composition for the treatment of cancer. The preparation may further comprise a chemotherapeutic agent for the preparation of a medicament for the treatment of cancer.

Method for Treating a Patient with Cancer

On the basis of the above, the present invention provides a method for treating a patient with cancer, which comprises the step of: contacting the cells within and around a cancer with a composition as described above. Desirably, the GLDC inhibitor is provided in a therapeutically effective amount.

An alternative form of the present invention resides in the use of the composition in the manufacture of a medicament for treating a patient with cancer preferably a medicament used in treatment to affect cells over expressing GLDC.

"Treatment" and "treat" and synonyms thereof refer to both therapeutic treatment and prophylactic or preventative measures, wherein the object is to prevent or slow down (lessen) a cancer condition. Those in need of such treatment include those already diagnosed with cancer or having cells over expressing GLDC.

As used herein a "therapeutically effective amount" of a compound will be an amount of active peptide, siRNA, antibody, molecule such as victorin or (aminooxy) acetate or any GLDC inhibitor that is capable of preventing or at least slowing down (lessening) a cancer condition, in particular increasing the average 5 year survival rate of cancer patients. Dosages and administration of an antagonist of the invention in a pharmaceutical composition may be determined by one of ordinary skill in the art of clinical pharmacology or pharmacokinetics. See, for example, Mordenti and Rescigno, (1992) Pharmaceutical Research, 9:17-25; Morenti et al., (1991) Pharmaceutical Research, 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the peptide to be employed therapeutically will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 µg/kg/day to 10 mg/kg/day.

Screening for Antagonists to Lung Cancer Stem Cells

Consistent with the invention there is provided a means for screening for cancer antagonists that inhibit GLDC expression in cells comprising the steps of: (a) detecting the expression profile of GLDC in cancer cells (b) contacting a test compound on the cancer cells and (c) detecting the expression profile of GLDC in cancer cells that were exposed to test compound (d) comparing the expression profile of GLDC in the cells before they were exposed to the test compound to the expression profile of GLDC in cancer cells that were exposed to test compound whereby a decrease in the level of GLDC expression after exposure to the test compound indicates the test compound may be a cancer antagonist suitable for treating cancer.

Screening assays for antagonist drug candidates are designed to identify compounds that inhibit GLDC expression in a cell or reduce cell proliferation in a group of cells. Such screening assays will include assays amenable to high-throughput screening of chemical libraries, making them particularly suitable for identifying small molecule drug candidates.

The assays can be performed in a variety of formats, including protein binding assays, biochemical screening assays, immunoassays, and cell-based assays, which are well characterized in the art. Such assays for antagonists are common in that they call for contacting test compound with a cancer, tumour or cell line for a time sufficient to allow these components to interact; and detecting whether the test compound exhibits an antagonistic activity such as reducing the size of the tumour or arresting the growth of the tumour or arresting proliferation within the cell line. Similarly the antagonist may reduce the metastatic potential of a group of cancer cells or reduce the migratory response of the group of cancer cells.

Compounds can be tested as follows: a tumour cell line is seeded onto feeder plates to grow colonies. Alternatively a tumour is initiated in a test animal such as an immunodeficient mouse by injecting a population of cancer cells into the test animal. A reaction mixture is prepared containing the test compound. The reaction mixture is contacted with the tumour cell line or injected into the tumour of the test animal for a time allowing for the interaction and binding of the products. To test the ability of a candidate compound to inhibit binding, the reaction is run in the absence and in the presence of the test compound. In addition, a placebo may be added to a third reaction mixture, to serve as a further control. The effect of the test compound present in the mixture is monitored as described hereinabove. The arrest or reduction of the colony growth or the arrest or reduction of the tumour growth in the test animal but not in the reaction mixture without the test compound with or without the placebo indicates that the test compound interferes with the cancer cells. The test compound exhibits an antagonistic activity if it reduced the expression profile of the GLDC polypeptide, or reduces or arrests proliferation of the group of cancer cells, or induces a rate of apoptosis to 10% or more in the group of cancer cells (10% being above the homeostatic rate of apoptosis) or reduce the metastatic potential of a group of cancer cells or reduce the migratory response of the group of cancer cells.

Methods of creating lung cancer stem cell lines are described in WO 2010/126452 the entire contents of which are incorporated by reference.

The screening method may comprise forming a tumour either in vitro, in or on a cultured substrate or in vivo, such as by injecting cancer inducing cells into an immunodeficient mouse or other suitable test animal to induce tumour formation. The resulting tumour is contacted with a test compound and observed for antagonistic activity. A test compound exhibits an antagonistic activity in this embodiment if it reduces the size of the tumour or arrests the growth of the tumour.

Potential antagonists include small molecules that inhibit GLDC expression, thereby blocking the normal biological activity of the cell such as glycine metabolism. Examples of small molecules include, but are not limited to, small peptides or peptide-like molecules, preferably soluble peptides, and synthetic non-peptidyl organic or inorganic compounds, small interfering RNAs, derivative or isoforms of victorin.

These small molecules can be identified by any one or more of the screening assays discussed hereinabove and/or by any other screening techniques well known for those skilled in the art.

The present invention also relates to compounds identified by the above method and their use in treating lung cancer in a patient.

Diagnosis

A further aspect of the invention comprises a method of predicting the effectiveness of a compound of the invention comprising the step of determining a first expression profile of GLDC in a subject who is not suspected to have cancer; determining a second expression profile of GLDC in a subject who is suspected to have cancer and comparing the first and second expression profile whereby when the second expression profile is greater by 1.5 to 16 fold more than the first expression profile or preferably 2 to 8 fold more than the subject who is suspected to have cancer will benefit from treatment with the compound of the invention.

The expression of GLDC increases with increased tumor-orgenisis. There is a 1.5 to 20 fold amplification of the amount of GLDC in a cancer sample relative to the amount of GLDC in a control sample isolated from normal non-cancerous cells. Consequently, establishing the status of the amount of GLDC of an individual with possible breast cancer may be a useful diagnostic and/or prognostic tool.

Diagnostic and prognostic methods will generally be conducted using a biological sample obtained from a patient. A "sample" refers to a sample of tissue or fluid suspected of containing an analyte polypeptide from an individual including, but not limited to, e.g., plasma, serum, spinal fluid, lymph fluid, the external sections of the skin, respiratory, intestinal, and genitourinary tracts, tears, saliva, blood cells, organs, tissue including breast tissue and samples of in vitro cell culture constituents.

According to the diagnostic and prognostic methods of the present invention, alteration of the GLDC sequence expression taken from a cell or tissue suspected to be tumorigenic when compared to the GLDC sequence expression taken from a normal, non-cancerous cell or tissue may be detected using anyone of the methods described herein. In addition, the diagnostic and prognostic methods can be performed to detect the GLDC sequence expression and confirm the presence of a cancer or a predisposition to cancer. An increase of the GLDC sequence expression above that of a is indicative of the presence of a cancer or a predisposition to cancer.

The method may further comprising the steps of detecting measuring an amount of LIN28B nucleic acid or polypeptide in the cell isolated from tissue suspected of being cancerous; Comparing the amount of LIN28B nucleic acid or polypeptide present in the cell to the amount of LIN28B nucleic acid or polypeptide in a sample isolated from normal, a non-cancerous cell, wherein an amplified amount of LIN28B nucleic acid or polypeptide in the cell relative to the amount of LIN28B nucleic acid or polypeptide in the non-cancerous cell indicates cancer is present in the cell; and wherein the absence of an amplified amount of LIN28B nucleic acid or polypeptide in the cell relative to the amount of LIN28B nucleic acid or polypeptide in the non-cancerous cell indicates there is no cancer present in the cell.

A further step of isolating lung cancer stem cells prior to determining the expression profile of GLDC in a cell or a subject who is suspected to be cancerous or have cancer may advance early detection possibly making treatment even more effective. Many studies have shown that early detection increases survival rates in patients. A method of isolating and enriching lung cancer stem cells is described in WO 2010/126452 the entire content of which is incorporated by reference.

The method of detecting GLDC and or LIN28B may include an ELISA assay, immunohistochemical methods, microarray analysis or any other method known in the art.

Detection Kits

Detection kits may contain a reagent capable of binding selectively a GLDC polypeptide or nucleic acid. In one embodiment the reagent is an antibody capable of binding selectively a GLDC polypeptide. In another embodiment the reagent is a primer or a probe capable of binding selectively a GLDC nucleic acid. The kit may further contain amplification systems, detection reagents (chromogen, fluorophore, etc), an enzyme capable of breaking down the natural extracellular matrix of the tissue to dissociate the cells (e.g., Trypsin, Elastase, Collagenase type 1 or 2, Protease, Pronase or any other suitable enzyme), dilution buffers, washing solutions, mounting solutions, counter stains or any combination thereof. Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, stratifying patient populations, diagnosis, prognosis, guiding therapeutic treatment decisions, and other applications.

Detection kits may further comprise magnetic beads such as dyna-beads or miltany beads or fluorophores for cell sorting techniques such as MACS or FACS and or secondary antibodies for extraction of cells with an existing antibody-antigen complex.

The detection kit may include a reagent such as an antibody capable of binding selectively a GLDC polypeptide which comprises a sequence capable of binding selectively a sequence set out in SEQ ID No 2, or the reagent may include a polynucleotide or a primer and a probe capable of binding selectively a GLDC polynucleotide. Preferably the polynucleotide is an mRNA allowing GLDC expression profiling of cells in vitro.

The detection kit may further comprise a CD166 antibody for enriching or isolating lung cancer stem cells. The CD166 antibody for isolating and enriching lung cancer stem cells is described in WO 2010/126452 the entire content of which is incorporated by reference.

EXAMPLES OF SPECIFIC EMBODIMENTS

Here we show that glycine metabolism and the metabolic enzyme glycine decarboxylase (GLDC) drives TICs and tumorigenesis in non-small cell lung cancer (NSCLC). Using CD166 as a surface marker and NOD/SCID Il2ry$^{-/-}$ mice as xenotransplantation recipients, we isolated lung TICs from a broad range of primary NSCLC tumors (stage I-III). Primary lung TICs express high levels of LIN28B, GLDC, and many other glycine/serine metabolism enzymes. Both LIN28B and GLDC were required for lung TIC proliferation and tumor growth. Overexpression of GLDC alone, and other glycine/serine enzymes, promotes cellular transformation both in vitro and in vivo. Metabolomic analysis shows that GLDC overexpression induces dramatic changes in glycolysis and glycine metabolism, leading to changes in pyrimidine metabolism for cancer cell proliferation. In human patients, aberrant upregulation of GLDC is significantly associated with higher mortality from lung cancer, and aberrant GLDC expression is observed in multiple cancer types. Our findings establish a link between glycine metabolism and tumorigenesis, and may provide novel targets for advancing anti-cancer therapy.

Tumor Initiating Cell-State in Lung Cancer

Our work sheds new light on the nature of the tumor initiating cell-state and the role of metabolic reprogramming in tumorigenesis. In this study, we isolated a subpopulation of tumor initiating cells from non-small cell lung cancer patients using the marker CD166, and showed that both the oncogenic stem cell factor LIN28B and the glycine metabolism enzyme GLDC drive the tumorigenicity of lung cancer tumor initiating cells.

Our data showed that CD166 enriched for TICs in primary NSCLC, and that CD166 served as an inert surface marker. In contrast, our results on CD133 are different from the results reported earlier even though both studies used the same CD133 antibody. This is most likely due to differences in the xenotransplantation assays, which tend to underestimate the true frequency of TICs. We employed a more sensitive mouse xenotransplantation assay using NOD/SCID Il2ry$^{-/-}$ mice instead of SCID mice, and we directly transplanted primary tumor cells with Matrigel instead of expanding the tumor cells in vitro. Previous studies have demonstrated that using a more sensitive mouse xenotransplantation assay dramatically improves our understanding of TICs. Our present study supports this notion, leading us to CD166 as a new marker for the lung TIC-containing fraction. In normal physiology, CD166 is expressed predominantly during embryonic development, including the embryonic upper airway, primitive cardiac cells and mesenchymal stem cells. Expression of CD166 in the embryonic lung is consistent with our observation that CD166$^+$ lung TICs express high levels of embryonic lung transcription factors like PEA3 and the trachealess homolog NPAS1, as well as the oncogenic stem cell factor LIN28B. Interestingly, mouse Lin28 is also expressed in the embryonic lung during normal development (Yang and Moss, 2003).

These observations suggest that the TIC-state in lung cancer is similar to the embryonic lung progenitor—state in many aspects.

Glycine Decarboxylase GLDC is a Metabolic Oncogene

Our results demonstrate that multiple components in the glycine/serine pathway are also oncogenes. In addition to embryonic lung factors, lung TICs also express high levels of GLDC, GCAT, SHMT1/2, PSPH, and PSAT1, suggesting that TICs rely on glycine/serine metabolism for tumorigenesis. Overexpression of catalytically active GLDC, as well as PSAT1, PSPH and SHMT2, could induce cellular transformation in 3T3 cells to form tumors, whereas retroviral knockdown of GLDC significantly reduced the tumorigenicity of lung cancer cells. We further observed that GLDC$^+$ cells mostly form a subset of CD166$^+$ cells in lung tumors.

PSAT1, PSPH, and SHMT1/2 lie upstream of GLDC in the glycine/serine pathway, diverting glycolytic flux from 3-phosphoglycerate through serine to glycine. GLDC is an oxidoreductase that catalyzes the irreversible rate-limiting step of glycine catabolism, by breaking down each glycine molecule in the glycine cleavage system to produce NADH, $CO_2$, $NH_3$ and $CH_2$-THF. $CH_2$-THF fuels the one-carbon/folate metabolism pool, which in turn supplies methylene groups for biosynthesis. Consistent with these facts, we found that GLDC regulates many metabolites in glycolysis and the glycine/serine pathway, leading to specific changes in pyrimidine synthesis. Pyrimidine derivatives like thymidine, in turn, are required for nucleotide synthesis in cell proliferation. Recent studies suggest that early oncogenesis involves aberrant activation of cell proliferation, which then leads to a crisis of nucleotide deficiency and replication stress a crisis that GLDC upregulation could overcome for continued progression in tumorigenesis. Interestingly we found that GLDC also increases the levels of N-methylglycine or sarcosine, an oncometabolite implicated in prostate cancer. Furthermore we observed that GLDC promotes glycolysis. Combined with our findings on LIN28, which has been shown to promote glucose uptake and glycolysis, GLDC might be cooperating with LIN28 as well as PSAT1, PSPH and SHMT1/2 to divert the glycolytic flux to glycine and produce $CH_2$-THF. These observations support the notion that the Warburg effect promotes biosynthesis for tumorigenesis.

GLDC and Glycine Metabolism are Relevant to Human Cancer Patients

From the prognostic perspective, aberrant GLDC expression is significantly correlated with the survival rates of NSCLC patients. This is consistent with the model that TIC clones expand to constitute the bulk of the tumor in advanced stages of malignancy. Aberrantly increased GLDC is also widespread in many other human cancers, including lymphoma, ovarian, germ cell, cervical, prostate, bladder and colon cancer, while most normal adult human tissues express very low levels of GLDC. Our experimental data further suggests that in cancers which rely on GLDC and glycine metabolism, the highly toxic anti-folate drug methotrexate might be initially effective because it targets TICs, although our data suggest an even more effective chemotherapy could be potentially achieved by combining an anti-folate drug with a GLDC inhibitor or by searching for a glycine cleavage complex-specific anti-folate drug—much like the search for kinase-specific inhibitors in targeted cancer therapy.

Our study is the first to link a glycine metabolism enzyme to lung cancer and tumorigenesis. Regardless of the controversy over the frequency of TICs at different stages of malignancy, our approach shows that characterizing the unique molecular basis that defines cancer cells with tumorigenic capacity may nevertheless provide novel drug targets for advancing cancer therapy.

Experimental Procedures

Tumor Cell Preparation

NSCLC tumors were collected from patients according to protocols approved by the Ethics Committee of National University of Singapore. Samples were washed, dissociated, and incubated in DNAse and collagenase/dispase. See Extended Experimental Protocols for more details. Surgical samples were collected from consenting patients at the National University Hospital of Singapore, Singapore General Hospital, and Tan Tock Seng Hospital according to human subject research protocols approved by the Ethics Committee of National University of Singapore. All patients were first diagnosed with primary NSCLC and did not show other tumor occurrences. Patients also did not receive any chemotherapy or radiotherapy before surgery. Samples were shipped to laboratory in cold phosphate buffer saline (PBS) with antibiotics (Sigma-Aldrich, St. Louis, Mo.) within one hour of removal from patients. Samples were washed with cold PBS with antibiotics three times, chopped with a sterile blade, and incubated in 0.001% DNAse (Sigma-Aldrich, St. Louis, Mo.), 1 mg/ml collagenase/dispase (Roche, Indianapolis, Ind.), 200 U/ml penicillin, 200 µg/ml streptomycin, 0.5 µg/ml amphotericin B (2% antibiotics, Sigma) in DMEM/F12 medium (GIBCO, GrandIsland, N.Y.) at 37° C. water bath for 3 hours with intermittent shaking. After incubation, the suspensions were repeatedly triturated, passed through 70 µm and 40 µm cell-strainers (BD Falcon, San Jose, Calif.), and centrifuged at 800 rpm for 5 min at 4° C. Cells were resuspended in red blood cell lysis buffer (eBioscience, San Diego, Calif.) for 4 min at room temperature with intermittent shaking, before resuspension in DMEM/10% FBS medium. After lysis, cell viability was evaluated by trypan blue dye exclusion. Live single cells account for 90% of the whole population and dead cells account for less than 10%. Each tumor sample yields ~$1 \times 10^4$ to $3 \times 10^6$ cells, depending on the sample size.

FACS

Single cells were incubated with FcR Blocking Reagent (Miltenyi) in ice for 20 min, labelled with antibodies against CD166, CD133, CD44, EpCAM, and the lineage markers (human CD45/CD31 for patient tumors, and mouse H-2K$^d$/CD45 for xenografts). 7-amino-actinomycin D (BD PharminGen) was added to exclude dead cells. Appropriate isotype antibodies were used as controls.

H&E, Immunohistochemistry and Immunofluorescence

Samples were formalin-fixed, paraffin-embedded, sectioned and stained with haematoxylin-eosin (H&E) according to standard histopathological techniques. For immunohistochemistry, sections were incubated with anti human CD166 (Novaocastra), anti-pan-CK (DakoCytomation), anti-human GLDC (Sigma), E-cadherin (Dako), smooth muscle actin (Dako), synaptophysin(Dako), Vimentin (Dako) or anti-human LIN28B (Abgent) and visualized using the Envision HRP Polymer System (Dako). For immunofluorescence, sections were incubated with mouse anti-CD166 (R&D), washed, then incubated with anti mouse IgG Alexa Fluor 568 (Invitrogen). All images were captured on a Zeiss LSM 510 meta confocal laser scanning microscope.

Cell Culture

Mouse embryonic fibroblasts (NIH/3T3, ATCC) and normal human adult lung fibroblasts (HLF) were cultured in DMEM/10% FBS/glutamine. Human lung cancer cell line (A549) was maintained in DMEM/10% FBS. Human colon cancer cell line (CACO2) was cultured under DMEM/20%

FBS/non-essential amino acid. Normal human bronchial/tracheal epithelial Cells (NHBE) and small airway epithelial cells (SAEC) (Clonetics) were cultured in basal medium containing BSA, BPE, hydrocortisone, hEGF, epinephrine, transferrin, insulin, retinoic acid, triiodothyronine, GA-1000. Normal breast epithelial cells (MCF 10A, ATCC) was cultured in MEGM containing MEBM plus BPE, hydrocortisone, EGF, insulin, cholera toxin and GA-1000.

Tumor Sphere Assay

Single-cell suspensions (10,000 cells/well) were plated in 6-well ultra-low attachment (Corning) or non-treated cell culture plates (Nunc) in DMEM/F12 medium containing 2 mM L-glutamine, 15 mM HEPES, 1 mg/ml NaHCO$_3$, 0.6% Glucose, 1% NEAA, 4 mg/ml BSA (Sigma), ITS (0.05 mg/ml insulin/transferrin/selenous acid, BD Biosciences), 1% antibiotics (Sigma), 50 ng/ml EGF and 20 ng/ml bFGF (Invitrogen). Fresh medium was replenished every 3 days. Tumor spheres were cultured for 10-14 days and then quantified. For passaging, tumor spheres were digested by accutase (Chemicon) into single cells and re-plated into the above plates.

cDNA Microarray Analysis

Total RNA was extracted by Trizol (Invitrogen) and purified by RNeasy Mini Kit (QIAGEN). Lung primary tumors (1 patient), tumor xenografts (3 patients), tumor spheres (4 patients) and normal human adult lung tissues (3 patients) were used. RNA was processed and hybridized to Human-Ref-8 v3.0 Beadarrays (Illumina), and the microarray data was normalized and analysed as described previously (Chua, S. W., Vijayakumar, P., Nissom, P. M., Yam, C. Y., Wong, V. V. T., and Yang, H. (2006). A novel normalization method for effective removal of systematic variation in microarray data. Nucleic Acids Research 34, e38). A fold change cut-off threshold of 1.5 was applied to generate the lung TIC gene signature after four comparisons: primary tumor CD166$^+$ vs. CD166$^-$ (P$^+$/P$^-$), xenograft tumor CD166$^+$ vs. CD166$^-$ (X$^+$/X$^-$), spheres vs. xenograft tumor CD166$^+$ (S/X$^+$), and normal lung CD166$^+$ vs. CD166$^-$ (N$^+$/N$^-$). After intersecting the differentially expressed genes (DEGs) of P$^+$/P$^-$, X$^+$/X$^-$, S/X$^+$ and excluding DEGs intersecting with N$^+$/N$^-$, DAVID Bioinformatics Resources 6.7 was applied for KEGG pathway analysis of the final list of DEGs (Huang et al., 2009).

Gene Knockdown and Overexpression

All shRNAs construct in retroviral vector (pGFP-V-RS) were obtained from Origene, and sequences may be found in Table 8. 1.5 µg of shRNA construct and 4.5 µl of TurboFectin 8.0 (Origene) were used for transfection. LIN28B shRNA lentiviral particles (TRCN0000122599) and control lentivirus (SHC002V) were purchased from Sigma. Cells were transduced with equal amounts of lentivirus/retrovirus, and selected in puromycin. 4 different shRNAs were used for knockdown of each gene to control for non-specificity. Human cDNA clones GLDC (RG211292), LIN28B (RG213537), PSPH (RG209090), PSAT1 (RG202475), SHMT1 (RG203461), SHMT2 (RG204239) and GCAT (RG204870) and were obtained from Origene. 0.8 µg of cDNA clone and 2.4 µl of TurboFectin 8.0 were used for transfection, and cells were selected in neomycin. We subcloned human GLDC, LIN28B cDNA into pBabe.Puro retroviral vectors. pMN vector and plasmids (oncogenic KRAS-G12D, PI3K-E545K, MYC, MYC-T58A) were provided by Q.Y. mRNA expression changes were quantitated by qPCR using TaqMan probes (Invitrogen).

TABLE 8 shRNA and primer sequences

| SEQ ID NO. | Target gene | | Catalog no. |
|---|---|---|---|
| | | shRNA sequences | |
| 71 | GLDC | shRNA1: TAGCTGTTGTCCAGACTCGAGCCAAATAT; | Origene TG312759 |
| 72 | | shRNA2: GGTCAATCCGCTGAAGATGTCTCCACACT; | |
| 73 | | shRNA3: TGGAGAGTTTACTCAACTACCAGACCATG; | |
| 74 | | shRNA4: TTCACTAAAGCGGAATGAGGATGCCTGTC | |
| 75 | LIN28B | shRNA1: AACGGTCAGGCAGGTCACCTCAAGAAGCT; | Origene TG311724 |
| 76 | | shRNA2: GCCACTGTAAGTGGTTCAATGTGCGCATG; | |
| 77 | | shRNA3: AGAAGTGCCATTACTGTCAGAGCATCATG; | |
| 78 | | shRNA4: TACATCACCACCGTTTCCTCAGGAGGCTA | |
| 14 | ALCAM | shRNA1: GAGCAGTTCATTCTACCAAGCTGTCACAGG; AAGGTGTTCAAGCAACCAATCTAAACCTGA; | Origene TG314848 |
| 15 | | shRNA2: AAGGTGTTCAAGCAACCATCTAAACCTGA; | |
| 16 | | shRNA3: TTACTATCCTACAGAGCAGGTGACAATAC; | |
| 17 | | shRNA4: GAAGCATGAACGTGGATTGTATTTAAGAC | |
| 18 | Control | scrambled control shRNA: GCACTACCAGAGCTAACTCAGATAGTACT | Origene TR30013 |

TABLE 8-continued shRNA and primer sequences

| SEQ ID NO. | Target gene | | Catalog no. |
|---|---|---|---|
| 19 | LIN28B | SHCLNV: CCGGGCCTTGAGTCAATACGGGTAACTCGAGTTACCCGTATTGACTCAAGGCTTTTTG | Sigma TRCN0000 122599 |
| 20 | Control | control SHCLNV: CCGGCAACAAGATGAAGAGCACCAACTCGAGTTGGTGCTCTTCATCTTGTTGTTTTT Primer sequence | SHC002V |
| 21 | GLDC | CCAGACACGACGACTTCGC (hs_1_F) | |
| 22 | | CAATTCATCAATGCTCGCCAG (hs_1_R) | |
| 23 | | ATTTCTCGTTGATCCCCGTTG (hs_2_F) | |
| 24 | | CACAGGGTAACTTCAGCTCAG (hs_2_R) | |
| 25 | | CAGGGTCAATCCGCTGAAGATG (hs_3_F) | |
| 26 | | TGCTGCCACCTCTCTGGAATAAG (hs_3_R) | |
| 27 | | AACCAGGGAGCAACACATTCGG (hs_4_F) | |
| 28 | | ATATTCGCCAAGAGGGCCTGAG (hs_4_R) | |
| 29 | PSPH | GAGGACGCGGTGTCAGAAAT (hs_1_F) | |
| 30 | | GGTTGCTCTGCTATGAGTCTCT (hs_1_R) | |
| 31 | | GCATAAGGGAGCTGGTAAGTCG (hs_2_F) | |
| 32 | | ACCTGCATATTCACCGTTAAAGT (hs_2_R) | |
| 33 | | TCATGATTGGAGATGGTGCCACAG (hs_3_F) | |
| 34 | | CAATGAAAGCATCAGCAGGAGGAC (hs_3_R) | |
| 35 | | ACGGTGAATATGCAGGTTTTGA (hs_4_F) | |
| 36 | | GTTATCCTTGACTTGTTGCCTGA (hs_4_R) | |
| 37 | PSAT1 | TGCCGCACTCAGTGTTGTTAG (hs_1_F) | |
| 38 | | GCAATTCCCGCACAAGATTCT (hs_1_R) | |
| 39 | | TCTACGTCATGGGCTTGGTTCTG (hs_2_F) | |
| 40 | | GCTCCACTGGACAAACGTAGAATC (hs_2_R) | |
| 41 | | CAGTGGATGTTTCCAAGTTTGGTG (hs_3_F) | |
| 42 | | CCTGCACCTTGTATTCCAGGAC (hs_3_R) | |
| 43 | | AGCAGGAAGGTGTGCTGACTA (hs_4_F) | |
| 44 | | CGGCCTTAGCTGACCAAGC (hs_4_R) | |
| 45 | SHMT1 | AAATCTCTGCCACGTCCATCTTC (hs_1_F) | |
| 46 | | AGCCAGTATCTGGGTTCACCTTG (hs_1_R) | |
| 47 | | CGAAGCTGATCATCGCAGGAAC (hs_2_F) | |
| 48 | | TCTCATCTGCAATCTTCCGTAGCC (hs_2_R) | |
| 49 | | CTGGCACAACCCCTCAAAGA (hs_3_F) | |
| 50 | | CTCTGCCGGTTACTCTCCTTC (hs_3_R) | |
| 51 | | CAGCCGAGCAGTTTTGGAG (hs_4_F) | |
| 52 | | GTCCCGCCATAGTATCTCTGG (hs_4_R) | |
| 53 | SHMT2 | CTTCTGCAACCTCACGACC (hs_1_F) | |
| 54 | | TGAGCTTATAGGGCATAGACTCG (hs_1_R) | |
| 55 | | CTTAGAGGTGAAGAGCAAGACTGC (hs_2_F) | |
| 56 | | AGACGCTGACTTGTTTCTGAGTCC (hs_2_R) | |
| 57 | | ACTACAACCAGCTGGCACTGAC (hs_3_F) | |
| 58 | | TGCTTTGACTTCATCACACACCTC (hs_3_R) | |
| 59 | | GACTACGCCCGCATGAGAG (hs_4_F) | |
| 60 | | AGCAGGTGTGCTTTGACTTCA (hs_4_R) | |
| 61 | GCAT | GGCCGACCTAGAAGCCAAG (hs_1_F) | |
| 62 | | GTGCGATGTCGCCATCCAT (hs_1_R) | |
| 63 | | CGCTTTATCTGTGGAACCCAGAGC (hs_2_F) | |
| 64 | | AACAGCTGGGATAGAGGATGGC (hs_2_R) | |
| 65 | | AAGGCCCTAGATCTGCTGATGG (hs_3_F) | |
| 66 | | GCTTCCATCTTACTACGGAACCTC (hs_3_R) | |
| 67 | | CCTCAGCTCTGTCCGCTTTAT (hs_4_F) | |
| 68 | | GGATGCCGTCGATGATGGAG (hs_4_R) | |

Cell Proliferation Assay

To assess cellular proliferation, cells were seeded in triplicate in 6-well plates and were counted using a hematocytometer and trypan blue staining to exclude dead cells.

Adherent Colony Formation Assay

Adherent colony formation was performed by seeding 200-3000 single cells into 10 cm-culture dish and maintained for 10-14 days in DMEM/10% FBS. Colonies were stained by Wright-Giemsa and those colonies containing more than 50 cells were counted. For methotrexate (Sigma) treatment assay, cells were maintained in growth medium containing serial dilution of methotrexate (0, 0.1, 0.2, 0.5, 1, 2, 5, 10, 20 uM) and fresh medium were changed every 3 days.

Soft Agar Colony Formation Assay

Soft agar assays were conducted as described previously (Viswanathan et al., 2009). We stained colonies with 1% INT and counted them after 3-4 weeks of growth. For sarcosine rescue experiment, 10 μM of sarcosine (sigma) or PBS were added to top cells layer of agar and growth medium containing sarcosine were changed every 3 days before counting colonies.

Lactate Assay

Cells were plated at density of $7 \times 10^5$ per 10-cm culture dish with complete growth medium 12 hrs before assay. Then the cells was washed and changed by fresh DMEM/1% FBS. The supernatants were collected following medium changing at sequential time point (0, 1, 2, 4, 8, 24 hr) and quick-frozen into liquid nitrogen. Then lactate assay was performed according to manufacturer's instruction (Biovision) and O.D. 570 was measured in a microplate reader.

Metabolomics

Metabolites were extracted by centrifugation of culture media at 14000 rpm for 30 min at 4° C. Supernatants were treated through Water's Oasis 1cc HLB cartages following manufacturer instructions to remove all protein and lipid contamination. Metabolomic profiling was performed through UPLC/MS to ion suppression, using Agilent 1200 RRLC and Agilent 6530 Accurate Mass QTOF. Three microliters of each sample was chromatographed on a Zorbax Eclipse Plus-C18 column (100 mm×2.1 mm, 1.8 um) using an Agilent 1200 RRLC system. Flow rate was maintained at 0.4 ml/min in a 15-min run with a gradient mobile phase: A) 0.1% FA in water; B) 0.1% FA in ACN (t=0-0.5 min, B=10%; t=0.5-9 min, B=95%; t=9-12 min, B=95%; t=12-12.1 min, B=10%). The column was reconditioned back to normal condition for next injection. To avoid any carry over from previous injection, blank was injected before all biological replicates. The eluent was introduced directly into the mass spectrometer by electrospray, during the whole period of injection samples were maintained at 10° C. Mass spectrometry was performed on an Agilent 6530 Accurate Mass Q-TOF mass spectrometer operating in positive ion mode with 2 GHz extended dynamic range mode. Mass scan was performed with Nebulizer pressure 40 psi, Capillary voltage 4000V, Nozzle voltage 500V and fragmentation voltage 170V, mass range selected were 50-1100. 121 m/z and 922 m/z were used as reference ion for accurate mass calibration.

Mass spectrometric data analysis was performed using Mass Profiler Professional (MPP) version 2.1 (Agilent Technologies, Santa Clara, Calif.). The metabolic data was grouped based on their hierarchical levels and used as input for MPP. The preprocessing steps of filtering, normalization and averaging were then performed to minimize instrument errors and remove noise. Hierarchical clustering based on Euclidean distance matrix was performed on the dataset to help visualize the relative abundance of ions and clustering of cell lines. Principal Components Analysis (PCA) was used to establish the similarity between replicates based on metabolite profiles. Differential ions were then identified by performing two-tailed t-test and filtering with a P value cutoff of <0.05. The list of ions after t-test and fold change filtering were identified as having a significant difference in the metabolite levels. Unique non ambiguous metabolites were identified using HMDB (Human Metabolome Database http://www.hmdb.ca/). All the non-ambiguous metabolites were also confirmed through MS2 fragmentation. MS2 fragmentation was done using ABI 4000 Q-Trap with delustering potential (DP), 81V, collision energy (CE), 35V, Ion source temperature 250 C and Ion source voltage 440V. These metabolites were then mapped onto metabolic pathway maps in KEGG using MetDAT (Biswas, A., Mynampati, K. C., Umashankar, S., Reuben, S., Parab, G., Rao, R., Kannan, V. S., and Swamp, S. (2010). MetDAT: a modular and workflow-based free online pipeline for mass spectrometry data processing, analysis and interpretation. Bioinformatics 26, 2639-2640).

Western Blot

Samples were separated by SDS-PAGE and transferred on PVDF membrane (100V at 4° C. during 2 Hr). Membranes were blocked in TBST-5% milk 1 Hr at RT. Anti-PSPH (Sigma), β-Actin (Santa Cruz), LIN28B (Cell Signaling), c-Fos (Cell Signaling), CDK1 (Santa cruz), Hsp90 (BD biosciences) and anti-GLDC (Abcam) primary antibodies at 1:1000 were used (1 Hr at RT). β-Actin or Hsp90 was used as a loading control. Membranes were washed 5× in TBST and incubated 1 Hr with goat anti-rabbit or donkey anti-goat IgG secondary antibodies HRP-conjugated (Santa Cruz) at 1:5000. After washing in TBST, proteins were detected using ECL Plus™ Western Blotting (GE Healthcare).

Cell Synchronization by Serum Starvation

Normal human adult lung fibroblasts or cancer cell line A549 cells were serum starved (in 0.1% serum) for 72 hours followed by release into serum-containing medium with samples collected at indicated time points, namely 0, 1, 2, 4, 8, 16, 24 and 48 hours. Normal growing, unsynchronized cells (Cyc) were used as a control. We tested the expression of GLDC, c-Fos (an early serum response gene) and Cdk1 (an E2F target gene and a marker of cells in late S-phase).

Tissue Microarray

A tissue microarray (TMA) was constructed as previously described (Kristiansen et al., 2001). GLDC, CD166 and LIN28B staining was independently scored by two anatomical pathologists (M.E.N, Y.H.P). Staining intensity was scored semi-quantitatively (score 0: very weak staining; 1+: weak staining; 2+: moderate staining; 3+: strong staining).

Flow Cytometry

A list of antibodies used can be found in Table 7. Cells were FACS-sorted using a FACSAria (BD). Flow cytometry was performed using a LSR II flow cytometer, and data was analyzed with CELLQuest Pro software (BD).

TABLE 7

List of antibodies

| Antibody | Clone | Source | Application |
|---|---|---|---|
| CD166-PE | 105902 | R&D | FACS |
| CD133/1-APC/PE | AC133 | Miltenyi Biotech | FACS |
| CD133/2-APC/PE | 293C3 | Miltenyi Biotech | FACS |
| EpCAM-FITC/APC/PE | HEA-125 | Miltenyi Biotech | FACS |
| CD44-FITC | G44-26 | BD PharminGen | FACS |
| CD31-FITC | HC1/6 | Biosource | FACS |
| CD45-FITC | HI30 | BD PharminGen | FACS |
| CD34-FITC | AC136 | Miltenyi Biotech | FACS |
| mouse MHC-I-FITC (mouse H-2K$^d$-FITC) | SF1-1.1 | BD Biosciences | FACS |
| mouse CD45-FITC | 30-F11 | BD PharminGen | FACS |

TABLE 7-continued

List of antibodies

| Antibody | Clone | Source | Application |
|---|---|---|---|
| amino-actinomycin D (7-AAD) | | BD PharminGen | FACS |
| isotype antibodies | | BD PharminGen | FACS |
| CD166 | 105902 | R&D | IF (1:100) |
| CD166 | H-108 | Santa Cruz | IF (1:100) |
| CD166 | MOG/07 | Novaocastra | IHC (1:100) |
| pan cytokeratin | AE1/AE3 | Zymed | IHC (1:200) |
| GLDC | | Sigma | IHC (1:25) |
| GLDC | | Abcam | WB (1:1000) |
| LIN28B | | Abgent | IHC (1:100) |
| LIN28B | | Cell signaling | WB (1:1000) |
| E-cadherin | NCH-38 | Dako | IHC (1:50) |
| Smooth muscle antigen (SMA) | 1A4 | Dako | IHC (1:50) |
| Synaptophysin (SYP) | SY38 | Dako | IHC (1:10) |
| Vimentin | V9 | Dako | IHC (1:50) |
| PSPH | | Sigma | WB (1:1000) |
| CDK1 | | Santa Cruz | WB (1:1000) |
| c-fos | | Cell signaling | WB (1:1000) |
| □-actin | | Santa Cruz | WB (1:1000) |
| Hsp90 | | BD Biosciences | WB (1:1000) |
| Envision HRP Polymer System | | Dako | IHC |
| Anti-rabbit IgG Alexa Fluor 488/568 | | Invitrogen | IF (1:1000) |
| Anti-mouse IgG Alexa Fluor 488/568 | | Invitrogen | IF (1:1000) |
| Goat anti-rabbit IgG-HRP | | Santa Cruz | WB (1:5000) |
| Donkey anti-goat IgG-HRP | | Santa Cruz | WB (1:5000) |

Animals and Transplantation of Tumor Cells

NOD.Cg-Prkdc$^{scid}$ Il2rg$^{tm1Wjl}$/SzJ mice (Jackson Laboratories) at 4-6 weeks old were subcutaneously transplanted with single cell suspensions in serum-free medium and Matrigel (BD) (1:1).

Tumor Sphere Culture

Cells were grown in DMEM/F12 containing ITS (BD Biosciences) and supplemented with 50 ng/ml EGF and 20 ng/ml bFGF (Invitrogen), using non-treated cell culture plates (Nunc). Fresh medium was replenished every 3 days.

Statistical Analysis

Differences were compared using two-tailed Student t-test. P values <0.05 were considered statistically significant. All analyses were performed with SPSS 18.0 (SPSS). Lung TIC frequencies were estimated using ELDA software (Hu and Smyth, 2009). Fisher's exact test was used to assess the association between GLDC, CD166 or LIN28B and clinicopathological parameters. The effect of GLDC, CD166 or LIN28B expressions on lung cancer mortality was modelled using competing risks regression, and quantified based on the subdistribution hazard ratio (SHR) (Fine and Gray, 1999).

Accession Numbers

The GEO accession number for human datasets is GSE33198.

Over Expression of GLDC in Cells Induces Tumorigenesis

Figure 1:
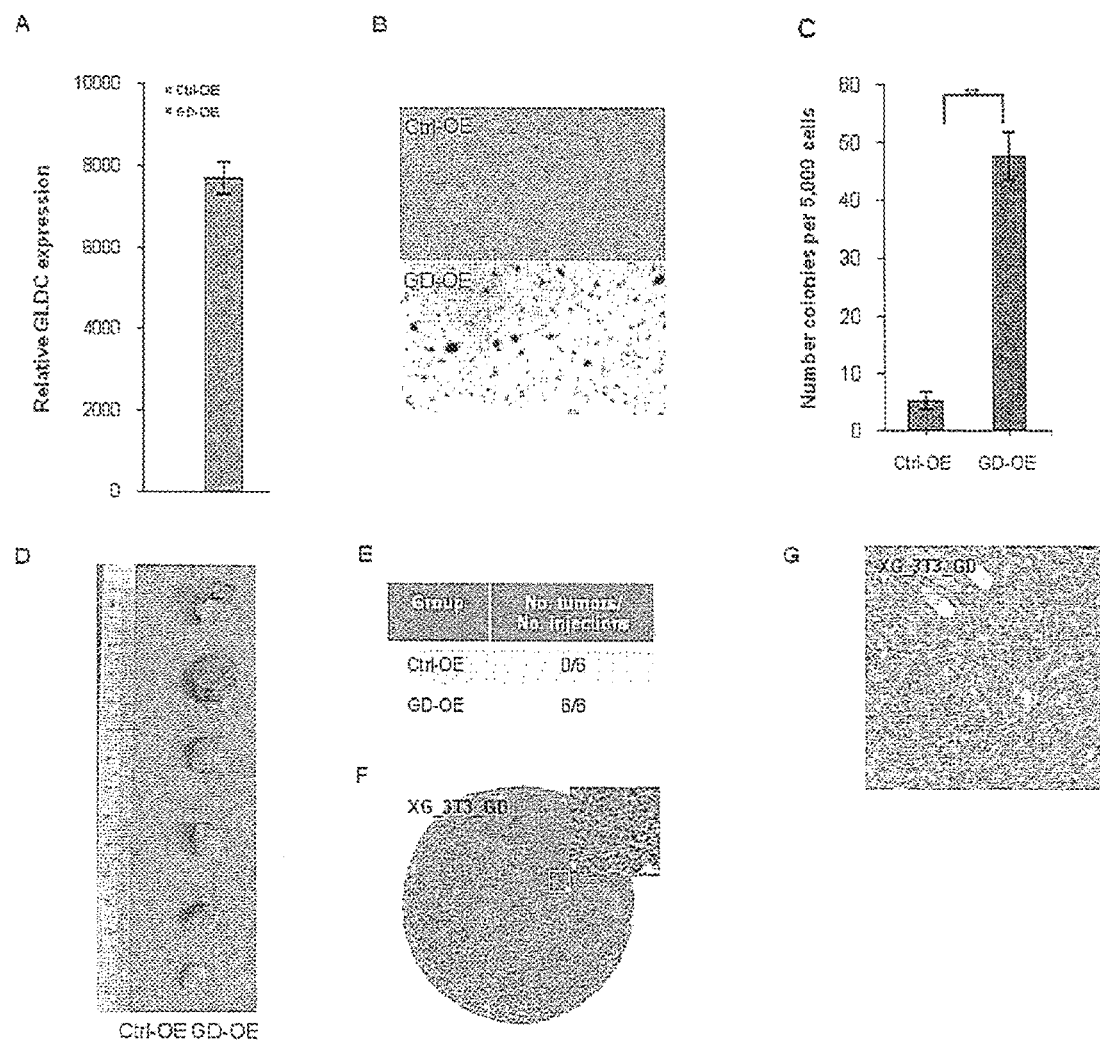
FIG. 1 GLDC transform NIH/3T3 cells.

The GLDC level in different normal cells varies from low to high expression (data not shown). Normal cells such as lung and skin cells have low levels of expression while other normal cells such as Germ Cells, Liver, and Neurons have higher levels of GLDC. For those low/negative expressing normal cells, over-expression of GLDC was demonstrated to lead to transformation such as shown in FIG. 1 in lung fibroblasts.

Most cells express low levels of GLDC. The highest expressing normal cells are liver, germ cells, brain. The levels of GLDC in these normal cells are close to that in cancer cell lines. Compared to normal cells that have low levels of GLDC, tumor cells have about 2-10x higher levels of GLDC Expression of GLDC in Human Primary Cancer Samples and Cancer Cell Lines FIG. 2 shows expression of GLDC in various tissues on tumor and normal samples. The expression of GLDC ranges from 1.5 to 16 times higher in cancer versus normal counterparts in some types of cancer, such as ovary, cervix, germ cell, esophagus, lung cancer, etc. However, for some types of cancer, such as liver, kidney, melanoma etc, the expression of GLDC is lower (⅛-½) in tumor versus normal counterparts. According to our screen of high GLDC expression in tumors versus normal tissues, a wide range of tumors express high levels of GLDC, such as cancer cells of ovary, cervix, germ cell, esophagus, and lung cancer. We will test if suppression of GLDC in these cancers is also inhibitory to tumor growth.

Table 1 outlines a statistical comparison between tumor verses normal cells. Whereby a higher percentage is indicative of over expression in cancer cells as compared with normal cells of that cell type.

TABLE 1

Detailed statistics about GLDC expression intensity on tumor cell lines.

| Organ | Total number of tumor cell lines | Number of cell lines with high GLDC expression | Percentage of high GLDC (%) |
|---|---|---|---|
| Germ line | 8 | 5 | 62.5 |
| Liver | 7 | 4 | 57.1 |
| Cervix | 9 | 5 | 55.6 |
| Brain | 4 | 2 | 50 |
| Ovary | 27 | 13 | 48.1 |
| Kidney | 58 | 24 | 41.4 |
| Breast | 51 | 18 | 29.5 |
| Gastric | 38 | 11 | 28.9 |
| Lung | 132 | 38 | 28.8 |
| Skin | 32 | 7 | 21.9 |
| Blood | 55 | 14 | 21.5 |
| Head and Neck | 5 | 1 | 20 |
| Pancreas | 23 | 4 | 17.4 |

TABLE 1-continued

Detailed statistics about GLDC expression intensity on tumor cell lines.

| Organ | Total number of tumor cell lines | Number of cell lines with high GLDC expression | Percentage of high GLDC (%) |
|---|---|---|---|
| Prostate | 21 | 3 | 14.5 |
| Colon | 76 | 6 | 7.9 |
| Bladder | 40 | 3 | 7.5 |
| Total | 606 | 158 | 26.1 |

Decrease in GLDC Levels Reduce Tumorigenicity.

Knockdown GLDC inhibit the malignant growth of tumorigenic ALCAM⁺ sphere cells (FIG. 7).

TABLE 2

Summary of GLDC tissue distribution in tumor and normal ones.

| GLDC expression level | | |
|---|---|---|
| Tumor | Normal | Tumor types |
| **** | *̂ | Lung cancer - adenocarcinoma: squamous cell carcinoma; large cell carcinoma<br>Uterus cervical squamous cell carcinoma<br>Esophagus squamous carcinoma<br>Pancreas cancer<br>Epiploon metastatic mucinous adenocarcinoma |
| **** | * | Prostate adenocarcinoma<br>Stomach Adenocarcinoma |

Screening for Molecular Inhibitors Against GLDC

We have identified lead compounds such as structures similar to Victorin and are screening the same with cell line assays.

Inhibitors can be Used in Combination with Other Chemotherapeutic Agents

The screening of small molecular inhibitors against GLDC is ongoing. Candidate small molecules can be used in combination with routine chemotherapeutic agents. One important mechanism of these inhibitors may be, in combination with other chemotherapeutic agents, The GLDC inhibitor may eliminate chemoresistant tumor initiating cells and allowing chemotherapeutic agent to the kill the remaining tumor cells.

Onco-Induction Potential of GLDC

Over-expression of GLDC lead to transformation from lung fibroblasts to tumerogenic cells. Similarly, in other cell lines exogenic over expression of GLDC can lead to bladder cancer in bladder cells, breast cancer in breast cells, pancreatic cancer in pancreatic cells, brain tumors, lymphomas, gliomas, melanomas, or leukemias.

Results

Measurement and or Isolation and or Enrichment of Tumour Initiating Cells in Lung Cancer To assess the cellular heterogeneity within non-small cell lung cancer (NSCLC), we obtained freshly resected lung tumors from 36 human patients with a broad range of stage I-III primary NSCLC (Table 3). Patient lung cancer cells were directly transplanted subcutaneously into NOD/SCID Il2ry⁻/⁻ mice with Matrigel (Quintana et al., 2008). Using this maximally sensitive assay, we estimated by limiting dilution analysis that lung TICs exist with a low frequency of 1 in $4 \times 10^5$ cells in unsorted NSCLC tumor cells (n=36 patients; FIG. 8A).

TABLE 3

Patient characteristics for xenotransplantation assays (n = 36 tumors and 10 normal lung tissues), Related to FIG. 1

| Patient no. | Sex | Age | Organ | Pathology diagnosis | Stage | pTNM |
|---|---|---|---|---|---|---|
| LCP15 | M | 67 | Lung | AdC | IIB | pT2N1M0 |
| LCP16 | M | 70 | Lung | AdC | IIIA | pT4N0M0 |
| LCP22 | F | 47 | Lung | AdC | IB | pT2N0Mx |
| LCP29 | M | 60 | Lung | AdC | IIIA | pT1N2M0 |
| LCP32 | F | 55 | Lung | AdC | IA | pT1N0M0 |
| LCP36 | F | 67 | Lung | AdC | IA | pT1N0M0 |
| LCP38 | F | 73 | Lung | AdC | IB | pT2N0M0 |
| LCP39 | F | 51 | Lung | AdC | IB | pT2N0M0 |
| LCP40 | F | 71 | Lung | AdC | IB | pT2N0M0 |
| LCP42 | M | 75 | Lung | AdC | IIB | pT2N0M0 |
| LCP43 | M | 55 | Lung | AdC | IIA | pT1N1M0 |
| LCP44 | F | 60 | Lung | AdC | IIA | pT1N1M0 |
| LCP45 | F | 52 | Lung | AdC | IA | pT1N0Mx |
| LCP46 | F | 35 | Lung | AdC | IIB | pT2N1M0 |
| LCP49 | F | 48 | Lung | AdC | IIIA | pT2N2M0 |
| LCP50 | F | 60 | Lung | AdC | IIIB | pT4N2M0 |
| LCP51 | M | 66 | Lung | AdC | IIIA | pT2N2Mx |
| LCP52 | M | 78 | Lung | AdC | IA | pT1N0Mx |
| LCP53 | F | 56 | Lung | AdC | IIIA | pT1N2M0 |
| LCP55 | F | 44 | Lung | AdC | IIIA | pT1N2Mx |
| LCP56 | M | 69 | Lung | AdC | IA | pT1N1M0 |
| LCP57 | F | 62 | Lung | AdC | IA | pT1N0M0 |
| LCP58 | F | 54 | Lung | AdC | IA | pT1N0M0 |
| LCP59 | F | 67 | Lung | AdC | IIB | pT2N1M0 |
| LCP60 | F | 63 | Lung | AdC | IA | pT1N0M0 |
| LCP61 | M | 78 | Lung | AdC | IA | pT1N0Mx |
| LCP62 | F | 49 | Lung | AdC | IIIB | pT4N0Mx |
| LCP72 | M | 50 | Lung | AdC | IIB | pT2N1Mx |
| LCP73 | F | 72 | Lung | AdC | IA | pT1N0Mx |
| LCP34 | M | 75 | Lung | SCC | IIIA | pT2N2M0 |
| LCP41 | M | 65 | Lung | SCC | IB | pT2N0M0 |
| LCP54 | M | 74 | Lung | SCC | IB | pT2N0M0 |
| LCP64 | M | 54 | Lung | SCC | IB | pT2N0Mx |
| LCP27 | M | 60 | Lung | LCC | IIB | pT2N1M0 |
| LCP30 | M | 55 | Lung | LCC | IIIB | pT4N2M0 |
| LCP70 | M | 26 | Lung | Mucoepidermoid carcinoma | IB | pT2N0M0 |
| LNP28 | M | 58 | Lung | Non-neoplastic lesion | — | — |
| LNP33 | M | 76 | Lung | Non-neoplastic lesion | — | — |
| LNP16 | M | 70 | Lung | Cancer adjacent normal lung tissue | — | — |
| LNP22 | F | 47 | Lung | Cancer adjacent normal lung tissue | — | — |
| LNP29 | M | 60 | Lung | Cancer adjacent normal lung tissue | — | — |
| LNP56 | M | 69 | Lung | Cancer adjacent normal lung tissue | — | — |
| LNP57 | F | 62 | Lung | Cancer adjacent normal lung tissue | — | — |
| LNP34 | M | 75 | Lung | Cancer adjacent normal lung tissue | — | — |
| LNP54 | M | 74 | Lung | Cancer adjacent normal lung tissue | — | — |
| LNP27 | M | 60 | Lung | Cancer adjacent normal lung tissue | — | — |

Note:
LCP, lung cancer patient;
LNP, lung normal patient;
AdC, lung adenocarcinoma;
SCC, squamous cell carcinoma;
LCC, large cell carcinoma;
pTNM, primary tumor (T), regional lymph nodes (N), distant metastasis (M).

To profile the surface phenotype of this subpopulation of lung TICs, we fractionated the NSCLC tumors by fluorescence-activated cell sorting (FACS; FIG. 15A). After excluding hematopoietic and endothelial cells (Lid), we tested a panel of cell surface markers, including CD166, CD44, CD133, and EpCAM (FIG. 8B). We found that CD166 was the most robust marker for enriching the lung TIC subpopulation, compared to CD133, CD44 or EpCAM, allowing us to reliably enrich lung TICs by nearly 100-fold (FIG. 8A-B). In twelve out of twelve NSCLC patient tumors (lung adenocarcinoma), the CD166$^+$Lin$^-$ fraction contained cells that consistently initiated lung tumor formation in vivo. In contrast, CD166$^-$Lin$^-$ tumor cells generally failed to initiate lung tumor formation even after 8 months of observation, although they also express carcinoembryonic antigen (CEA), a tumor-specific marker not expressed in normal adult lung cells (FIG. 8A-B; FIG. 15B). Similar results were observed in lung squamous cell carcinoma and large cell carcinoma (FIG. 15C). Although CD166 expression varied across the NSCLC tumors we examined, CD166 was consistently higher in lung tumors than normal adjacent lung tissues (n=25 patients; FIG. 15D-E).

CD166$^+$ lung TICs demonstrate a capacity for self-renewal and differentiation in vivo. Serial transplantations showed that only the CD166$^+$ fraction was able to self-renew and initiate primary and secondary xenograft tumors (FIG. 8A; FIG. 15F). Upon transplantation, CD166$^+$ lung TICs differentiated to form xenograft tumors that phenocopy the complex cytoarchitecture of their parental patient tumors, sharing similar histological morphology by hematoxylin-eosin (H&E) staining and similar tissue distributions of CD166, cytokeratin, E-cadherin, vimentin, smooth muscle actin, and synaptophysin (FIG. 8C; FIG. 15G-H). Furthermore, we found that transplants with more TICs grow more rapidly, suggesting that lung TIC frequency is correlated with tumor growth rate (FIG. 8D; FIG. 15I).

The self-renewal capacity of CD166$^+$ lung TICs is further corroborated by in vitro assays. We tested the CD166$^+$ fraction for the ability to form tumor spheres, a widely used in vitro technique for assessing self-renewal capacity. Although both primary CD166$^+$ and CD166$^-$ cells remained viable in vitro, only primary CD166$^+$ but not CD166$^-$ cells were able to form compact self-renewing spheres (n=9 patients; FIGS. 8E-F; FIG. 15J). Using immunofluorescence and flow cytometry, we found that the lung tumor spheres retained high levels of CD166 expression, but undetectable CD133 expression in contrast (FIGS. 15K-L). When primary lung tumor spheres were dissociated into single cells and transplanted into NOD/SCID Il2ry$^{-/-}$ mice in vivo, we found that as few as 1-5 single cells consistently initiated tumorigenesis (FIG. 8G; FIG. 15M).

The increased tumor-initiating frequency of lung tumor sphere cells suggests they are even more highly enriched for lung TICs than the patient tumor CD166$^+$ fraction, and that lung TICs expanded during in vitro culture to form tumor spheres. To test if CD166 serves drives tumorigenicity in lung TICs, we knocked down CD166 in two lines of NSCLC patient-derived tumor spheres by retroviral shRNA (FIG. 15N). We found that the tumorigenicity of lung TICs in the tumor spheres was not significantly affected by CD166 shRNA, demonstrating that CD166 is an inert cell surface marker that enriches for lung TICs (FIGS. 15O-Q).

Lung TICs Express High Levels of Glycine/Serine Metabolism Enzymes

To gain a deeper understanding of the molecular basis for the TIC state and its tumorigenic capacity, we sought to obtain a molecular signature for lung TICs. To do this, we performed genome-wide transcriptome analysis on CD166$^-$Lin$^-$ tumor cells, CD166$^+$ Lin$^-$ tumor cells, and lung tumor spheres, in increasing order of lung TIC frequency (FIG. 9A). As a negative control, we also profiled CD166$^+$ vs. CD166$^-$ cells from normal adjacent lung tissues (n=3 patients; Table 3). This led us to a profile of genes that are upregulated and downregulated in lung TICs, compared to non-TICs (FIG. 9B). Lung TIC-associated genes include the oncogenic stem cell factor LIN28B, embryonic lung transcription factors like PEA3 and the trachealess homolog NPAS1, as well as cell-cycle regulators like CCNB1 and GADD45G (FIG. 9C). The highest-ranking genes were validated by qRT-PCR (FIG. 16A). KEGG pathway analysis of the lung TIC-gene profile showed that the top enriched pathways were "cell cycle", "DNA replication", "glycine, serine and threonine metabolism", "pyrimidine metabolism", "MAPK signaling pathway" and "p53 signaling pathway" (FIG. 9D). Within the glycine, serine and threonine metabolism pathway, we found that glycine/serine metabolism enzymes like glycine decarboxylase GLDC, glycine C-acetyltransferase GCAT, serine hydroxymethyltransferase SHMT1, phosphoserine phosphatase PSPH, and phosphoserine aminotransferase PSAT1, were all upregulated in lung TICs (FIG. 9E; FIG. 16B-D). In particular, GLDC was one of the most highly upregulated genes in multiple analyses of lung TIC-enriched populations, both at the mRNA and protein level (FIG. 9C; FIG. 16C). GLDC is a key component of the highly conserved glycine cleavage system in amino acid metabolism that catalyzes the breakdown of glycine to form $CO_2$, $NH_3$ and 5,10-methylene-tetrahydrofolate ($CH_2$-THF) to fuel one-carbon metabolism.

GLDC is an Oncogene that Promotes Tumorigenesis and Cellular Transformation

High expression of GLDC and LIN28B in lung TIC-enriched populations, but not in CD166$^-$ lung cancer cells and CD166$^+$ normal lung cells, suggests that these 2 genes drive tumorigenicity in lung TICs. To test this hypothesis, we knocked down GLDC and LIN28B in lung tumor spheres with shRNAs (FIG. 17A), and compared their growth both in vitro and in vivo. We found that both GLDC and LIN28B were necessary for cell proliferation in sphere culture, as well as anchorage-independent colony formation in soft agar (FIG. 10A; FIG. 17B). Importantly, tumorigenicity was also significantly reduced upon knockdown of either GLDC or LIN28B (FIG. 10B; FIG. 17C). A549 lung adenocarcinoma cells showed similar results (FIGS. 17D-G). Our results suggest that lung tumor initiating cells and lung tumorigenesis are dependent on the glycine decarboxylase enzyme GLDC. This led us to ask what oncogenes upregulate GLDC. Since the E2F pathway upregulates many metabolic genes during cell proliferation, we examined the expression of GLDC over the course of the cell-cycle in both normal human lung fibroblasts (HLF) and the transformed A549 cells after synchronization by serum-starvation. Our results showed that GLDC is insensitive to cell-cycle progression in both normal HLFs and transformed A549 cells, suggesting that GLDC is not regulated by cell-cycle or E2F signals (FIG. 10C). We then examined GLDC levels in MCF10A cells after transformation by oncogenic KRAS$^{G12D}$, PIK3CA$^{E545K}$, and MYC$^{T58A}$. Our results show that all 3 oncogenes induce GLDC by ~20-fold, suggesting that oncogene-induced GLDC transcription is common to the cellular transformation process mediated by oncogenic Ras, PI3K and Myc (FIG. 10D).

To test if aberrant GLDC upregulation is sufficient to drive cellular transformation we overexpressed GLDC in NIH/3T3 cells (FIG. 17H). We found that GLDC overexpression significantly increased colony formation by 3T3 cells under normal culture conditions (FIGS. 10E-F). To test for cellular transformation in vitro, we cultured the 3T3 cells overexpressing GLDC under anchorage-independent conditions, and found that GLDC transforms 3T3 cells readily with a rate exceeding that of LIN28B (FIG. 10G; FIG. 17I). Upon transplantation into NOD/SCID Il2ry$^{-/-}$ mice, 3T3 cells overexpressing GLDC consistently formed tumors in 6/6 transplants, and 3T3 cells overexpressing LIN28B formed tumors in 3/6 transplants, whereas 3T3 cells overexpressing the empty control vector never formed tumors (FIGS. 17J-L).

To test if GLDC can also transform normal primary human lung fibroblasts (HLF) and normal primary human bronchial epithelial cells (NHBE), we overexpressed GLDC in HLF and NHBE cells (Figure S3M, S3O). Both HLF and NHBE cells showed a dramatic increase in cell proliferation upon overexpression of GLDC alone (FIGS. 10H-J; FIG. 17P). Surprisingly we found that GLDC also transforms HLF and NHBE cells readily in vitro (FIG. 10K; FIG. 17Q). However, perhaps because primary adult HLF and NHBE cells are not immortalized, GLDC-overexpressing HLF and NHBE cells do not form tumors upon transplantation (FIG. 17N, 17R). In contrast CD166⁻ lung tumor cells, which also could not form tumors in vivo, could now initiate tumorigenesis at a low frequency upon overexpression of GLDC (FIG. 10L). Collectively, our results show that GLDC is an oncogene that is both necessary and sufficient to promote tumorigenesis.

GLDC Promotes Tumorigenesis Through its Metabolic Activity

Although GLDC is a metabolic enzyme, it remained unclear whether GLDC promotes tumorigenesis through a metabolism-dependent or -independent mechanism. To address this question, we engineered a series of 4 point mutations within or near the evolutionarily-conserved catalytic active site of the GLDC enzyme, to disrupt its metabolic activity (FIG. 11A). These point mutations comprised 3 non-lethal GLDC mutations found in human patients with nonketotic hyperglycinemia (H753P, P769L, G771R; FIG. 18A-B), and 1 mutation K754A that is predicted to abrogate the covalent bond with the critical pyridoxal-5'-phosphate cofactor. When we overexpressed these 4 GLDC mutants in 3T3 cells, none of them could lead to tumorigenesis in vivo, whereas wild-type GLDC could, even though all of them were expressed at high levels similar to that in transformed A549 cells (FIG. 11B). Thus the metabolic activity of GLDC is required for its tumorigenic function.

In addition, the upregulation of many other upstream enzymes in the glycine/serine pathway in lung TICs further supports the idea that metabolic activity in the glycine/serine pathway is responsible for promoting tumorigenesis (FIG. 9E). To test this idea, we also overexpressed PSAT1, PSPH, SHMT1, SHMT2, and GCAT in 3T3 cells, and transplanted them in vivo to test for cellular transformation and tumorigenesis (FIG. 11C). By 2 months we found that 3 other glycine/serine enzymes—PSAT1, PSPH and SHMT2—could also transform 3T3 cells to form tumors in vivo (FIG. 11D). Interestingly, we noted that PSAT1, PSPH and SHMT2 overexpression only led to a slight upregulation of GLDC protein (FIG. 11E), suggesting that their tumorigenic activity is due to increased glycine/serine metabolism, rather than indirect upregulation of GLDC. These findings indicate that increased metabolism in the glycine/serine pathway due to GLDC or other glycine/serine enzymes can exert a potent tumorigenic effect.

GLDC Regulates Glycine Metabolism, with Effects on Glycolysis and Pyrimidines

Given that GLDC promotes tumorigenesis through a metabolism-dependent mechanism, we performed metabolomic analysis to gain deeper mechanistic insights into the GLDC-driven metabolism changes that lead to tumorigenesis. Using liquid chromatography-mass spectrometry (LC-MS), we performed metabolomics profiling of HLF cells and 3T3 cells overexpressing GLDC, as well as A549 lung adenocarcinoma cells with retroviral knockdown of GLDC, relative to empty vector controls. We found that glycine-related metabolites, glycolysis intermediates and many pyrimidines were significantly perturbed by both GLDC overexpression and knockdown ($P<0.05$, FIG. 12A-D). For glycine-related metabolites, we found that sarcosine (N-methylglycine) levels increased significantly upon GLDC overexpression and dropped significantly upon GLDC knockdown, indicating that GLDC is promoting sarcosine synthesis or accumulation (FIG. 12A). Consistent with this observation, betaine aldehyde in the betaine-sarcosine-glycine pathway for glycine synthesis also showed the same pattern of changes (FIG. 12A). Glycine levels decrease with GLDC overexpression and increase with GLDC knockdown, in agreement with the fact that GLDC breaks down glycine irreversibly. In contrast, serine levels increase with GLDC overexpression and decrease with GLDC knockdown, suggesting that GLDC is promoting serine synthesis or uptake (FIG. 12A).

Surprisingly, GLDC perturbation also led to dramatic changes in glycolysis, and other amino acids (FIGS. 12B-C; FIG. 19A). Our data suggests that GLDC is promoting glycolysis, leading to the increased synthesis or accumulation of glucose-1-phosphate, phosphoenolpyruvate, pyruvate and lactate (FIG. 12B-C). In fact many of the upstream glycine/serine metabolism enzymes that we found upregulated in lung TICs, such as PSAT1, PSPH and SHMT1/2, channel glycolytic intermediates into de novo serine and glycine biosynthesis (FIG. 9E), suggesting that GLDC is working in a concerted fashion with these enzymes to promote the glycolysis-serine-glycine flux. This is supported by our finding that GLDC does not significantly promote glycine uptake (FIG. 19B-C), but promotes glycolysis instead (FIG. 12B-C).

Finally, our metabolomics analysis also revealed that GLDC promotes the synthesis or accumulation of pyrimidines, including thymidine, deoxyuridine, thymine, uracil and cytosine (FIG. 12D). The GLDC-catalyzed reaction converts glycine into $CH_2$-THF. $CH_2$-THF contains the methylene group that fuels de novo thymidine synthesis from deoxyuridine in concert with pyrimidine biosynthesis and hence nucleotide synthesis during cell proliferation. Our observations on pyrimidine synthesis suggest that upregulation of GLDC could promote cellular transformation by overcoming nucleotide deficiency that has been observed in early oncogenesis to progress onwards in early oncogenesis.

To test if any of the metabolite changes induced by GLDC can mimic GLDC's effects on cancer cells, we analyzed whether an increased exogenous supply of specific metabolites could rescue GLDC retroviral knockdown in A549 cells. We found that 10 µM of sarcosine could significantly rescue the proliferation defect upon GLDC knockdown, with little effect on control A549 cells (FIG. 12F), indicating that increased sarcosine-glycine metabolite flux can rescue the effects of reduced GLDC enzyme. To further test if the production of $CH_2$-THF is necessary for GLDC's effects on proliferation, we tested whether the anti-folate drug methotrexate could specifically abrogate GLDC-induced proliferation by reducing the tetrahydrofolate (THF) cofactor needed to produce $CH_2$-THF for pyrimidine synthesis. Our results show that low doses of methotrexate specifically abrogated GLDC-induced proliferation in 3T3 and HLF cells, with little effects on control 3T3 and HLF cells (FIG. 12E). Furthermore, methotrexate in combination with GLDC shRNA killed transformed A549 cells much more effectively than either alone (FIG. 12E), suggesting that a combination of anti-folates with a GLDC inhibitor could completely shut off glycine catabolism to treat cancer cells more effectively. Using these metabolic data, we constructed a model of how aberrant GLDC expression might reprogram glycolysis and glycine metabolism fluxes in cancer cells to promote cancer cell proliferation and tumorigenesis (FIG. 12G).

Prognostic Significance of Aberrant GLDC Expression in NSCLC Patients

To assess if our experimental findings on GLDC are relevant to human lung cancer patients in the clinic, we examined the prognostic significance of GLDC expression, tumor size, tumor grade, and cancer stage in clinical tumor samples from cohorts of NSCLC patients (n=143) using tissue staining results inconclusive (FIG. 20E). Our immunohistochemistry results on clinical tumor samples are consistent with the idea that lung TICs constitute the bulk of the tumors in late stages of malignancy, and demonstrate that aberrant activation of GLDC is significantly associated with human mortality in NSCLC patients—further supporting its role as a metabolic oncogene in human NSCLC.

TABLE 4

Clinical pathologic characteristics of NSCLC patients and their association with GLDC staining intensity grade (n = 143), Related to FIG. 6

| Characteristics | Total | GLDC intensity | | | | P-value |
| --- | --- | --- | --- | --- | --- | --- |
| | | 0 | 1+ | 2+ | 3+ | |
| Total no. | 143 | 59 | 49 | 15 | 20 | |
| Histology (%) | | | | | | 0.03 |
| Adenocarcinoma | 97 (68) | 40 (68) | 39 (80) | 6 (40) | 12 (60) | |
| Squamous cell Carcinoma | 46 (32) | 19 (32) | 10 (20) | 9 (60) | 8 (40) | |
| Mean tumor size (cm) (SD) | 3.79 (2.02) | 3.76 (2.04) | 3.42 (1.98) | 4.91 (1.97) | 3.99 (1.88) | 0.108 |
| T stage (%) | | | | | | 0.478 |
| T1 | 33 (24) | 19 (34) | 8 (17) | 2 (13) | 4 (25) | |
| T2 | 71 (16) | 27 (48) | 24 (52) | 10 (67) | 10 (50) | |
| T3 | 16 (12) | 5 (9) | 6 (13) | 1 (7) | 4 (20) | |
| T4 | 16 (12) | 5 (9) | 8 (17) | 2 (13) | 1 (5) | |
| N stage (%) | | | | | | 0.395 |
| N0 | 104 (76) | 47 (85) | 34 (72) | 9 (60) | 14 (74) | |
| N1 | 19 (14) | 4 (7) | 8 (17) | 4 (27) | 3 (16) | |
| N2 | 12 (9) | 4 (7) | 4 (9) | 2 (13) | 2 (11) | |
| N3 | 1 (1) | 0 (0) | 1 (2) | 0 (0) | 0 (0) | |
| M stage (%) | | | | | | 0.112 |
| M0 | 132 (97) | 55 (100) | 44 (94) | 14 (93) | 19 (100) | |
| M1 | 4 (3) | 0 (0) | 3 (6) | 1 (7) | 0 (0) | |
| AJCC stage (%) | | | | | | 0.141 |
| I | 81 (61) | 40 (74) | 24 (52) | 7 (50) | 10 (53) | |
| II | 24 (18) | 5 (9) | 9 (20) | 3 (21) | 7 (37) | |
| III | 23 (17) | 8 (15) | 10 (22) | 3 (21) | 2 (11) | |
| IV | 5 (4) | 1 (2) | 3 (7) | 1 (7) | 0 (0) | |
| Grade (%) | | | | | | 0.326 |
| Well-differentiated | 9 (6) | 5 (9) | 3 (6) | 0 (0) | 1 (5) | |
| Moderately differentiated | 74 (53) | 34 (59) | 25 (52) | 8 (53) | 7 (37) | |
| Poorly differentiated | 46 (33) | 16 (28) | 13 (27) | 7 (47) | 10 (53) | |
| Undifferentiated | 11 (8) | 3 (5) | 7 (15) | 0 (0) | 1 (5) | |
| Status (%) | | | | | | 0.247 |
| Alive | 66 (46) | 31 (53) | 24 (49) | 6 (40) | 5 (25) | |
| Lung cancer related death | 63 (44) | 21 (36) | 21 (43) | 7 (47) | 14 (70) | |
| Non-lung cancer related death | 14 (10) | 7 (12) | 4 (8) | 2 (13) | 1 (5) | | microarray immunohistochemistry (FIG. 13A; FIG. 20; Table 4). Subdistribution hazard ratio (SHR) analysis showed that patients with high or grade 3+ GLDC expression have a three-fold higher risk of lung cancer mortality compared to patients with low or grade 0 GLDC expression, even when adjusted for cancer stage (SHR=3.01, 95% CI: 1.48-6.10, P=0.002) (FIG. 13B). Cumulative mortality analysis also showed that high GLDC expression (grade 3+) is significantly associated with higher cumulative incidence of mortality across 143 NSCLC lung cancer patients, even when adjusted for cancer stage (P=0.005) (FIG. 13C). CD166 expression was not significantly associated with higher mortality in lung cancer patients—which was not unexpected given that only 1 in 5×10³ CD166+ cells are tumorigenic (FIG. 20A-C). Indeed, co-immunostaining of lung tumors revealed that GLDC+ cells mostly form a subset of CD166+ cells, and that not all CD166+ cells are GLDC+ (FIG. 13D; FIG. 20D). LIN28B immunohistochemistry was also not significantly correlated with lung cancer patient mortality (FIG. 20A-C), although Western blots revealed that lung TICs express a second LIN28β isoform that is indiscernible from immunohistochemistry staining, thus rendering our LIN28B Aberrant GLDC Expression in Other Cancers To check if aberrant GLDC expression is specific to NSCLC, we examined a variety of other cancers. Surprisingly GLDC is also aberrantly upregulated in subsets of primary tumors from other cancers, especially ovarian and germ cell tumors (FIG. 14A; Table 5). Further analysis of 606 human cancer cell-lines showed that 158 (26.1%) cancer cell lines overexpress GLDC, including lines from ovarian, germ cell, cervical, lung, lymphoma, prostate, bladder, and colon cancer (FIG. 14B; Table 6).

TABLE 5

Microarray datasets for GLDC analysis of patient tumor tissues and tumor cell lines, Related to FIG. 7

| GEO # used for primary tumor tissues | GEO # used for tumor cell lines |
| --- | --- |
| GSE10072 | GSE10043 |
| GSE10927 | GSE10309 |
| GSE11024 | GSE10843 |
| GSE12453 | GSE11324 |
| GSE12470 | GSE11440 |
| GSE13276 | GSE11618 |

TABLE 5-continued

Microarray datasets for GLDC analysis of patient tumor tissues and tumor cell lines, Related to FIG. 7

| GEO # used for primary tumor tissues | GEO # used for tumor cell lines |
|---|---|
| GSE14001 | GSE11670 |
| GSE14407 | GSE11812 |
| GSE14999 | GSE12056 |
| GSE15852 | GSE12445 |
| GSE17072 | GSE12790 |
| GSE17351 | GSE13144 |
| GSE17558 | GSE13280 |
| GSE18155 | GSE14231 |
| GSE18462 | GSE14994 |
| GSE18520 | GSE15329 |
| GSE19188 | GSE16378 |
| GSE19728 | GSE1824 |
| GSE19249 | GSE1845 |
| GSE20916 | GSE21154 |
| GSE21122 | GSE21654 |
| GSE23400 | GSE22183 |
| GSE23878 | GSE3001 |
| GSE2503 | GSE3493 |
| GSE2514 | GSE4127 |
| GSE2712 | GSE4176 |
| GSE3167 | GSE4342 |
| GSE3189 | GSE4975 |
| GSE3218 | GSE5519 |
| GSE3268 | GSE5845 |
| GSE3524 | GSE6013 |
| GSE4170 | GSE6222 |
| GSE4183 | GSE6410 |
| GSE5364 | GSE7097 |
| GSE5550 | GSE7556 |
| GSE6099 | GSE7562 |
| GSE6344 | GSE7930 |
| GSE6631 | GSE8087 |
| GSE686 | GSE8562 |
| GSE6883 | GSE8565 |
| GSE6919 | GSE9118 |
| GSE7476 | GSE9633 |
| GSE7803 | GSE9712 |
| GSE9476 | GSE9713 |
| GSE9750 | GSE9714 |
| GSE9844 | GSE9750 |
| GSE9891 | |

TABLE 6

Microarray datasets for GLDC analysis of human cancer cell lines (n = 606), Related to FIG. 7

| Organ | Total number of cancer cell lines | Number of cell lines with high GLDC expression | Percentage of cell lines with high GLDC (%) |
|---|---|---|---|
| Germ cell | 8 | 5 | 62.5 |
| Liver | 7 | 4 | 57.1 |
| Cervix | 9 | 5 | 55.6 |
| Brain | 4 | 2 | 50 |
| Ovary | 27 | 13 | 48.1 |
| Kidney | 58 | 24 | 41.4 |
| Gastric | 38 | 11 | 28.9 |
| Lung | 132 | 38 | 28.8 |
| Skin | 32 | 7 | 21.9 |
| Blood | 65 | 14 | 21.5 |
| Head & Neck | 5 | 1 | 20 |
| Pancreas | 23 | 4 | 17.4 |
| Prostate | 21 | 3 | 14.3 |
| Colon | 76 | 6 | 7.9 |
| Bladder | 40 | 3 | 7.5 |
| Total | 606 | 158 | 26.1 |

To test if GLDC is also required for growth by one of these GLDC-overexpressing cell-lines, we knocked down GLDC in CACO2 cells. Indeed we found that GLDC knockdown reduced their proliferation and tumorigenic potential upon transplantation, suggesting that GLDC may act as an oncogene in other cancer cells as well (FIGS. 14C-E). To examine the possibility that GLDC is a housekeeping gene for cell proliferation, we also knocked down GLDC in normal HLFs (FIG. 21A). We found that HLF proliferation was unaffected by retroviral knockdown of GLDC (FIG. 21B-C). Furthermore we observed that GLDC is highly expressed only in a few normal tissues, including post-mitotic liver cells, kidney cells, placenta cells, and olfactory bulb neurons (FIG. 21D). Altogether our observations in both experimental and clinical settings suggest that human GLDC is not a housekeeping gene required for cell proliferation, but rather an oncogenic metabolic enzyme aberrantly upregulated in NSCLC and possibly several other human cancers.

Use of GLDC as a Diagnostic Marker

FIG. 22 (A) demonstrates the Linear relationship between GLDC protein concentration and Luminescence signals in an ELISA assay. Clinical significance: Diagnosis of cancer and live-monitoring of treatment effects by analysis GLDC level in serum from lung and other type of cancer patients as depicted in FIG. 22 (B).

Tumor Suppression Cellular Assay

Using a CellTiter-Glo® Luminescent Cell Viability Assay based on the Luciferase reaction principle (FIG. 22 (C)) a clear correlation with ATP production and tumor sphere cells is observed (FIGS. 22 D and E).

This assay has the advantages that it is Fast: 10 minutes, Sensitive as it can detect <100 cells, Robust: luminescent signal is stable, Accurate: linear to cell number (0-75,000) with little Background signal <10 RLU Assay of Chemotherapeutic Drugs and Chemical Inhibitors FIG. 22 F depicts the amount of GLDC present in samples after the chemotherapeutic agents Carboplatin or the inhibitor polyketide is administered to a tumor mass of cells.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially or" and "consists essentially of" have the meaning ascribed to them in U.S. patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

```
Human GLDC DNA sequence listing:                                       SEQ ID NO 1
   1 cccgcgagcg tccatccatc tgtccggccg actgtccagc gaaaggggct ccaggccggg 61 cgcacgtcga cccggggac cgaggccagg agagggcca agagcgcggc tgacccttgc 121 gggccggggc aggggacggt ggccgcggcc atgcagtcct gtgccagggc gtgggggctg 181 cgcctgggcc gcggggtcgg gggcggccgc cgcctggctg ggggatcggg gccgtgctgg 241 gcgccgcgga gccgggacag cagcagtggc ggcggggaca gcgccgcggc tgggcctcg 301 cgcctcctgg agcgccttct gcccagacac gacgacttcg ctcggaggca catcggccct 361 ggggacaaag accagagaga gatgctgcag accttggggc tggcgagcat tgatgaattg 421 atcgagaaga cggtccctgc caacatccgt ttgaaaagac ccttgaaaat ggaagaccct 481 gtttgtgaaa atgaaatcct tgcaactctg catgccattt caagcaaaaa ccagatctgg 541 agatcgtata ttggcatggg ctattataac tgctcagtgc cacagacgat tttgcggaac 601 ttactggaga actcaggatg gatcacccag tatactccat accagcctga ggtgtctcag 661 gggaggctgg agagtttact caactaccag accatggtgt gtgacatcac aggcctggac 721 atggccaatg catccctgct ggatgagggg actgcagccg cagaggcact gcagctgtgc 781 tacagacaca acaagaggag gaaatttctc gttgatcccc gttgccaccc acagacaata 841 gctgttgtcc agactcgagc caaatatact ggagtcctca ctgagctgaa gttaccctgt 901 gaaatggact tcagtggaaa agatgtcagt ggagtgttgt tccagtaccc agacacggag 961 gggaaggtgg aagactttac ggaactcgtg gagagagctc atcagagtgg gagcctggcc 1021 tgctgtgcta ctgaccttt agctttgtgc atcttgaggc cacctggaga atttggggta 1081 gacatcgccc tgggcagctc ccagagattt ggagtgccac tgggctatgg gggaccccat 1141 gcagcatttt ttgctgtccg agaaagcttg gtgagaatga tgcctggaag aatggtgggg 1201 gtaacaagag atgccactgg gaaagaagtg tatcgtcttg ctcttcaaac cagggagcaa 1261 cacattcgga gagacaaggc taccagcaac atctgtacag ctcaggccct cttggcgaat 1321 atggctgcca tgtttcgaat ctaccatggt tcccatgggc tggagcatat tgctaggagg 1381 gtacataatg ccactttgat tttgtcagaa ggtctcaagg gagcagggca tcaactccag 1441 catgacctgt tctttgatac cttgaagatt cattgtggct gctcagtgaa ggaggtcttg 1501 ggcagggcgg ctcagcggca gatcaatttt cggctttttg aggatggcac acttggtatt 1561 tctcttgatg aaacagtcaa tgaaaaagat ctggacgatt tgttgtggat ctttggttgt 1621 gagtcatctg cagaactggt tgctgaaagc atgggagagg agtgcagagg tattccaggg 1681 tctgtgttca agaggaccag cccgttcctc acccatcaag tgttcaacag ctaccactct 1741 gaaacaaaca ttgtccggta catgaagaaa ctggaaaata agacatttc ccttgttcac 1801 agcatgattc cactgggatc ctgcaccatg aaactgaaca gttcgtctga actcgcacct
```

-continued

```
1861 atcacatgga aagaatttgc aaacatccac ccctttgtgc ctctggatca agctcaagga 1921 tatcagcagc ttttccgaga gcttgagaag gatttgtgtg aactcacagg ttatgaccag 1981 gtctgtttcc agccaaacag cggagcccag ggagaatatg ctggactggc cactatccga 2041 gcctacttaa accagaaagg agaggggcac agaacggttt gcctcattcc gaaatcagca 2101 catgggacca acccagcaag tgcccacatg gcaggcatga agattcagcc tgtggaggtg 2161 gataaatatg ggaatatcga tgcagttcac ctcaaggcca tggtggataa gcacaaggag 2221 aacctagcag ctatcatgat tacataccca tccaccaatg gggtgtttga agagaacatc 2281 agtgacgtgt gtgacctcat ccatcaacat ggaggacagg tctacctaga cggggcaaat 2341 atgaatgctc aggtgggaat ctgtcgccct ggagacttcg ggtctgatgt ctcgcaccta 2401 aatcttcaca agaccttctg cattcccac ggaggaggtg gtcctggcat ggggcccatc 2461 ggagtgaaga aacatctcgc cccgttttg cccaatcatc ccgtcatttc actaaagcgg 2521 aatgaggatg cctgtcctgt gggaaccgtc agtgcggccc catggggctc cagttccatc 2581 ttgcccattt cctgggctta tatcaagatg atggaggca agggtcttaa acaagccacg 2641 gaaactgcga tattaaatgc caactacatg gccaagcgat tagaaacaca ctacagaatt 2701 cttttcaggg gtgcaagagg ttatgtgggt catgaattta ttttggacac gagacccttc 2761 aaaaagtctg caaatattga ggctgtggat gtggccaaga ctccagga ttatggattt 2821 cacgcccta ccatgtcctg gcctgtggca gggaccctca tggtggagcc cactgagtcg 2881 gaggacaagg cagagctgga cagattctgt gatgccatga tcagcattcg gcaggaaatt 2941 gctgacattg aggagggccg catcgacccc agggtcaatc cgctgaagat gtctccacac 3001 tccctgacct gcgttacatc ttcccactgg gaccggcctt attccagaga ggtggcagca 3061 ttcccactcc ccttcatgaa accagagaac aaattctggc caacgattgc ccggattgat 3121 gacatatatg gagatcagca cctggtttgt acctgcccac ccatggaagt ttatgagtct 3181 ccatttttctg aacaaagag ggcgtcttct tagtcctctc tccctaagtt taaaggactg 3241 atttgatgcc tctccccaga gcatttgata agcaagaaag atttcatctc cacccagc 3301 ctcaagtagg agttttatat actgtgtata tctctgtaat ctctgtcaag gtaaatgtaa 3361 atacagtagc tggagggagt cgaagctgat ggttggaaga cggatttgct ttggtattct 3421 gcttccacat gtgccagttg cctggattgg gagccatttt gtgttttgcg tagaaagttt 3481 taggaacttt aactttaat gtggcaagtt tgcagatgtc atagaggcta tcctggagac 3541 ttaatagaca ttttttttgtt ccaaaagagt ccatgtggac tgtgccatct gtgggaaatc 3601 ccagggcaaa tgtttacatt ttgtataccc tgaagaactc ttttttcctct aatatgccta 3661 atctgtaatc acatttctga gtgttttcct cttttctgt gtgaggtttt ttttttttt 3721 aatctgcatt tattagtatt ctaataaaag cattttgatc ggaaaaaaaa aaaaaaaaa 3781 aaa
```

Human GLDP protein sequence.:                                  SEQ ID NO 2

```
              10          20          30          40          50          60
     MQSCARAWGL  RLGRGVGGGR  RLAGGSGPCW  APRSRDSSSG  GGDSAAAGAS  RLLERLLPRH 70          80          90         100         110         120
     DDFARRHIGP  GDKDQREMLQ  TLGLASIDEL  IEKTVPANIR  LKRPLKMEDP  VCENEILATL 130         140         150         160         170         180
     HAISSKNQIW  RSYIGMGYYN  CSVPQTILRN  LLENSGWITQ  YTPYQPEVSQ  GRLESLLNYQ 190         200         210         220         230         240
     TMVCDITGLD  MANASLLDEG  TAAAEALQLC  YRHNKRRKFL  VDPRCHPQTI  AVVQTRAKYT
```

-continued

```
        250        260        270        280        290        300
GVLTELKLPC EMDFSGKDVS GVLFQYPDTE GKVEDFTELV ERAHQSGSLA CCATDLLALC 310        320        330        340        350        360
ILRPPGEFGV DIALGSSQRF GVPLGYGGPH AAFFAVRESL VRMMPGRMVG VTRDATGKEV 370        380        390        400        410        420
YRLALQTREQ HIRRDKATSN ICTAQALLAN MAAMFAIYHG SHGLEHIARR VHNATLILSE 430        440        450        460        470        480
GLKRAGHQLQ HDLFFDTLKI QCGCSVKEVL GRAAQRQINF RLFEDGTLGI SLDETVNEKD 490        500        510        520        530        540
LDDLLWIFGC ESSAELVAES MGEECRGIPG SVFKRTSPFL THQVFNSYHS ETNIVRYMKK 550        560        570        580        590        600
LENKDISLVH SMIPLGSCTM KLNSSSELAP ITWKEFANIH PFVPLDQAQG YQQLFRELEK 610        620        630        640        650        660
DLCELTGYDQ VCFQPNSGAQ GEYAGLATIR AYLNQKGEGH RTVCLIPKSA HGTNPASAHM 670        680        690        700        710        720
AGMKIQPVEV DKYGNIDAVH LKAMVDKHKE NLAAIMITYP STNGVFEENI SDVCDLIHQH 730        740        750        760        770        780
GGQVYLDGAN MNAQVGICRP GDFGSDVSHL NLHKTFCIPH GGGGPMGPI  GVKKHLAPFL 790        800        810        820        830        840
PNHPVISLKR NEDACPVGTV SAAPWGSSSI LPISWAYIKM MGGKGLKQAT ETAILNANYM 850        860        870        880        890        900
AKRLETHYRI LFRGARGYVG HEFILDTRPF KKSANIEAVD VAKRLQDYGF HAPTMSWPVA 910        920        930        940        950        960
GTLMVEPTES EDKAELDRFC DAMISIRQEI ADIEEGRIDP RVNPLKMSPH SLTCVTSSHW 970        980        990       1000       1010       1020
DRPYSREVAA FPLPFVKPEN KFWPTIARID DIYGDQHLVC TCPPMEVYES PFSEQKRASS
```

Glycine dehydrogenase, MISSION shRNA Lentiviral Transduction
Particles (Sigma, NM_000170/TRCN0000036600): SEQ ID NO: 70
CCGGCCTGCCAACATCCGTTTGAAACTCGAGTTTCAAACGGATGTTGGCAGG
TTTTTG

---

The invention claimed is:

1. A method for inhibiting cell proliferation of human lung cancer cells or human colon cancer cells in vivo, comprising contacting the human lung cancer cells or the human colon cancer cells in vivo with an inhibitor of glycine dehydrogenase (GLDC) expression or activity, wherein the GLDC has a nucleic acid sequence set forth in SEQ ID NO: 1 or an amino acid sequence set forth in SEQ ID NO: 2, wherein the inhibitor is in an amount effective for inhibiting cell proliferation of the human lung cancer cells or the human colon cancer cells, and wherein the GLDC inhibitor comprises a small interfering RNA that comprises a nucleotide sequence selected from the group consisting of SEQ ID NO: 3, SEQ ID NO: 6, SEQ ID NO: 7, SEQ ID NO: 8 and SEQ ID NO: 9.

2. The method of claim 1 further comprising contacting the human lung cancer cells with methotrexate.

3. A method for inhibiting cell proliferation of human lung cancer cells in vivo, comprising contacting the human lung cancer cells in vivo with (a) an inhibitor of glycine dehydrogenase (GLDC) expression or activity and (b) methotrexate, wherein the GLDC has a nucleic acid sequence set forth in SEQ ID NO: 1 or an amino acid sequence set forth in SEQ ID NO: 2, and
wherein the inhibitor and methotrexate are in an amount effective for inhibiting cell proliferation of the human cancer cells.

* * * * *

SEQUENCE LISTING

<160> NUMBER OF SEQ ID NOS: 78

<210> SEQ ID NO 1
<211> LENGTH: 3783
<212> TYPE: DNA
<213> ORGANISM: Homo sapiens

<400> SEQUENCE: 1

```
cccgcgagcg tccatccatc tgtccggccg actgtccagc gaaagggct  ccaggccggg    60 cgcacgtcga cccgggggac cgaggccagg agagggccca agagcgcggc tgacccttgc   120
gggccggggc aggggacggt ggccgcggcc atgcagtcct gtgccagggc gtggggctg    180 cgcctgggcc gcgggtcgg  gggcggccgc cgcctggctg ggggatcggg gccgtgctgg   240
gcgccgcgga gccgggacag cagcagtggc ggcggggaca cgccgcggc  tggggcctcg   300 cgcctcctgg agcgccttct gcccagacac gacgacttcg ctcggaggca catcggccct   360
ggggacaaag accagagaga gatgctgcag accttgggc  tggcgagcat tgatgaattg   420
atcgagaaga cggtccctgc caacatccgt ttgaaaagac ccttgaaaat ggaagaccct   480
gtttgtgaaa atgaaatcct tgcaactctg catgccattt caagcaaaaa ccagatctgg   540
agatcgtata ttggcatggg ctattataac tgctcagtgc cacagacgat tttgcggaac   600
```

```
ttactggaga actcaggatg gatcacccag tatactccat accagcctga ggtgtctcag    660
gggaggctgg agagtttact caactaccag accatggtgt gtgacatcac aggcctggac    720
atggccaatg catccctgct ggatgagggg actgcagccg cagaggcact gcagctgtgc    780
tacagacaca acaagaggag gaaatttctc gttgatcccc gttgccaccc acagacaata    840
gctgttgtcc agactcgagc caaatatact ggagtcctca ctgagctgaa gttaccctgt    900
gaaatggact tcagtggaaa agatgtcagt ggagtgttgt tccagtaccc agacacggag    960
gggaaggtgg aagactttac ggaactcgtg agagagctc atcagagtgg gagcctggcc    1020
tgctgtgcta ctgacctttt agctttgtgc atcttgaggc cacctggaga atttggggta    1080
gacatcgccc tgggcagctc ccagagattt ggagtgccac tgggctatgg ggacccccat    1140
gcagcatttt tgctgtccg agaaagcttg gtgagaatga tgcctggaag aatggtgggg    1200
gtaacaagag atgccactgg gaaagaagtg tatcgtcttg ctcttcaaac cagggagcaa    1260
cacattcgga gagacaaggc taccagcaac atctgtacag ctcaggccct cttggcgaat    1320
atggctgcca tgtttcgaat ctaccatggt tcccatgggc tggagcatat tgctaggagg    1380
gtacataatg ccactttgat tttgtcagaa ggtctcaagc gagcagggca tcaactccag    1440
catgacctgt tctttgatac cttgaagatt cattgtggct gctcagtgaa ggaggtcttg    1500
ggcagggcgg ctcagcggca gatcaatttt cggcttttg aggatggcac acttggtatt    1560
tctcttgatg aaacagtcaa tgaaaaagat ctggacgatt tgttgtggat cttggttgt    1620
gagtcatctg cagaactggt tgctgaaagc atgggagagg agtgcagagg tattccaggg    1680
tctgtgttca agaggaccag cccgttcctc acccatcaag tgttcaacag ctaccactct    1740
gaaacaaaca ttgtccggta catgaagaaa ctggaaaata agacatttc ccttgttcac    1800
agcatgattc cactgggatc ctgcaccatg aaactgaaca gttcgtctga actcgcacct    1860
atcacatgga aagaatttgc aaacatccac ccctttgtgc ctctggatca agctcaagga    1920
tatcagcagc ttttccgaga gcttgagaag gatttgtgtg aactcacagg ttatgaccag    1980
gtctgtttcc agccaaacag cggagcccag ggagaatatg ctggactggc cactatccga    2040
gcctacttaa accagaaagg agaggggcac agaacggttt gcctcattcc gaaatcagca    2100
catgggacca acccagcaag tgcccacatg gcaggcatga agattcagcc tgtggaggtg    2160
gataaatatg ggaatatcga tgcagttcac ctcaaggcca tggtggataa gcacaaggag    2220
aacctagcag ctatcatgat tacatacccca tccaccaatg gggtgtttga agagaacatc    2280
agtgacgtgt gtgacctcat ccatcaacat ggaggacagg tctacctaga cggggcaaat    2340
atgaatgctc aggtgggaat ctgtcgccct ggagacttcg ggtctgatgt ctcgcaccta    2400
aatcttcaca agaccttctg cattccccac ggaggaggtg gtcctggcat ggggcccatc    2460
ggagtgaaga acatctcgc cccgttttg cccaatcatc ccgtcatttc actaaagcgg    2520
aatgaggatg cctgtcctgt gggaaccgtc agtgcggccc catggggctc cagttccatc    2580
ttgcccattt cctgggctta tatcaagatg atgggaggca agggtcttaa caagccacg    2640
gaaactgcga tattaaatgc caactacatg gccaagcgat tagaaacaca ctacagaatt    2700
cttttcaggg gtgtcaagag gttatgtggg catgaattta ttttggacac gagacccttc    2760
aaaaagtctg caaatattga ggctgtggat gtggccaaga gactccagga ttatggattt    2820
cacgccccta ccatgtcctg gcctgtggca gggaccctca tggtggagcc cactgagtcg    2880
gaggacaagc agagctgga cagattctgt gatgccatga tcagcattcg gcaggaaatt    2940
gctgacattg aggagggccg catcgacccc agggtcaatc cgctgaagat gtctccacac    3000
```

-continued

```
tccctgacct gcgttacatc ttcccactgg gaccggcctt attccagaga ggtggcagca    3060
ttcccactcc ccttcatgaa accagagaac aaattctggc caacgattgc ccggattgat    3120
gacatatatg gagatcagca cctggtttgt acctgcccac ccatggaagt ttatgagtct    3180
ccattttctg aacaaaagag ggcgtcttct tagtcctctc tccctaagtt taaaggactg    3240
atttgatgcc tctccccaga gcatttgata agcaagaaag atttcatctc ccaccccagc    3300
ctcaagtagg agttttatat actgtgtata tctctgtaat ctctgtcaag gtaaatgtaa    3360
atacagtagc tggagggagt cgaagctgat ggttggaaga cggatttgct ttggtattct    3420
gcttccacat gtgccagttg cctggattgg gagccatttt gtgttttgcg tagaaagttt    3480
taggaacttt aacttttaat gtggcaagtt tgcagatgtc atagaggcta tcctggagac    3540
ttaatagaca ttttttgtt ccaaaagagt ccatgtggac tgtgccatct gtgggaaatc    3600
ccagggcaaa tgtttacatt ttgtataccc tgaagaactc ttttcctct aatatgccta    3660 atctgtaatc acatttctga gtgttttcct cttttctgt gtgaggtttt ttttttttt    3720 aatctgcatt tattagtatt ctaataaaag catttgatc ggaaaaaaaa aaaaaaaaa    3780 aaa                                                                 3783
```

<210> SEQ ID NO 2
<211> LENGTH: 1020
<212> TYPE: PRT
<213> ORGANISM: Homo sapiens

<400> SEQUENCE: 2

```
Met Gln Ser Cys Ala Arg Ala Trp Gly Leu Arg Leu Gly Arg Gly Val
1               5                   10                  15

Gly Gly Gly Arg Arg Leu Ala Gly Gly Ser Gly Pro Cys Trp Ala Pro
            20                  25                  30

Arg Ser Arg Asp Ser Ser Gly Gly Asp Ser Ala Ala Ala Gly
        35                  40                  45

Ala Ser Arg Leu Leu Glu Arg Leu Leu Pro Arg His Asp Asp Phe Ala
    50                  55                  60

Arg Arg His Ile Gly Pro Gly Asp Lys Asp Gln Arg Glu Met Leu Gln
65                  70                  75                  80

Thr Leu Gly Leu Ala Ser Ile Asp Glu Leu Ile Glu Lys Thr Val Pro
                85                  90                  95

Ala Asn Ile Arg Leu Lys Arg Pro Leu Lys Met Glu Asp Pro Val Cys
            100                 105                 110

Glu Asn Glu Ile Leu Ala Thr Leu His Ala Ile Ser Ser Lys Asn Gln
        115                 120                 125

Ile Trp Arg Ser Tyr Ile Gly Met Gly Tyr Tyr Asn Cys Ser Val Pro
    130                 135                 140

Gln Thr Ile Leu Arg Asn Leu Leu Glu Asn Ser Gly Trp Ile Thr Gln
145                 150                 155                 160

Tyr Thr Pro Tyr Gln Pro Glu Val Ser Gln Gly Arg Leu Glu Ser Leu
                165                 170                 175

Leu Asn Tyr Gln Thr Met Val Cys Asp Ile Thr Gly Leu Asp Met Ala
            180                 185                 190

Asn Ala Ser Leu Leu Asp Glu Gly Thr Ala Ala Ala Glu Ala Leu Gln
        195                 200                 205

Leu Cys Tyr Arg His Asn Lys Arg Arg Lys Phe Leu Val Asp Pro Arg
    210                 215                 220
```

```
Cys His Pro Gln Thr Ile Ala Val Val Gln Thr Arg Ala Lys Tyr Thr
225                 230                 235                 240

Gly Val Leu Thr Glu Leu Lys Leu Pro Cys Glu Met Asp Phe Ser Gly
                245                 250                 255

Lys Asp Val Ser Gly Val Leu Phe Gln Tyr Pro Asp Thr Glu Gly Lys
            260                 265                 270

Val Glu Asp Phe Thr Glu Leu Val Glu Arg Ala His Gln Ser Gly Ser
        275                 280                 285

Leu Ala Cys Cys Ala Thr Asp Leu Leu Ala Leu Cys Ile Leu Arg Pro
290                 295                 300

Pro Gly Glu Phe Gly Val Asp Ile Ala Leu Gly Ser Ser Gln Arg Phe
305                 310                 315                 320

Gly Val Pro Leu Gly Tyr Gly Pro His Ala Ala Phe Phe Ala Val
                325                 330                 335

Arg Glu Ser Leu Val Arg Met Met Pro Gly Arg Met Val Gly Val Thr
                340                 345                 350

Arg Asp Ala Thr Gly Lys Glu Val Tyr Arg Leu Ala Leu Gln Thr Arg
                355                 360                 365

Glu Gln His Ile Arg Arg Asp Lys Ala Thr Ser Asn Ile Cys Thr Ala
370                 375                 380

Gln Ala Leu Leu Ala Asn Met Ala Ala Met Phe Ala Ile Tyr His Gly
385                 390                 395                 400

Ser His Gly Leu Glu His Ile Ala Arg Arg Val His Asn Ala Thr Leu
                405                 410                 415

Ile Leu Ser Glu Gly Leu Lys Arg Ala Gly His Gln Leu Gln His Asp
                420                 425                 430

Leu Phe Phe Asp Thr Leu Lys Ile Gln Cys Gly Cys Ser Val Lys Glu
            435                 440                 445

Val Leu Gly Arg Ala Ala Gln Arg Gln Ile Asn Phe Arg Leu Phe Glu
450                 455                 460

Asp Gly Thr Leu Gly Ile Ser Leu Asp Glu Thr Val Asn Glu Lys Asp
465                 470                 475                 480

Leu Asp Asp Leu Leu Trp Ile Phe Gly Cys Glu Ser Ser Ala Glu Leu
                485                 490                 495

Val Ala Glu Ser Met Gly Glu Glu Cys Arg Gly Ile Pro Gly Ser Val
            500                 505                 510

Phe Lys Arg Thr Ser Pro Phe Leu Thr His Gln Val Phe Asn Ser Tyr
            515                 520                 525

His Ser Glu Thr Asn Ile Val Arg Tyr Met Lys Lys Leu Glu Asn Lys
530                 535                 540

Asp Ile Ser Leu Val His Ser Met Ile Pro Leu Gly Ser Cys Thr Met
545                 550                 555                 560

Lys Leu Asn Ser Ser Ser Glu Leu Ala Pro Ile Thr Trp Lys Glu Phe
                565                 570                 575

Ala Asn Ile His Pro Phe Val Pro Leu Asp Gln Ala Gln Gly Tyr Gln
                580                 585                 590

Gln Leu Phe Arg Glu Leu Glu Lys Asp Leu Cys Glu Leu Thr Gly Tyr
            595                 600                 605

Asp Gln Val Cys Phe Gln Pro Asn Ser Gly Ala Gln Gly Glu Tyr Ala
            610                 615                 620

Gly Leu Ala Thr Ile Arg Ala Tyr Leu Asn Gln Lys Gly Glu Gly His
625                 630                 635                 640

Arg Thr Val Cys Leu Ile Pro Lys Ser Ala His Gly Thr Asn Pro Ala
```

```
                    645                 650                 655
Ser Ala His Met Ala Gly Met Lys Ile Gln Pro Val Glu Val Asp Lys
                660                 665                 670

Tyr Gly Asn Ile Asp Ala Val His Leu Lys Ala Met Val Asp Lys His
            675                 680                 685

Lys Glu Asn Leu Ala Ala Ile Met Ile Thr Tyr Pro Ser Thr Asn Gly
        690                 695                 700

Val Phe Glu Glu Asn Ile Ser Asp Val Cys Asp Leu Ile His Gln His
705                 710                 715                 720

Gly Gly Gln Val Tyr Leu Asp Gly Ala Asn Met Asn Ala Gln Val Gly
                725                 730                 735

Ile Cys Arg Pro Gly Asp Phe Gly Ser Asp Val Ser His Leu Asn Leu
            740                 745                 750

His Lys Thr Phe Cys Ile Pro His Gly Gly Gly Pro Gly Met Gly
        755                 760                 765

Pro Ile Gly Val Lys Lys His Leu Ala Pro Phe Leu Pro Asn His Pro
    770                 775                 780

Val Ile Ser Leu Lys Arg Asn Glu Asp Ala Cys Pro Val Gly Thr Val
785                 790                 795                 800

Ser Ala Ala Pro Trp Gly Ser Ser Ile Leu Pro Ile Ser Trp Ala
                805                 810                 815

Tyr Ile Lys Met Met Gly Gly Lys Gly Leu Lys Gln Ala Thr Glu Thr
            820                 825                 830

Ala Ile Leu Asn Ala Asn Tyr Met Ala Lys Arg Leu Glu Thr His Tyr
        835                 840                 845

Arg Ile Leu Phe Arg Gly Ala Arg Gly Tyr Val Gly His Glu Phe Ile
    850                 855                 860

Leu Asp Thr Arg Pro Phe Lys Lys Ser Ala Asn Ile Glu Ala Val Asp
865                 870                 875                 880

Val Ala Lys Arg Leu Gln Asp Tyr Gly Phe His Ala Pro Thr Met Ser
                885                 890                 895

Trp Pro Val Ala Gly Thr Leu Met Val Glu Pro Thr Glu Ser Glu Asp
            900                 905                 910

Lys Ala Glu Leu Asp Arg Phe Cys Asp Ala Met Ile Ser Ile Arg Gln
        915                 920                 925

Glu Ile Ala Asp Ile Glu Glu Gly Arg Ile Asp Pro Arg Val Asn Pro
    930                 935                 940

Leu Lys Met Ser Pro His Ser Leu Thr Cys Val Thr Ser Ser His Trp
945                 950                 955                 960

Asp Arg Pro Tyr Ser Arg Glu Val Ala Ala Phe Pro Leu Pro Phe Val
                965                 970                 975

Lys Pro Glu Asn Lys Phe Trp Pro Thr Ile Ala Arg Ile Asp Asp Ile
            980                 985                 990

Tyr Gly Asp Gln His Leu Val Cys  Thr Cys Pro Pro Met  Glu Val Tyr
        995                 1000                 1005

Glu Ser  Pro Phe Ser Glu Gln  Lys Arg Ala Ser Ser
    1010                 1015                 1020

<210> SEQ ID NO 3
<211> LENGTH: 58
<212> TYPE: RNA
<213> ORGANISM: Artificial Sequence
<220> FEATURE:
<223> OTHER INFORMATION: Glycine dehydrogenase, MISSION shRNA Lentiviral
      Transduction Particles (Sigma, NM_000170 / TRCN0000036600)
```

```
<400> SEQUENCE: 3
ccggccugcc aacauccguu ugaaacucga guuucaaacg gauguuggca gguuuuug      58

<210> SEQ ID NO 4
<211> LENGTH: 3120
<212> TYPE: DNA
<213> ORGANISM: Homo sapiens

<400> SEQUENCE: 4
aattgacaaa gtcacgtgtg ctcaggggc cagaaactgg agagaggaga gaaaaaaat      60 caaaagaagg aaagcacatt agaccatgcg agctaaattt gtgatcgcac aaaatcaaga   120
tgttagattg atgcagaaga tcactccgtt ccaaagggaa agttttcatc tcacgagttt   180
ggagctgagg gcccgtgggg caacatggcc gaaggcgggg ctagcaaagg tggtggagaa   240
gagcccggga agctgccgga gccggcagag gaggaatccc aggttttgcg cggaactggc   300
cactgtaagt ggttcaatgt gcgcatggga tttggattca tctccatgat aaaccgagag   360
ggaagcccct tggatattcc agtcgatgta tttgtacacc aaagcaaact attcatggaa   420
ggatttagaa gcctaaaaga aggagaacca gtggaattca catttaaaaa atcttccaaa   480
ggccttgagt caatacgggt aacaggacct ggtgggagcc cctgtttagg aagtgaaaga   540
agacccaaag ggaagacact acagaaaaga aaccaaagg gagatagatg ctacaactgt   600
ggtggccttg atcatcatgc taaggaatgt agtctacctc ctcagccaaa gaagtgccat   660
tactgtcaga gcatcatgca catggtggca aactgcccac ataaaaatgt tgcacagcca   720
cccgcgagtt ctcagggaag acaggaagca gaatcccagc catgcacttc aactctccct   780
cgagaagtgg gaggcgggca tggctgtaca tcaccaccgt ttcctcagga ggctagggca   840
gagatctcag aacggtcagg caggtcacct caagaagctt cctccacgaa gtcatctata   900
gcaccagaag agcaaagcaa aaaggggcct tcagttcaaa aaggaaaaa gacataacag   960 gtcttcttca tatgttcttt cctttacccg gttgcaaagt ctacctcatg caagtatagg  1020
ggaacagtat ttcacaagca gtagctgacc tgggatttta actactattg gggaactgtg  1080 aatttttaa acagacaaat cactctaagc aaattacatt tgagcagggt gtcatgtttt  1140
atgttaattc agagaataag atactatgtc tgtcaatatg tgcatgtgtg agagggagag  1200
agcctgagtc tgtgtgtgta catgaggatt tttatatagg aatgtagaca catatataaa  1260
gaggctttgt ctttatatat ttgtgtatag atcaaagcac acaccctctc tcatataatt  1320
ggatatttcc aagaattgaa aacccatgtg aagcattata gatagtttta aatttaaccc  1380
actggagttt tcttgaaata ccacttcttt tatattatat aaaactaaaa acacgactgt  1440 tacctttgt gtgaaccaaa ggatacttca gatctcagag ctgccaatta tggggtacta  1500
aaggttttta agacatccag ttctcccgaa tttgggattg cctctttttc ttgaaatctc  1560
tggagtagta attttttcc cccttttttg aaggcagtac cttaacttca tatgcctctg   1620
actgccataa gctttttga ttctgggata acataactcc agaaagaca atgaatgtgt    1680 aatttgggcc gatatttcac tgttttaaat tctgtgttta attgtaaaat tagatgccta  1740
ttaagagaaa tgaaggggag gatcatctta gtggcttgtt ttcagtagta tttttaatatc 1800 agcttcttgt aaccttttcc atgttgtgag ggttgtaagg gattgtgtgg caacagcagc  1860
ttcccttggc taactcaatc ttctacccat tgcttagagc agggagccct ccttatttac  1920
tactgaagac cttagagaac tccaattgtt tggcatatat ttttggtggt ggttttatt   1980
```

| | | |
|---|---|---|
| cctcctggag agttatctaa tttgtttcta aaacaaacaa gcagcaaaga aatgaattaa | 2040 | |
| atactgggt tgagaattaa aattaagtgg atgttcacag ttgcccaata tatatgacct | 2100 | |
| gcaaatgata cgaaaaagtg cagcatttag tggcagttaa caagagtgac aagcctgggg | 2160 | |
| cagaggtacc aaacctctcc caccagagag ctagaagtat tttatacagt aactttgatc | 2220 | |
| ttatggaagt gaccttcaat gcttattctg aagtaaccta tatggtggat acaggatgaa | 2280 | |
| cattcagtgc cagggagaat cttctcaggt tggttctcgt tagagtgata aactggctag | 2340 | |
| gggccatagt attggtcctg ttaggtttcg gtcatggaaa aaaaaatat tttggggtca | 2400 | |
| tcctggctct agatgttatg ggcaaatttc tgaaacatct gcaagaaggt accagttaat | 2460 | |
| tatagtgctt aatattggga ataagattaa gcattataat tataatgtat gggcctgttg | 2520 | |
| gtgtaagctc agataattaa ataaaaatag catgactcaa atgagacata ttctgctgaa | 2580 | |
| cagtttctac ttcctctccc gcctgtcctg tcatgggaga cgtgtatagt tgctgctgtt | 2640 | |
| tcagcaaacc accataagac gaaaatgcct caggttgggt tgccagtcct ttacaactca | 2700 | |
| gcttgaattt cacaacagtg attgtgagaa tctgcgtggt atacactgaa atatcggtgt | 2760 | |
| gctgtgatgc aaaacttgcc tttgacgata ttgaatgtga tatagctgta gagaagtact | 2820 | |
| tccttgcctt atgtgaggat ttcaaactta tttaaattat gtagacaaat caaagtggca | 2880 | |
| ttgcttaatt tttagcaggc ataataagca agttaacagt aaaatgcaaa acatgataag | 2940 | |
| cgttgctcaa ttttagcag gtataataag caggttaaca gtaaaatgc aaaacatgat | 3000 | |
| agataagtca ctttgaaaat tcaaaccaaa gttccttcac cttatggaaa taggaaatta | 3060 | |
| tggacttcaa aattggacac ttcctgttta caaaagaaa ttcagagcta aaatcatggt | 3120 | |

```
<210> SEQ ID NO 5
<211> LENGTH: 250
<212> TYPE: PRT
<213> ORGANISM: Homo sapiens

<400> SEQUENCE: 5

Met Ala Glu Gly Gly Ala Ser Lys Gly Gly Gly Glu Glu Pro Gly Lys
1               5                   10                  15

Leu Pro Glu Pro Ala Glu Glu Ser Gln Val Leu Arg Gly Thr Gly
            20                  25                  30

His Cys Lys Trp Phe Asn Val Arg Met Gly Phe Gly Phe Ile Ser Met
        35                  40                  45

Ile Asn Arg Glu Gly Ser Pro Leu Asp Ile Pro Val Asp Val Phe Val
    50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg
            100                 105                 110

Arg Pro Lys Gly Lys Thr Leu Gln Lys Arg Lys Pro Lys Gly Asp Arg
        115                 120                 125

Cys Tyr Asn Cys Gly Gly Leu Asp His His Ala Lys Glu Cys Ser Leu
    130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Pro Ala Ser Ser
                165                 170                 175
```

Gln Gly Arg Gln Glu Ala Glu Ser Gln Pro Cys Thr Ser Thr Leu Pro
           180                 185                 190

Arg Glu Val Gly Gly Gly His Gly Cys Thr Ser Pro Pro Phe Pro Gln
           195                 200                 205

Glu Ala Arg Ala Glu Ile Ser Glu Arg Ser Gly Arg Ser Pro Gln Glu
           210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 6
<211> LENGTH: 29
<212> TYPE: RNA
<213> ORGANISM: Artificial Sequence
<220> FEATURE:
<223> OTHER INFORMATION: GLDC shRNA

<400> SEQUENCE: 6
uagcuguugu ccagacucga gccaaauau                                   29

<210> SEQ ID NO 7
<211> LENGTH: 29
<212> TYPE: RNA
<213> ORGANISM: Artificial Sequence
<220> FEATURE:
<223> OTHER INFORMATION: GLDC shRNA

<400> SEQUENCE: 7
ggucaauccg cugaagaugu cuccacacu                                   29

<210> SEQ ID NO 8
<211> LENGTH: 29
<212> TYPE: RNA
<213> ORGANISM: Artificial Sequence
<220> FEATURE:
<223> OTHER INFORMATION: shRNA GLDC

<400> SEQUENCE: 8
uggagaguuu acucaacuac cagaccaug                                   29

<210> SEQ ID NO 9
<211> LENGTH: 29
<212> TYPE: RNA
<213> ORGANISM: Artificial Sequence
<220> FEATURE:
<223> OTHER INFORMATION: GLDC shRNA

<400> SEQUENCE: 9
uucacuaaag cggaaugagg augccuguc                                   29

<210> SEQ ID NO 10
<211> LENGTH: 29
<212> TYPE: RNA
<213> ORGANISM: Artificial Sequence
<220> FEATURE:
<223> OTHER INFORMATION: shRNA targeted to LIN28B

<400> SEQUENCE: 10
aacggucagg caggucaccu caagaagcu                                   29

<210> SEQ ID NO 11
<211> LENGTH: 29
<212> TYPE: RNA

```
<213> ORGANISM: Artificial Sequence
<220> FEATURE:
<223> OTHER INFORMATION: shRNA targeted to LIN28B

<400> SEQUENCE: 11
gccacuguaa gugguucaau gugcgcaug                                   29

<210> SEQ ID NO 12
<211> LENGTH: 29
<212> TYPE: RNA
<213> ORGANISM: Artificial Sequence
<220> FEATURE:
<223> OTHER INFORMATION: shRNA targeted to LIN28B

<400> SEQUENCE: 12
agaagugcca uuacugucag agcaucaug                                   29

<210> SEQ ID NO 13
<211> LENGTH: 29
<212> TYPE: RNA
<213> ORGANISM: Artificial Sequence
<220> FEATURE:
<223> OTHER INFORMATION: shRNA targeted to LIN28B

<400> SEQUENCE: 13
uacaucacca ccguuccuc aggaggcua                                    29

<210> SEQ ID NO 14
<211> LENGTH: 58
<212> TYPE: DNA
<213> ORGANISM: Artificial Sequence
<220> FEATURE:
<223> OTHER INFORMATION: shRNA targeted to ALCAM

<400> SEQUENCE: 14
agcagttcat tctaccaagc tgtcacagga gcagttcatt ctaccaagct gtcacagg   58

<210> SEQ ID NO 15
<211> LENGTH: 29
<212> TYPE: DNA
<213> ORGANISM: Artificial Sequence
<220> FEATURE:
<223> OTHER INFORMATION: shRNA targeted to ALCAM

<400> SEQUENCE: 15
aaggtgttca agcaaccatc taaacctga                                   29

<210> SEQ ID NO 16
<211> LENGTH: 29
<212> TYPE: DNA
<213> ORGANISM: Artificial Sequence
<220> FEATURE:
<223> OTHER INFORMATION: shRNA targeted to ALCAM

<400> SEQUENCE: 16
ttactatcct acagagcagg tgacaatac                                   29

<210> SEQ ID NO 17
<211> LENGTH: 29
<212> TYPE: DNA
<213> ORGANISM: Artificial Sequence
<220> FEATURE:
<223> OTHER INFORMATION: shRNA targeted to ALCAM

<400> SEQUENCE: 17
gaagcatgaa cgtggattgt atttaagac                                   29
```

-continued

<210> SEQ ID NO 18
<211> LENGTH: 29
<212> TYPE: DNA
<213> ORGANISM: Artificial Sequence
<220> FEATURE:
<223> OTHER INFORMATION: scrambled control shRNA:

<400> SEQUENCE: 18
gcactaccag agctaactca gatagtact                                29

<210> SEQ ID NO 19
<211> LENGTH: 59
<212> TYPE: DNA
<213> ORGANISM: Artificial Sequence
<220> FEATURE:
<223> OTHER INFORMATION: LIN28B SHCLNV: siRNA

<400> SEQUENCE: 19
ccgggccttg agtcaatacg ggtaactcga gttacccgta ttgactcaag gcttttttg     59

<210> SEQ ID NO 20
<211> LENGTH: 57
<212> TYPE: DNA
<213> ORGANISM: Artificial Sequence
<220> FEATURE:
<223> OTHER INFORMATION: control SHCLNV scrambled siRNA

<400> SEQUENCE: 20
ccggcaacaa gatgaagagc accaactcga gttggtgctc ttcatcttgt tgttttt       57

<210> SEQ ID NO 21
<211> LENGTH: 19
<212> TYPE: DNA
<213> ORGANISM: Artificial Sequence
<220> FEATURE:
<223> OTHER INFORMATION: Primer GLCD front 1

<400> SEQUENCE: 21
ccagacacga cgacttcgc                                           19

<210> SEQ ID NO 22
<211> LENGTH: 21
<212> TYPE: DNA
<213> ORGANISM: Artificial Sequence
<220> FEATURE:
<223> OTHER INFORMATION: Primer GLDC rear 1

<400> SEQUENCE: 22
caattcatca atgctcgcca g                                        21

<210> SEQ ID NO 23
<211> LENGTH: 21
<212> TYPE: DNA
<213> ORGANISM: Artificial Sequence
<220> FEATURE:
<223> OTHER INFORMATION: Primer GLDC front 2

<400> SEQUENCE: 23
atttctcgtt gatccccgtt g                                        21

<210> SEQ ID NO 24
<211> LENGTH: 21
<212> TYPE: DNA
<213> ORGANISM: Artificial Sequence
<220> FEATURE:

<223> OTHER INFORMATION: Primer GLDC rear 2

<400> SEQUENCE: 24
cacagggtaa cttcagctca g                                    21

<210> SEQ ID NO 25
<211> LENGTH: 22
<212> TYPE: DNA
<213> ORGANISM: Artificial Sequence
<220> FEATURE:
<223> OTHER INFORMATION: Primer GLDC front 3

<400> SEQUENCE: 25
cagggtcaat ccgctgaaga tg                                   22

<210> SEQ ID NO 26
<211> LENGTH: 23
<212> TYPE: DNA
<213> ORGANISM: Artificial Sequence
<220> FEATURE:
<223> OTHER INFORMATION: Primer GLDC rear 3

<400> SEQUENCE: 26
tgctgccacc tctctggaat aag                                  23

<210> SEQ ID NO 27
<211> LENGTH: 22
<212> TYPE: DNA
<213> ORGANISM: Artificial Sequence
<220> FEATURE:
<223> OTHER INFORMATION: Primer GLDC front 4

<400> SEQUENCE: 27
aaccagggag caacacattc gg                                   22

<210> SEQ ID NO 28
<211> LENGTH: 22
<212> TYPE: DNA
<213> ORGANISM: Artificial Sequence
<220> FEATURE:
<223> OTHER INFORMATION: Primer GLDC rear 4

<400> SEQUENCE: 28
atattcgcca agagggcctg ag                                   22

<210> SEQ ID NO 29
<211> LENGTH: 20
<212> TYPE: DNA
<213> ORGANISM: Artificial Sequence
<220> FEATURE:
<223> OTHER INFORMATION: Primer PSPH front 1

<400> SEQUENCE: 29
gaggacgcgg tgtcagaaat                                      20

<210> SEQ ID NO 30
<211> LENGTH: 22
<212> TYPE: DNA
<213> ORGANISM: Artificial Sequence
<220> FEATURE:
<223> OTHER INFORMATION: Primer PSPH rear 1

<400> SEQUENCE: 30
ggttgctctg ctatgagtct ct                                   22

```
<210> SEQ ID NO 31
<211> LENGTH: 22
<212> TYPE: DNA
<213> ORGANISM: Artificial Sequence
<220> FEATURE:
<223> OTHER INFORMATION: Primer PSPH front 2

<400> SEQUENCE: 31
gcataaggga gctggtaagt cg                                              22

<210> SEQ ID NO 32
<211> LENGTH: 23
<212> TYPE: DNA
<213> ORGANISM: Artificial Sequence
<220> FEATURE:
<223> OTHER INFORMATION: Primer PSPH rear 2

<400> SEQUENCE: 32
acctgcatat tcaccgttaa agt                                             23

<210> SEQ ID NO 33
<211> LENGTH: 24
<212> TYPE: DNA
<213> ORGANISM: Artificial Sequence
<220> FEATURE:
<223> OTHER INFORMATION: Primer PSPH front 3

<400> SEQUENCE: 33
tcatgattgg agatggtgcc acag                                            24

<210> SEQ ID NO 34
<211> LENGTH: 24
<212> TYPE: DNA
<213> ORGANISM: Artificial Sequence
<220> FEATURE:
<223> OTHER INFORMATION: Primer PSPH rear 3

<400> SEQUENCE: 34
caatgaaagc atcagcagga ggac                                            24

<210> SEQ ID NO 35
<211> LENGTH: 22
<212> TYPE: DNA
<213> ORGANISM: Artificial Sequence
<220> FEATURE:
<223> OTHER INFORMATION: Primer PSPH front 4

<400> SEQUENCE: 35
acggtgaata tgcaggtttt ga                                              22

<210> SEQ ID NO 36
<211> LENGTH: 23
<212> TYPE: DNA
<213> ORGANISM: Artificial Sequence
<220> FEATURE:
<223> OTHER INFORMATION: Primer PSPH rear 4

<400> SEQUENCE: 36
gttatccttg acttgttgcc tga                                             23

<210> SEQ ID NO 37
<211> LENGTH: 21
<212> TYPE: DNA
<213> ORGANISM: Artificial Sequence
<220> FEATURE:
<223> OTHER INFORMATION: Primer PSAT1 front 1
```

```
<400> SEQUENCE: 37
tgccgcactc agtgttgtta g                                              21

<210> SEQ ID NO 38
<211> LENGTH: 21
<212> TYPE: DNA
<213> ORGANISM: Artificial Sequence
<220> FEATURE:
<223> OTHER INFORMATION: Primer PSAT1 rear 1

<400> SEQUENCE: 38
gcaattcccg cacaagattc t                                              21

<210> SEQ ID NO 39
<211> LENGTH: 23
<212> TYPE: DNA
<213> ORGANISM: Artificial Sequence
<220> FEATURE:
<223> OTHER INFORMATION: Primer PSAT1 front 2

<400> SEQUENCE: 39
tctacgtcat gggcttggtt ctg                                            23

<210> SEQ ID NO 40
<211> LENGTH: 24
<212> TYPE: DNA
<213> ORGANISM: Artificial Sequence
<220> FEATURE:
<223> OTHER INFORMATION: Primer PSAT1 rear 2

<400> SEQUENCE: 40
gctccactgg acaaacgtag aatc                                           24

<210> SEQ ID NO 41
<211> LENGTH: 24
<212> TYPE: DNA
<213> ORGANISM: Artificial Sequence
<220> FEATURE:
<223> OTHER INFORMATION: Primer PSAT1 front 3

<400> SEQUENCE: 41
cagtggatgt ttccaagttt ggtg                                           24

<210> SEQ ID NO 42
<211> LENGTH: 22
<212> TYPE: DNA
<213> ORGANISM: Artificial Sequence
<220> FEATURE:
<223> OTHER INFORMATION: Primer PSAT1 rear 3

<400> SEQUENCE: 42
cctgcacctt gtattccagg ac                                             22

<210> SEQ ID NO 43
<211> LENGTH: 21
<212> TYPE: DNA
<213> ORGANISM: Artificial Sequence
<220> FEATURE:
<223> OTHER INFORMATION: Primer PSAT1 front 4

<400> SEQUENCE: 43
agcaggaagg tgtgctgact a                                              21

<210> SEQ ID NO 44
<211> LENGTH: 19
```

```
<212> TYPE: DNA
<213> ORGANISM: Artificial Sequence
<220> FEATURE:
<223> OTHER INFORMATION: Primer PSAT1 rear 4

<400> SEQUENCE: 44
cggccttagc tgaccaagc                                                  19

<210> SEQ ID NO 45
<211> LENGTH: 23
<212> TYPE: DNA
<213> ORGANISM: Artificial Sequence
<220> FEATURE:
<223> OTHER INFORMATION: Primer SHMT1 front 1

<400> SEQUENCE: 45
aaatctctgc cacgtccatc ttc                                             23

<210> SEQ ID NO 46
<211> LENGTH: 23
<212> TYPE: DNA
<213> ORGANISM: Artificial Sequence
<220> FEATURE:
<223> OTHER INFORMATION: Primer SHMT1 rear 1

<400> SEQUENCE: 46
agccagtatc tgggttcacc ttg                                             23

<210> SEQ ID NO 47
<211> LENGTH: 22
<212> TYPE: DNA
<213> ORGANISM: Artificial Sequence
<220> FEATURE:
<223> OTHER INFORMATION: Primer SHMT1 front 2

<400> SEQUENCE: 47
cgaagctgat catcgcagga ac                                              22

<210> SEQ ID NO 48
<211> LENGTH: 24
<212> TYPE: DNA
<213> ORGANISM: Artificial Sequence
<220> FEATURE:
<223> OTHER INFORMATION: Primer SHMT1 rear 2

<400> SEQUENCE: 48
tctcatctgc aatcttccgt agcc                                            24

<210> SEQ ID NO 49
<211> LENGTH: 20
<212> TYPE: DNA
<213> ORGANISM: Artificial Sequence
<220> FEATURE:
<223> OTHER INFORMATION: Primer SHMT1 front 3

<400> SEQUENCE: 49
ctggcacaac ccctcaaaga                                                 20

<210> SEQ ID NO 50
<211> LENGTH: 21
<212> TYPE: DNA
<213> ORGANISM: Artificial Sequence
<220> FEATURE:
<223> OTHER INFORMATION: Primer SHMT1 rear 3

<400> SEQUENCE: 50
```
ctctgccggt tactctcctt c          21

<210> SEQ ID NO 51
<211> LENGTH: 19
<212> TYPE: DNA
<213> ORGANISM: Artificial Sequence
<220> FEATURE:
<223> OTHER INFORMATION: Primer SHMT1 front 4

<400> SEQUENCE: 51
cagccgagca gttttggag          19

<210> SEQ ID NO 52
<211> LENGTH: 21
<212> TYPE: DNA
<213> ORGANISM: Artificial Sequence
<220> FEATURE:
<223> OTHER INFORMATION: Primer SHMT1 rear 4

<400> SEQUENCE: 52
gtcccgccat agtatctctg g          21

<210> SEQ ID NO 53
<211> LENGTH: 19
<212> TYPE: DNA
<213> ORGANISM: Artificial Sequence
<220> FEATURE:
<223> OTHER INFORMATION: Primer SHMT2 front 1

<400> SEQUENCE: 53
cttctgcaac ctcacgacc          19

<210> SEQ ID NO 54
<211> LENGTH: 23
<212> TYPE: DNA
<213> ORGANISM: Artificial Sequence
<220> FEATURE:
<223> OTHER INFORMATION: Primer SHMT2 rear 1

<400> SEQUENCE: 54
tgagcttata gggcatagac tcg          23

<210> SEQ ID NO 55
<211> LENGTH: 24
<212> TYPE: DNA
<213> ORGANISM: Artificial Sequence
<220> FEATURE:
<223> OTHER INFORMATION: Primer SHMT2 front 2

<400> SEQUENCE: 55
cttagaggtg aagagcaaga ctgc          24

<210> SEQ ID NO 56
<211> LENGTH: 24
<212> TYPE: DNA
<213> ORGANISM: Artificial Sequence
<220> FEATURE:
<223> OTHER INFORMATION: Primer SHMT2 rear 2

<400> SEQUENCE: 56
agacgctgac ttgtttctga gtcc          24

<210> SEQ ID NO 57
<211> LENGTH: 22
<212> TYPE: DNA
<213> ORGANISM: Artificial Sequence

```
<220> FEATURE:
<223> OTHER INFORMATION: primer SHMT2 front 3

<400> SEQUENCE: 57
actacaacca gctggcactg ac                                              22

<210> SEQ ID NO 58
<211> LENGTH: 24
<212> TYPE: DNA
<213> ORGANISM: Artificial Sequence
<220> FEATURE:
<223> OTHER INFORMATION: Primer SHMT2 rear 3

<400> SEQUENCE: 58
tgctttgact tcatcacaca cctc                                            24

<210> SEQ ID NO 59
<211> LENGTH: 19
<212> TYPE: DNA
<213> ORGANISM: Artificial Sequence
<220> FEATURE:
<223> OTHER INFORMATION: Primer SHMT2 front 4

<400> SEQUENCE: 59
gactacgccc gcatgagag                                                  19

<210> SEQ ID NO 60
<211> LENGTH: 21
<212> TYPE: DNA
<213> ORGANISM: Artificial Sequence
<220> FEATURE:
<223> OTHER INFORMATION: Primer SHMT2 rear 4

<400> SEQUENCE: 60
agcaggtgtg ctttgacttc a                                               21

<210> SEQ ID NO 61
<211> LENGTH: 19
<212> TYPE: DNA
<213> ORGANISM: Artificial Sequence
<220> FEATURE:
<223> OTHER INFORMATION: Primer GCAT front 1

<400> SEQUENCE: 61
ggccgaccta gaagccaag                                                  19

<210> SEQ ID NO 62
<211> LENGTH: 19
<212> TYPE: DNA
<213> ORGANISM: Artificial Sequence
<220> FEATURE:
<223> OTHER INFORMATION: Primer GCAT rear 1

<400> SEQUENCE: 62
gtgcgatgtc gccatccat                                                  19

<210> SEQ ID NO 63
<211> LENGTH: 24
<212> TYPE: DNA
<213> ORGANISM: Artificial Sequence
<220> FEATURE:
<223> OTHER INFORMATION: Primer GCAT front 2

<400> SEQUENCE: 63
cgctttatct gtggaaccca gagc                                            24
```

-continued

<210> SEQ ID NO 64
<211> LENGTH: 22
<212> TYPE: DNA
<213> ORGANISM: Artificial Sequence
<220> FEATURE:
<223> OTHER INFORMATION: Primer GCAT rear 2

<400> SEQUENCE: 64
aacagctggg atagaggatg gc                                              22

<210> SEQ ID NO 65
<211> LENGTH: 22
<212> TYPE: DNA
<213> ORGANISM: Artificial Sequence
<220> FEATURE:
<223> OTHER INFORMATION: Primer GCAT front 3

<400> SEQUENCE: 65
aaggccctag atctgctgat gg                                              22

<210> SEQ ID NO 66
<211> LENGTH: 24
<212> TYPE: DNA
<213> ORGANISM: Artificial Sequence
<220> FEATURE:
<223> OTHER INFORMATION: Primer GCAT rear 3

<400> SEQUENCE: 66
gcttccatct tactacggaa cctc                                            24

<210> SEQ ID NO 67
<211> LENGTH: 21
<212> TYPE: DNA
<213> ORGANISM: Artificial Sequence
<220> FEATURE:
<223> OTHER INFORMATION: Primer GCAT front 4

<400> SEQUENCE: 67
cctcagctct gtccgcttta t                                               21

<210> SEQ ID NO 68
<211> LENGTH: 20
<212> TYPE: DNA
<213> ORGANISM: Artificial Sequence
<220> FEATURE:
<223> OTHER INFORMATION: Primer GCAT rear 4

<400> SEQUENCE: 68
ggatgccgtc gatgatggag                                                 20

<210> SEQ ID NO 69
<211> LENGTH: 912
<212> TYPE: PRT
<213> ORGANISM: Thermus thermophilus

<400> SEQUENCE: 69

Met Asp Tyr Thr Pro His Thr Glu Glu Glu Ile Arg Glu Met Leu Arg
1               5                   10                  15

Arg Val Gly Ala Ala Ser Leu Glu Asp Leu Phe Ala His Leu Pro Lys
            20                  25                  30

Glu Ile Leu Ser Pro Pro Ile Asp Leu Pro Glu Pro Leu Pro Glu Trp
        35                  40                  45

Lys Val Leu Glu Glu Leu Arg Arg Leu Ala Ala Gln Asn Leu Pro Ala
    50                  55                  60

```
His Lys Ala Phe Leu Gly Gly Val Arg Ser His His Val Pro Pro
 65                  70                  75                  80

Val Val Gln Ala Leu Ala Ala Arg Gly Glu Phe Leu Thr Ala Tyr Thr
                 85                  90                  95

Pro Tyr Gln Pro Glu Val Ser Gln Gly Val Leu Gln Ala Thr Phe Glu
                100                 105                 110

Tyr Gln Thr Met Ile Ala Glu Leu Ala Gly Leu Glu Ile Ala Asn Ala
                115                 120                 125

Ser Met Tyr Asp Gly Ala Thr Ala Leu Ala Glu Gly Val Leu Leu Ala
            130                 135                 140

Leu Arg Glu Thr Gly Arg Met Gly Val Leu Val Ser Gln Gly Val His
145                 150                 155                 160

Pro Glu Tyr Arg Ala Val Leu Arg Ala Tyr Leu Glu Ala Val Gly Ala
                165                 170                 175

Lys Leu Leu Thr Leu Pro Leu Glu Gly Arg Thr Pro Leu Pro Glu
                180                 185                 190

Val Gly Glu Glu Val Gly Ala Val Val Gln Asn Pro Asn Phe Leu
            195                 200                 205

Gly Ala Leu Glu Asp Leu Gly Pro Phe Ala Glu Ala Ala His Gly Ala
    210                 215                 220

Gly Ala Leu Phe Val Ala Val Ala Asp Pro Leu Ser Leu Gly Val Leu
225                 230                 235                 240

Lys Pro Pro Gly Ala Tyr Gly Ala Asp Ile Ala Val Gly Asp Gly Gln
                245                 250                 255

Ser Leu Gly Leu Pro Met Gly Phe Gly Gly Pro His Phe Gly Phe Leu
                260                 265                 270

Ala Thr Lys Lys Ala Phe Val Arg Gln Leu Pro Gly Arg Leu Val Ser
            275                 280                 285

Glu Thr Val Asp Val Glu Gly Arg Arg Gly Phe Ile Leu Thr Leu Gln
290                 295                 300

Ala Arg Glu Gln Tyr Ile Arg Arg Ala Lys Ala Lys Ser Asn Ile Thr
305                 310                 315                 320

Thr Asn Ala Gln Leu Thr Ala Leu Met Gly Ala Met Tyr Leu Ala Ala
                325                 330                 335

Leu Gly Pro Glu Gly Leu Arg Glu Val Ala Leu Lys Ser Val Glu Met
                340                 345                 350

Ala His Lys Leu His Ala Leu Leu Leu Glu Val Pro Gly Val Arg Pro
            355                 360                 365

Phe Thr Pro Lys Pro Phe Phe Asn Glu Phe Ala Leu Ala Leu Pro Lys
                370                 375                 380

Asp Pro Glu Ala Val Arg Arg Ala Leu Ala Glu Arg Gly Phe His Gly
385                 390                 395                 400

Ala Thr Pro Val Pro Arg Glu Tyr Gly Glu Asn Leu Ala Leu Phe Ala
                405                 410                 415

Ala Thr Glu Leu His Glu Glu Asp Leu Leu Ala Leu Arg Glu Ala
            420                 425                 430

Leu Lys Glu Val Leu Ala Met Ser Phe Pro Leu Ile Phe Glu Arg Ser
                435                 440                 445

Arg Lys Gly Arg Arg Gly Leu Lys Leu Val Lys Ala Val Pro Lys Ala
                450                 455                 460

Glu Asp Leu Ile Pro Lys Glu His Leu Arg Glu Val Pro Pro Arg Leu
465                 470                 475                 480
```

-continued

Pro Glu Val Asp Glu Leu Thr Leu Val Arg His Tyr Thr Gly Leu Ser
              485                 490                 495

Arg Arg Gln Val Gly Val Asp Thr Thr Phe Tyr Pro Leu Gly Ser Cys
          500                 505                 510

Thr Met Lys Tyr Asn Pro Lys Leu His Glu Ala Ala Arg Leu Phe
          515                 520                 525

Ala Asp Leu His Pro Tyr Gln Asp Pro Arg Thr Ala Gln Gly Ala Leu
          530                 535                 540

Arg Leu Met Trp Glu Leu Gly Glu Tyr Leu Lys Ala Leu Thr Gly Met
545                 550                 555                 560

Asp Ala Ile Thr Leu Glu Pro Ala Ala Gly Ala His Gly Glu Leu Thr
              565                 570                 575

Gly Ile Leu Ile Ile Arg Ala Tyr His Glu Asp Arg Gly Glu Gly Arg
              580                 585                 590

Thr Arg Arg Val Val Leu Val Pro Asp Ser Ala His Gly Ser Asn Pro
          595                 600                 605

Ala Thr Ala Ser Met Ala Gly Tyr Gln Val Arg Glu Ile Pro Ser Gly
          610                 615                 620

Pro Glu Gly Glu Val Asp Leu Glu Ala Leu Lys Arg Glu Leu Gly Pro
625                 630                 635                 640

His Val Ala Ala Leu Met Leu Thr Asn Pro Asn Thr Leu Gly Leu Phe
              645                 650                 655

Glu Arg Arg Ile Leu Glu Ile Ser Arg Leu Cys Lys Glu Ala Gly Val
              660                 665                 670

Gln Leu Tyr Tyr Asp Gly Ala Asn Leu Asn Ala Ile Met Gly Trp Ala
          675                 680                 685

Arg Pro Gly Asp Met Gly Phe Asp Val Val His Leu Asn Leu His Lys
          690                 695                 700

Thr Phe Thr Val Pro His Gly Gly Gly Gly Pro Gly Ser Gly Pro Val
705                 710                 715                 720

Gly Val Lys Ala His Leu Ala Pro Tyr Leu Pro Val Pro Leu Val Glu
              725                 730                 735

Arg Gly Glu Glu Gly Phe Tyr Leu Asp Phe Asp Arg Pro Lys Ser Ile
              740                 745                 750

Gly Arg Val Arg Ser Phe Tyr Gly Asn Phe Leu Ala Leu Val Arg Ala
          755                 760                 765

Trp Ala Tyr Ile Arg Thr Leu Gly Leu Glu Gly Leu Lys Lys Ala Ala
          770                 775                 780

Ala Leu Ala Val Leu Asn Ala Arg Tyr Leu Lys Glu Leu Leu Lys Glu
785                 790                 795                 800

Lys Gly Tyr Arg Val Pro Tyr Asp Gly Pro Ser Met His Glu Phe Val
              805                 810                 815

Ala Gln Pro Pro Glu Gly Phe Arg Ala Leu Asp Leu Ala Lys Gly Leu
          820                 825                 830

Leu Glu Leu Gly Phe His Pro Pro Thr Val Tyr Phe Pro Leu Ile Val
          835                 840                 845

Lys Glu Ala Leu Met Val Glu Pro Thr Glu Thr Glu Ala Lys Glu Thr
850                 855                 860

Leu Glu Ala Phe Ala Glu Ala Met Gly Ala Leu Leu Lys Lys Pro Lys
865                 870                 875                 880

Glu Trp Leu Glu Asn Ala Pro Tyr Ser Thr Pro Val Arg Arg Leu Asp
              885                 890                 895

Glu Leu Arg Ala Asn Lys His Pro Lys Leu Thr Tyr Phe Asp Glu Gly

<210> SEQ ID NO 70
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 70
cggcctgcca acatccgttt gaaactcgag tttcaaacgg atgttggcag gttttg    57

<210> SEQ ID NO 71
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 71
tagctgttgt ccagactcga gccaaatat                                   29

<210> SEQ ID NO 72
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 72
ggtcaatccg ctgaagatgt ctccacact                                   29

<210> SEQ ID NO 73
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 73
tggagagttt actcaactac cagaccatg                                   29

<210> SEQ ID NO 74
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 74
ttcactaaag cggaatgagg atgcctgtc                                   29

<210> SEQ ID NO 75
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 75
aacggtcagg caggtcacct caagaagct                                   29

<210> SEQ ID NO 76
<211> LENGTH: 29
<212> TYPE: DNA
<213> ORGANISM: Artificial Sequence

```
<220> FEATURE:
<223> OTHER INFORMATION: Synthetic Polynucleotide

<400> SEQUENCE: 76
gccactgtaa gtggttcaat gtgcgcatg                                              29

<210> SEQ ID NO 77
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 77
agaagtgcca ttactgtcag agcatcatg                                              29

<210> SEQ ID NO 78
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 78
tacatcacca ccgtttcctc aggaggcta                                              29
```